US010059733B2

United States Patent
Suo et al.

(10) Patent No.: US 10,059,733 B2
(45) Date of Patent: Aug. 28, 2018

(54) GEMCITABINE ANALOGS

(71) Applicant: NUCORION PHARMACEUTICALS, INC., Wilmington, DE (US)

(72) Inventors: Zucai Suo, Dublin, OH (US); David J. Taggart, Columbus, OH (US); Sheng Cao, Milwaukee, WI (US)

(73) Assignee: NUCORION PHARMACEUTICALS, INC., Wilmington, DE (US)

( * ) Notice: Subject to any disclaimer, the term of this patent is extended or adjusted under 35 U.S.C. 154(b) by 219 days.

(21) Appl. No.: 15/122,506

(22) PCT Filed: Feb. 27, 2015

(86) PCT No.: PCT/US2015/018184
§ 371 (c)(1),
(2) Date: Aug. 30, 2016

(87) PCT Pub. No.: WO2015/134334
PCT Pub. Date: Sep. 11, 2015

(65) Prior Publication Data
US 2017/0088573 A1    Mar. 30, 2017

Related U.S. Application Data

(60) Provisional application No. 61/947,050, filed on Mar. 3, 2014.

(51) Int. Cl.
*A01N 43/04* (2006.01)
*A61K 31/70* (2006.01)
*C07H 19/06* (2006.01)
*C07H 19/10* (2006.01)
*C07H 19/11* (2006.01)
*A61K 45/06* (2006.01)
*A61K 31/7068* (2006.01)
*A61K 31/7064* (2006.01)
*A61K 31/706* (2006.01)

(52) U.S. Cl.
CPC ............ *C07H 19/06* (2013.01); *A61K 45/06* (2013.01); *C07H 19/10* (2013.01); *C07H 19/11* (2013.01); *A61K 31/706* (2013.01); *A61K 31/7064* (2013.01); *A61K 31/7068* (2013.01)

(58) Field of Classification Search
None
See application file for complete search history.

(56) References Cited

FOREIGN PATENT DOCUMENTS

| WO | WO 2006/065525 | 6/2006 |
| WO | WO 2012/040126 | 3/2012 |
| WO | WO 2013/142525 | 9/2013 |
| WO | WO 2014/074725 | 5/2014 |
| WO | WO 2014/145207 | 9/2014 |
| WO | WO 2015/081133 | 6/2015 |

OTHER PUBLICATIONS

Slusarczyk et al. J. Med. Chem. (2013), vol. 57, pp. 1531-1542.*
Almarasson, O., et. al., "Crystal Engineering of the Composition of Pharmaceutical Phases. Do Pharmaceutical Co-crystals Represent a New Path to Improved Medicines?" The Royal Society of Chemistry, 1889-1896 (2004).
Chou T.C. and Talalay P. "Analysis of combined drug effects: a new look at a very old problem." Trends Pharmacol Sci 4:450-4 (1983).
Chou T.C. and Talalay P., "Quantitative analysis of dose-effect relationships: the combined effects of multiple drugs or enzyme inhibitors." Adv Enzyme Regul 22:27-55 (1984).
Chou, T.C., Theoretical basis, experimental design, and computerized simulation of synergism and antagonism in drug combination studies. Pharmacol Rev. 58(3):621-81 (2006).
European Search Report issued in Application No. EP15758660.3 dated Nov. 7, 2017.
Wu, et al, Synthesis and Biological Activity of a Gemcitabine Phosphoramidate Prodrug, J. Med Chem 50(15):3743-3746 (2007).
Zhao, et al, Synthesis and Biological Evaluation of Oral Prodrugs Based on the Structure of Gemcitabine, Chem Bio & Drug Des 80(3):479-488 (2012).

* cited by examiner

*Primary Examiner* — Patrick T Lewis
(74) *Attorney, Agent, or Firm* — Knobbe, Martens, Olson & Bear LLP

(57) ABSTRACT

Gemcitabine analogs, including monophosphorylated analogs, are described herein and are suitable for use in pharmaceutical compositions, kits and treatment methods. The treatment methods include treatment of viral infections, including, but not limited to, treatment of Hepatitis C Virus, and uncontrolled cellular proliferation, including cancer, such as, but not limited to, non-small cell lung cancer, pancreatic cancer, bladder cancer, breast cancer, liver cancer, esophageal cancer and lymphoma.

34 Claims, 2 Drawing Sheets

GEMCITABINE ANALOGS

RELATED APPLICATIONS

This application is the U.S. national phase of International Application No. PCT/US2015/018184 filed Feb. 27, 2015 and published in English as WO 2015/134334 on Sep. 11, 2015 which claims the benefit of U.S. Provisional Application No. 61/947,050 filed Mar. 3, 2014 the disclosure of which is incorporated herein in its entirety.

FIELD OF THE INVENTION

The present invention is in the fields of chemistry and medicine. More particularly, the present invention is directed to gemcitabine analogs and their pharmaceutical compositions and use.

BACKGROUND OF THE INVENTION

Gemcitabine HCl (2',2'-difluorodeoxycytidine HCl, dFdC), marketed as Gemzar®, is a clinically approved anticancer drug for the treatment of a wide spectrum of cancers including pancreatic, non-small cell lung cancer, breast, bladder, head and neck, mesothelioma, cervical, and ovarian cancers. Gemcitabine is a polar deoxycytidine analog and requires nucleoside transporters to translocate across the cellular membrane. Gemcitabine is known to enter cells principally through Equilibrative Nucleoside Transporter 1 (ENT1). Gemcitabine first needs to be phosphorylated to gemcitabine monophosphate (dFdCMP) by deoxycytidine kinase (dCK), and dFdCMP is then subsequently phosphorylated by nucleotide kinases to di- and tri-phosphorylated gemcitabine (dFdCDP and dFdCTP, respectively) which are active metabolites of gemcitabine. Unfortunately, tumor cells often acquire gemcitabine resistance either during or after gemcitabine treatment.

Various derivatives of gemcitabine have been developed, for example, in attempts to improve in vitro performance and/or to expand therapeutic uses. Some such derivatives have been suggested for use in treating viral infections, including HCV. An estimated 170 million people throughout the world are infected with HCV. More than 70% of these individuals remain chronically infected for life, of which 15-20% eventually develops liver cirrhosis and hepatocellular carcinoma. The current therapy for HCV infections is the combination of ribavirin, interferon-α (IFN-α), and recently approved HCV inhibitors such as boceprevir, marketed as Victrelis® and telaprevir, marketed as Incivek®. Unfortunately, in addition to severe side effects in some cases, the sustained response rate of such therapies is less than desirable and may be genotype-dependent. Thus, there is a need in the art for new gemcitabine analogs that are effective and provide improvement for various applications.

SUMMARY OF THE INVENTION

Accordingly, one object of the invention is to provide new gemcitabine analogs, and compositions, kits and treatment methods employing such analogs.

In a specific embodiment, the invention is directed to compound of formula (I):

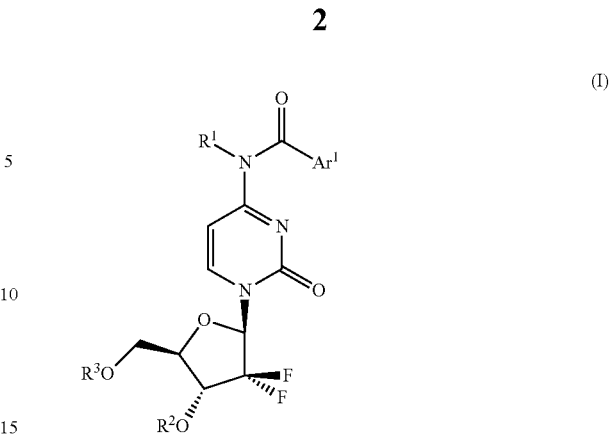

(a) wherein $Ar^1$ is:

(a)(i) phenyl or naphthyl, wherein the phenyl or naphthyl is substituted with 1, 2, 3, 4, or 5 groups independently selected from halo, cyano, nitro, hydroxy, thiol, —$NR^{9a}R^{9b}$, C1-C6 alkyl, C1-C6 monohaloalkyl, C1-C6 polyhaloalkyl, C1-C6 alkoxy, C1-C6 monohaloalkoxy, C1-C6 polyhaloalkoxy, C1-C6 hydroxyalkyl, C1-C6 alkylthiol, optionally substituted phenyl, optionally substituted benzyl, and optionally substituted phenoxy, —$C(O)R^{12}$, —$C(O)OR^{12}$, —$C(O)NHR^{12}$, —OC(O)$R^{12}$, —NHC(O)$R^{12}$, and —NHC(O)$OR^{12}$, in which each of $R^{9a}$ and $R^{9b}$ is independently selected from hydrogen, C1-C4 alkyl, and an amine protecting group, and $R^{12}$ is C1-C6 alkyl; or (a)(ii) a bicyclic or polycyclic fused ring system comprising an aryl ring fused to one or more 4-, 5-, 6-, 7-, or 8-membered cycloalkyl or heterocycloalkyl or fused to a 4-, 5-, 6-, 7-, or 8-membered cycloalkyl or heterocycloalkyl which is fused to a second aryl ring, wherein the aryl rings of the bicyclic or polycyclic fused ring system are each independently selected from phenyl, pyridinyl, pyrimidinyl, pyridazinyl, pyrazinyl, and triazinyl;

wherein the aryl rings of the bicyclic or polycyclic fused ring system are each optionally substituted with 1, 2, or 3 groups independently selected from halogen, —OH, —CN, —$NH_2$, thiol, C1-C6 alkyl, C1-C6 alkoxy, C1-C6 monohaloalkyl, C1-C6 polyhaloalkyl, C1-C6 alkylamino, and C1-C6 dialkylamino;

wherein the cycloalkyl or heterocycloalkyl of the bicyclic or polycyclic fused ring system is optionally substituted with 1, 2, 3, 4, or 5 groups independently selected from halogen, —OH, —CN, —$NH_2$, thiol, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)$OR^8$, and —(C=O)$NR^{9a}R^{9b}$, in which each $R^8$ is independently selected from hydrogen, C1-C6 alkyl, and a hydroxyl protecting group, and each of $R^{9a}$ and $R^{9b}$ is as defined above;

(b) wherein $R^1$ is selected from hydrogen, C1-C4 alkyl, and an amine protecting group; and (c)(i) wherein $R^2$ is selected from hydrogen and a hydroxyl protecting group and $R^3$ is a moiety having a structure represented by formula (II):

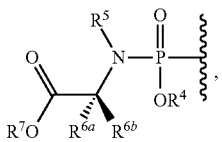

wherein R⁴ is selected from C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, Ar², —(C1-C6 alkyl)-(C3-C8 cycloalkyl), —(C1-C6 alkyl)-(C2-C8 heterocycloalkyl), and —(C1-C6 alkyl)-Ar²;

wherein R⁵ is selected from hydrogen, C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, Ar², —(C1-C6 alkyl)-(C3-C8 cycloalkyl), —(C1-C6 alkyl)-(C2-C8 heterocycloalkyl), and —(C1-C6 alkyl)-Ar²;

wherein each of $R^{6a}$ and $R^{6b}$ is selected from hydrogen, C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, Ar², —(C1-C6 alkyl)-(C3-C8 cycloalkyl), —(C1-C6 alkyl)-(C2-C8 heterocycloalkyl), and —(C1-C6 alkyl)-Ar², provided that each of $R^{6a}$ and $R^{6b}$ are not the same; and wherein R⁷ is selected from C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, Ar², —(C1-C6 alkyl)-(C3-C8 cycloalkyl), —(C1-C6 alkyl)-(C2-C8 heterocycloalkyl), and —(C1-C6 alkyl)-Ar²;

in which Ar² is an optionally substituted phenyl, naphthalene, monocyclic heteroaryl, bicyclic heteroaryl or polycyclic heteroaryl; or (c)(ii) wherein R² and R³ together comprise a divalent moiety having a structure represented by formula (III):

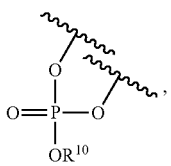

wherein R¹⁰ is selected from hydrogen, C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, Ar², —(C1-C6 alkyl)-(C3-C8 cycloalkyl), —(C1-C6 alkyl)-(C2-C8 heterocycloalkyl), —(C1-C6 alkyl)-Ar², in which Ar² is as defined above;

or a pharmaceutically acceptable salt, hydrate, solvate, or polymorph thereof.

In another embodiment, the invention is directed to a compound of formula (IV):

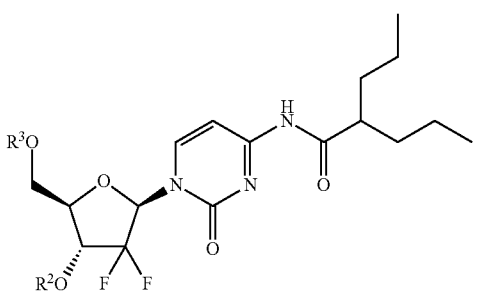

wherein (i) R² is selected from hydrogen and a hydroxyl protecting group and R³ is a moiety having a structure represented by formula (II):

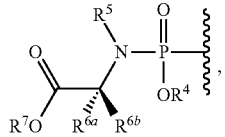

wherein R⁴ is selected from C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, Ar², —(C1-C6 alkyl)-(C3-C8 cycloalkyl), —(C1-C6 alkyl)-(C2-C8 heterocycloalkyl), and —(C1-C6 alkyl)-Ar²;

wherein R⁵ is selected from hydrogen, C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, Ar², —(C1-C6 alkyl)-(C3-C8 cycloalkyl), —(C1-C6 alkyl)-(C2-C8 heterocycloalkyl), and —(C1-C6 alkyl)-Ar²;

wherein each of $R^{6a}$ and $R^{6b}$ is selected from hydrogen, C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, Ar², —(C1-C6 alkyl)-(C3-C8 cycloalkyl), —(C1-C6 alkyl)-(C2-C8 heterocycloalkyl), and —(C1-C6 alkyl)-Ar², provided that each of $R^{6a}$ and $R^{6b}$ are not the same; and wherein R⁷ is selected from C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, Ar², —(C1-C6 alkyl)-(C3-C8 cycloalkyl), —(C1-C6 alkyl)-(C2-C8 heterocycloalkyl), and —(C1-C6 alkyl)-Ar²;

in which Ar² is an optionally substituted phenyl, naphthalene, monocyclic heteroaryl, bicyclic heteroaryl or polycyclic heteroaryl; or (ii) R² and R³ together comprise a divalent moiety having a structure represented by formula (III):

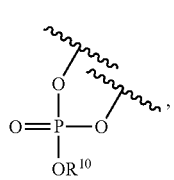

wherein R¹⁰ is selected from hydrogen, C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, Ar², —(C1-C6 alkyl)-(C3-C8 cycloalkyl), —(C1-C6 alkyl)-(C2-C8 heterocycloalkyl), —(C1-C6 alkyl)-Ar², in which Ar² is as defined above;

or a pharmaceutically acceptable salt, hydrate, solvate, or polymorph thereof.

In another embodiment, the invention is directed to compound of formula (V):

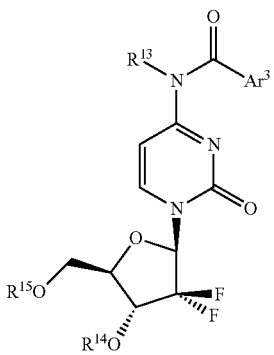

(V)

(a) wherein $Ar^3$ is naphthyl or is a bicyclic or polycyclic fused ring system comprising an aryl ring fused to one or more 4-, 5-, 6-, 7-, or 8-membered cycloalkyl or fused to a 4-, 5-, 6-, 7-, or 8-membered cycloalkyl or heterocycloalkyl which is fused to a second aryl ring, wherein the aryl rings of the bicyclic or polycyclic fused ring system are each independently selected from phenyl, pyridinyl, pyrimidinyl, pyridazinyl, pyrazinyl, and triazinyl;

wherein the naphthyl or the aryl rings of the bicyclic or polycyclic fused ring system are each optionally substituted with 1, 2, or 3 groups independently selected from halogen, —OH, —CN, —$NH_2$, thiol, C1-C6 alkyl, C1-C6 alkoxy, C1-C6 monohaloalkyl, C1-C6 polyhaloalkyl, C1-C6 alkylamino, and C1-C6 dialkylamino;

wherein the cycloalkyl of the bicyclic or polycyclic fused ring system is optionally substituted with 1, 2, 3, 4, or 5 groups independently selected from halogen, —OH, —CN, —$NH_2$, thiol, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)$OR^8$, and —(C=O)$NR^{9a}R^{9b}$, in which each $R^8$ is independently selected from hydrogen, C1-C6 alkyl, and a hydroxyl protecting group, and each of $R^{9a}$ and $R^{9b}$ is independently selected from hydrogen, C1-C4 alkyl, and an amine protecting group;

(b) wherein $R^{13}$ is selected from hydrogen, C1-C4 alkyl, and an amine protecting group; and (c) wherein $R^{14}$ is selected from hydrogen, C1-C6 alkyl and a hydroxyl protecting group and $R^{15}$ is selected from hydrogen and a hydroxyl protecting group, or a pharmaceutically acceptable salt, hydrate, solvate, or polymorph thereof.

In further embodiments, the invention is directed to pharmaceutical compositions comprising a compound of formula (I), formula (IV), or formula (V), and a pharmaceutically acceptable carrier.

In additional embodiments, the invention is directed to kits comprising a compound of formula (I), formula (IV), or formula (V), (a) an antiviral agent or a substance known to increase risk of viral infection, and optionally instructions for treating a viral infection, or (b) a drug known to treat a disorder of uncontrolled cellular proliferation or a substance known to increase risk of uncontrolled cellular proliferation, and optionally instructions for treating a disorder of uncontrolled cellular proliferation.

The invention is also directed to methods for treating a subject for viral infection, which methods comprise the step of administering to the subject a therapeutically or prophylactically effective amount of a compound of formula (I), formula (IV), or formula (V), or a pharmaceutical composition containing such a compound.

The invention is also directed to methods for treating a disorder of uncontrolled cellular proliferation, which methods comprise the step of administering to a subject having such disorder a therapeutically or prophylactically effective amount of a compound of formula (I), formula (IV), or formula (V), or a pharmaceutical composition containing such a compound.

In additional embodiments, the invention is directed to methods for inhibiting viral replication within at least one cell, which methods comprise the step of administering to the cell a compound of formula (I), formula (IV), or formula (V), or a pharmaceutical composition containing such a compound, in an amount effective to inhibit viral replication within the at least one cell.

In additional embodiments, the invention is directed to methods for arresting tumor growth, which methods comprise the step of administering to at least one tumor cell a compound of formula (I), formula (IV), or formula (V), or a pharmaceutical composition containing such a compound, in an amount effective to arrest growth of the tumor.

In additional embodiments of any of such methods, the subject or cell has a resistance to gemcitabine.

The compounds according to the invention have various improvements and, in turn, provide improved compositions, kits and methods, particularly for prophylactic and/or therapeutic treatments. As will be discussed in detail below, one important feature of the monophosphate compounds of the invention is that, in vivo, they circumvent the initial phosphorylation step of gemcitabine activation which is catalyzed by dCK, and therefore the compounds are effective in cells which have developed gemcitabine resistance due to dCK deficiency. Further, the present monophosphorylated compounds do not require the hENT1 transporter for cell entry and, rather, enter cells by passive diffusion. Thus, cells which have lost the ENT1 transporter activity will not be resistant to the present compounds. The present compounds are therefore effective in cells which have developed resistance to treatment with gemcitabine. Additional advantages of the various embodiments of the invention will be more fully apparent in view of the following detailed description.

BRIEF DESCRIPTION OF THE DRAWINGS

The accompanying figures illustrate several aspects and together with the description serve to further explain various aspects of certain embodiments of the invention.

DETAILED DESCRIPTION

Figure 1:
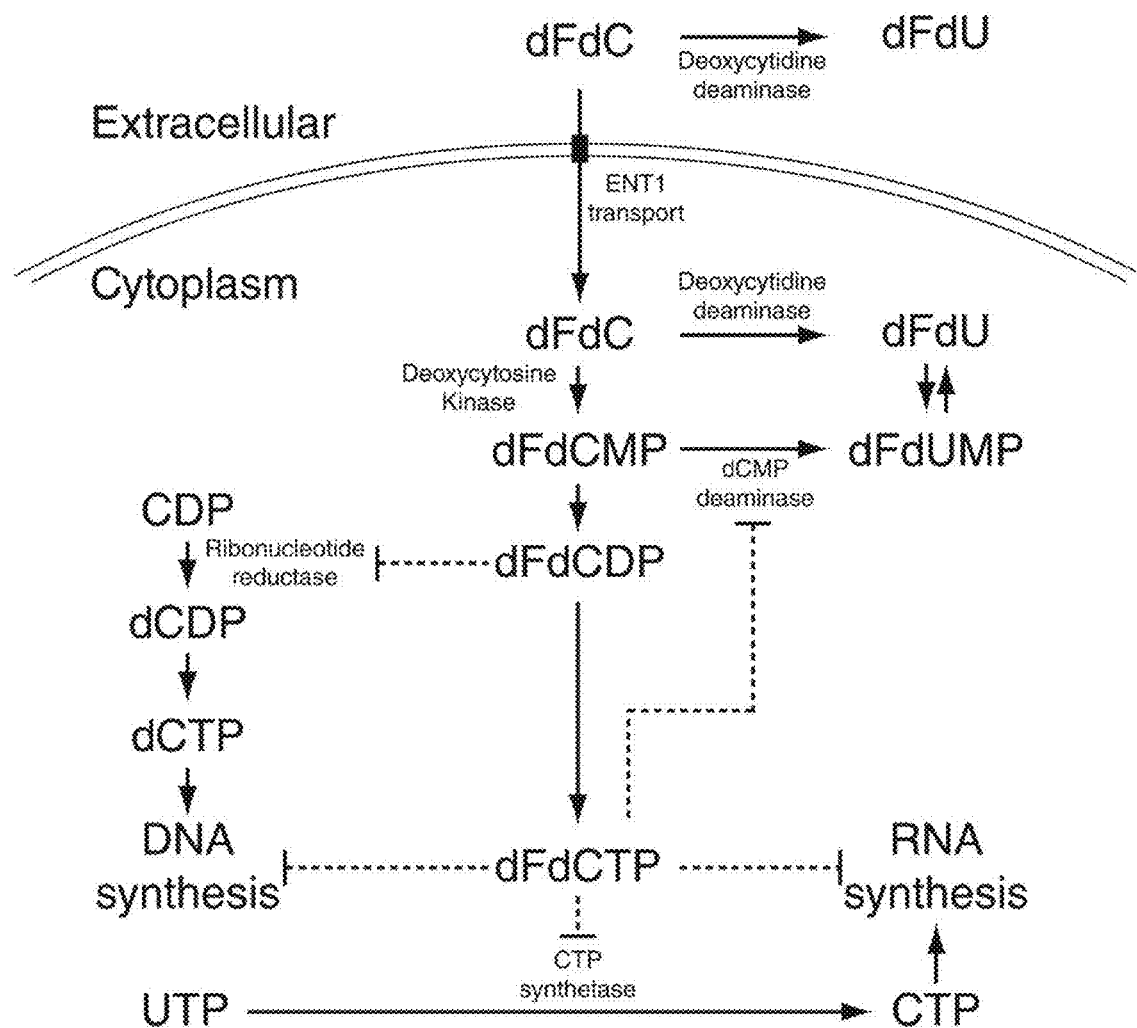
FIG. 1 discloses a reaction scheme for intracellular activation of gemcitabine; and self potentiation pathways.

Some embodiments described herein relate to analogs of gemcitabine and their pharmaceutical compositions and methods of use. While not wishing to be bound by any particular theory, one source of acquired resistance to gemcitabine is dCK deficiency. Inefficient intracellular monophosphorylation of gemcitabine may reduce the efficacy of gemcitabine drastically. Gemcitabine resistance can also result from loss of human ENT1 activity. Therefore, some embodiments include monophosphate analogs of gemcitabine.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment prior to the administering step. In further aspects, the disclosed methods further comprise the step of identifying a subject in need of treatment for the disorder. In one aspect, a subject can be treated prophylactically with a compound or composition disclosed herein, as discussed herein elsewhere.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the phrase "identified to be in need of treatment for a disorder," or the like, refers to selection of a subject based upon need for treatment of the disorder. For example, a subject can be identified as having a need for treatment of a disorder based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, a target receptor, or other biological entity together in such a manner that the compound can affect the activity of the target, either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "$IC_{50}$," is intended to refer to the concentration of a substance (e.g., a compound or a drug) that is required for 50% inhibition of a biological process, or component of a process. For example, $IC_{50}$ refers to the half maximal (50%) inhibitory concentration (IC) of a substance as determined in a suitable assay.

As used herein, "$TC_{50}$," is intended to refer to toxic concentration of a substance (e.g., a compound or a drug) necessary to reduce the cell population by 50%. $TC_{50}$ can, for example, be determined in a suitable assay, for example, an assay as disclosed herein.

The term "pharmaceutically acceptable" describes a material that is not biologically or otherwise undesirable, i.e., without causing an unacceptable level of undesirable biological effects or interacting in a deleterious manner. The term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds, except as explicitly stated. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, sbutyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C6 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a cycloalkyl group as defined above where at least one of the carbon atoms of the ring is replaced with a heteroatom such as, but not limited to, nitrogen, oxygen, sulfur, or phosphorus. The cycloalkyl group and heterocycloalkyl group can be monocyclic or polycyclic and can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1-OA^2$ or $—OA^1 (OA^2)_a—OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups. The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, $—NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "aldehyde" as used herein is represented by the formula $—C(O)H$. Throughout this specification "C(O)" is a short hand notation for a carbonyl group, i.e., C=O.

The terms "amine" or "amino" as used herein are represented by the formula $—NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is $—NH_2$.

The term "alkylamino" as used herein is represented by the formula $—NH(-alkyl)$ where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula $—N(-alkyl)_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula —(A$^1$O(O)C-A$^2$-C(O)O)$_a$— or —A$^1$O(O)C-A$^2$-OC(O))$_a$, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula —(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide" as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl" as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5-, 6-, 7- or 8-membered ring containing 1, 2 or 3 ring heteroatoms or wherein a pyridine ring is fused to a 5-, 6-, 7- or 8-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2Hchromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "polycyclic" as used herein refers to three or more ring systems, i.e., tricyclic, tetracyclic, pentacyclic, or other fused cyclized systems. A polycyclic system may be aliphatic, partially unsaturated or fully saturated, and may optionally contain one to four heteroatoms independently selected from oxygen, nitrogen, and sulfur, wherein a nitrogen and sulfur heteroatom optionally can be oxidized and a nitrogen heteroatom optionally can be substituted.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "sulfo-oxo" as used herein is represented by the formulas —$S(O)A^1$, $S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are nonsuperimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as 2 H, 3 H, 13 C, 14 C, 15 N, 18 O, 17 O, 35 S, 18 F and 36 Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as 3 H and 14 C are incorporated, are useful in drug and/or substrate tissue distribution assays. Tritiated, i.e., 3 H, and carbon-14, i.e., 14 C, isotopes are particularly preferred for their ease of preparation and detectability. Further, substitution with heavier isotopes such as deuterium, i.e., 2 H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form. Likewise, amides with an N-hydrogen can exist in an equilibrium of the amide form and the imidic acid form. As another example, pyrazoles can exist in two tautomeric forms. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms. In certain embodiments, the polymorphs are crystallized from a solvent selected from water, methanol, ethanol, propanol, isopropanol, acetone acetonitrile, ethyl acetate, hexane and mixtures of two or more of these. Additionally, the polymorphs may be crystallized from such a solvent using one or more of heating, cooling, and vacuum drying, with or without the use of seeding.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental Volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and CE would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

The compounds as disclosed herein include chiral carbons. When the chiral carbons are depicted as straight lines in the disclosed formulas, it is understood that both the (R) and (S) configurations of the chiral carbon, and hence both enantiomers, individually and as mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). Depiction of one chiral carbon configuration in a formula is non-limiting of the configuration of any additional chiral carbons in such formula.

In one embodiment, the invention is directed compounds which are monophosphorylated gemcitabine analogs, also referred to herein as nucleoside analogs, nucleoside analog prodrugs, and/or gemcitabine derivatives or prodrugs.

Without wishing to be bound by theory, it is believed that the rate-limiting step for the intracellular activation of gemcitabine (dFdC) is predicted to be the phosphorylation of dFdC, catalyzed by dCK, to generate dFdCMP (see FIG. 1). To circumvent this rate-limiting step, we provide the monophosphate compounds described herein.

More specifically, gemcitabine is initially transported into cells through the action of Equilibrative Nucleoside Transporter 1 (ENT1), and to a lesser extent by Concentrative Nucleoside Transporter 1 (CNT1) and Concentrative Nucleoside Transporter 3 (CNT3). Once inside a cell, gemcitabine exerts its antiproliferative activities through multiple mechanisms. Initially, gemcitabine must be intracellularly phosphorylated by dCK in a rate-limiting step to generate gemcitabine monophosphate (dFdCMP). This monophosphate form is subsequently phosphorylated by nucleotide kinases to produce the active metabolites gemcitabine diphosphate (dFdCDP) and gemcitabine triphosphate (dFdCTP). The triphosphate form functions as a masked chain terminator when incorporated into DNA or RNA. Gemcitabine is referred to as a "masked chain terminator" due to the fact that once dFdCTP is incorporated into a newly-synthesized DNA strand, DNA polymerases are able to incorporate one additional nucleotide before replication is blocked. Thus, at a stalled replication fork, the incorporated gemcitabine is shielded from the exonuclease activity of replicative DNA polymerases. In addition to functioning as a masked chain terminator, gemcitabine also inhibits multiple steps within the pyrimidine biosynthesis pathway. dFdCDP inhibits ribonucleotide reductase while dFdCTP inhibits CTP synthetase, and deoxycytidine monophosphate deaminase (FIG. 1). The inhibition of these enzymes leads to a decrease in cellular CTP and dCTP pools, and ultimately, an increase in the molar ratio of gemcitabine to natural nucleotides within cells. This ability of gemcitabine to reduce the cellular levels of competing natural pyrimidines and thereby increase the likelihood of incorporation of dFdCTP into DNA and RNA chains is termed "self-potentiation". Detrimental to its activity, gemcitabine is rapidly deaminated by cytidine deaminase both intracellularly and in plasma to yield the inactive metabolite 2',2'-difluorodeoxyuridine (dFdU). Additionally, dFdCMP is deaminated intracellularly by deoxycytidylate deaminase to form the inactive metabolite dFdUMP. The inventive compounds protect the amine group of the cytosine base from deamination.

Importantly, many types of cancer that are initially susceptible to gemcitabine therapy develop gemcitabine resistance over time. The known mechanisms by which cancer cells develop gemcitabine resistance are 1) loss of dCK activity which is required for the initial phosphorylation step of intracellular gemcitabine activation; 2) overexpression of ribonucleotide reductase which increases cellular pools of dCTP to compete with gemcitabine for incorporation into DNA; 3) loss of nucleotide transporter function which significantly reduces cellular uptake of gemcitabine; and 4) enhanced cytidine deaminase-catalyzed conversion of gemcitabine into dFdU. In order to circumvent these mechanisms of acquired gemcitabine resistance, the present monophosphorylated compounds bypass the requirement of phosphorylation by dCK, and are rapidly converted to dFdCDP to more efficiently inhibit ribonucleotide reductase. Further, the present monophosphorylated compounds do not appear to require the hENT1 transporter for cell entry and, rather, enter cells by passive diffusion. Thus, cells which have lost ENT1 transporter activity will not be resistant to the present compounds. Thus, the present compounds are effective in cells which have developed resistance to treatment with gemcitabine.

In one embodiment, the invention is directed to compounds of formula (I):

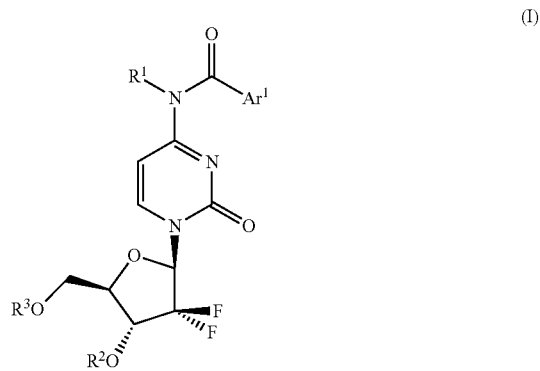

(a) wherein $Ar^1$ is:
(a)(i) phenyl or naphthyl,
wherein the phenyl or naphthyl is substituted with 1, 2, 3, 4, or 5 groups independently selected from halo, cyano, nitro, hydroxy, thiol, —$NR^{9a}R^{9b}$, C1-C6 alkyl, C1-C6 monohaloalkyl, C1-C6 polyhaloalkyl, C1-C6 alkoxy, C1-C6 monohaloalkoxy, C1-C6 polyhaloalkoxy, C1-C6 hydroxyalkyl, C1-C6 alkylthiol, optionally substituted phenyl, optionally substituted benzyl, and optionally substituted phenoxy, —$C(O)R^{12}$, —$C(O)OR^{12}$, —$C(O)NHR^{12}$, —$OC(O)R^{12}$, —$NHC(O)R^{12}$, and —$NHC(O)OR^{12}$, in which each of $R^{9a}$ and $R^{9b}$ is independently selected from hydrogen, C1-C4 alkyl, and an amine protecting group, and $R^{12}$ is C1-C6 alkyl; or
(a)(ii) a bicyclic or polycyclic fused ring system comprising an aryl ring fused to one or more 4-, 5-, 6-, 7-, or 8-membered cycloalkyl or heterocycloalkyl or fused to a 4-, 5-, 6-, 7-, or 8-membered cycloalkyl or heterocycloalkyl which is fused to a second aryl ring, wherein the aryl rings of the bicyclic or polycyclic fused ring system are each selected from phenyl, pyridinyl, pyrimidinyl, pyridazinyl, pyrazinyl, and triazinyl;

wherein the aryl rings of the bicyclic or polycyclic fused ring system are optionally substituted with 1, 2, or 3 groups independently selected from halogen, —OH, —CN, —NH$_2$, thiol, C1-C6 alkyl, C1-C6 alkoxy, C1-C6 monohaloalkyl, C1-C6 polyhaloalkyl, C1-C6 alkylamino, and C1-C6 dialkylamino;

wherein the cycloalkyl or heterocycloalkyl of the bicyclic or polycyclic fused ring system is optionally substituted with 1, 2, 3, 4, or 5 groups independently selected from halogen, —OH, —CN, —NH$_2$, thiol, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)OR, and —(C=O)NR$^{9a}$R$^{9b}$, in which each R$^8$ is independently selected from hydrogen, C1-C6 alkyl, and a hydroxyl protecting group, and each of R$^{9a}$ and R$^{9b}$ is as defined above;

(b) wherein R$^1$ is selected from hydrogen, C1-C4 alkyl, and an amine protecting group; and (c)(i) wherein R$^2$ is selected from hydrogen and a hydroxyl protecting group and R$^3$ is a moiety having a structure represented by formula (II):

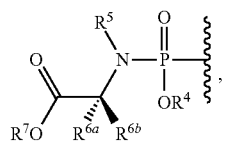

(II)

wherein R$^4$ is selected from C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, Ar$^2$, —(C1-C6 alkyl)-(C3-C8 cycloalkyl), —(C1-C6 alkyl)-(C2-C8 heterocycloalkyl), and —(C1-C6 alkyl)-Ar$^2$;

wherein R$^5$ is selected from hydrogen, C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, Ar$^2$, —(C1-C6 alkyl)-(C3-C8 cycloalkyl), —(C1-C6 alkyl)-(C2-C8 heterocycloalkyl), and —(C1-C6 alkyl)-Ar$^2$;

wherein each of R$^{6a}$ and R$^{6b}$ is selected from hydrogen, C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, Ar$^2$, —(C1-C6 alkyl)-(C3-C8 cycloalkyl), —(C1-C6 alkyl)-(C2-C8 heterocycloalkyl), and —(C1-C6 alkyl)-Ar$^2$, provided that each of R$^{6a}$ and R$^{6b}$ are not the same; and wherein R$^7$ is selected from C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, Ar$^2$, —(C1-C6 alkyl)-(C3-C8 cycloalkyl), —(C1-C6 alkyl)-(C2-C8 heterocycloalkyl), and —(C1-C6 alkyl)-Ar$^2$;

in which Ar$^2$ is an optionally substituted phenyl, naphthalene, monocyclic heteroaryl, bicyclic heteroaryl or polycyclic heteroaryl; or (c)(ii) wherein R$^2$ and R$^3$ together comprise a divalent moiety having a structure represented by formula (III):

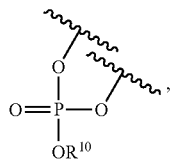

(III)

wherein R$^{10}$ is selected from hydrogen, C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, Ar$^2$, —(C1-C6 alkyl)-(C3-C8 cycloalkyl), —(C1-C6 alkyl)-(C2-C8 heterocycloalkyl), —(C1-C6 alkyl)-Ar$^2$, in which Ar$^2$ is as defined above;

or a pharmaceutically acceptable salt, hydrate, solvate, or polymorph thereof.

In one specific embodiment, Ar$^1$ is (a)(ii) the bicyclic or polycyclic fused ring system comprising an aryl ring fused to one or more 4-, 5-, 6-, 7-, or 8-membered cycloalkyl or heterocycloalkyl. In a more specific embodiment, Ar$^1$ is (a)(ii) a bicyclic fused ring system comprising an aryl ring fused to a 5-, 6-, 7-, or 8-membered cycloalkyl or heterocycloalkyl, or, more specifically, a 5-, 6-, 7-, or 8-membered heterocycloalkyl. In certain embodiments, the heterocycloalkyl group may be in a spiro configuration, for example, spiro (2,4) heptane, wherein one or more of the cyclo atoms is a heteroatom. In more specific embodiments of such compounds, the aryl ring is phenyl and the heterocycloalkyl comprises 1 or 2 heteroatoms selected from O, S and N. In further embodiments, the heterocycloalkyl group is a 5-, 6-, 7-, or 8-membered heterocycloalkyl containing one or two oxygen atoms as the hetero atoms, one or two nitrogen atoms as the heteroatoms, one or two sulfur atoms as the heteroatoms, one oxygen and one nitrogen as the heteroatoms, or one nitrogen and one sulfur as the heteroatoms.

In additional specific embodiments of such compounds, the heterocycloalkyl is unsubstituted or has 1, 2 or 3 substituents independently selected from halogen, C1-C6 alkyl, C1-C6 monohaloalkyl, C1-C6 polyhaloalkyl, and —(C=O)OR$^8$ in which each R$^8$ is independently selected from hydrogen, C1-C6 alkyl, and a hydroxyl protecting group. Hydroxyl protecting groups are well known in the art, particularly to obtain chemoselectivity, and include, but are not limited to methoxymethyl ether (MOM), tetrahydropyranyl (THP), t-butyl ether, allyl ether, benzyl, tetraisopropyldisilylene (TIPDS), tert-butyldimethylsilyl (TBDMS), t-Butyldiphenylsilyl (TBDPS), acetyl, pivalic acid ester, acetonide, benzoyl, and benzylidene acetal. In more specific embodiments, the heterocycloalkyl is unsubstituted or has 1, 2 or 3 substituents independently selected from fluoro, chloro, bromo, iodo, methyl, fluoromethyl, difluoromethyl, trifluoromethyl, ethyl, propyl, butyl, —(C=O)OH, and —(C=O)OCH$_3$.

In additional specific embodiments, Ar$^1$ is polycyclic fused ring system comprising an aryl ring fused to one or more 4-, 5-, 6-, 7-, or 8-membered cycloalkyl, wherein one or more of the aryl ring and cycloalkyl structures are optionally substituted with one or more groups selected from —OH, —CN, —NH$_2$, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)OR$^8$, and —(C=O)NR$^{9a}$R$^{9b}$, in which each R$^8$ is independently selected from hydrogen, C1-C6 alkyl, and a hydroxyl protecting group, and each of $R^{9a}$ and $R^{9b}$ is as defined above. In a more specific embodiment, $Ar^1$ is polycyclic fused ring system of the formula:

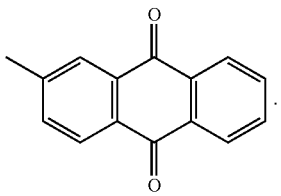 [SMILES: Cc1ccc2c(c1)C(=O)c1ccccc1C2=O]

In other embodiments, $Ar^1$ is naphthyl, substituted naphthyl or substituted phenyl. In more specific embodiments, the naphthyl or phenyl is substituted with 1, 2, 3, 4, or 5 groups independently selected from halo, cyano, nitro, hydroxy, thiol, —$NH_2$, —NH(C1-C4 alkyl), —$N(C1-C4$ alkyl$)_2$, C1-C4 alkyl, C1-C4 monohaloalkyl, C1-C4 polyhaloalkyl, C1-C4 alkoxy, C1-C4 monohaloalkoxy, C1-C4 polyhaloalkoxy, optionally substituted phenyl, optionally substituted benzyl, and optionally substituted phenoxy, —C(O)$R^{12}$, —C(O)O$R^{12}$, —C(O)NH$R^{12}$, —OC(O)$R^{12}$, —NHC(O)$R^{12}$, and —NHC(O)O$R^{12}$, in which each $R^{12}$ is C1-C6 alkyl, and an amine protecting group. Suitable amine protecting groups are known in the art and include, but are not limited to, Fmoc, BOC, Cbz, acetyl, trifluoroacetamide, phthalimide, benzyl, triphenylmethylamine, benzylideneamine, and ptoluenesulfonamide.

In more specific embodiments, $Ar^1$ is moiety having a structure represented by a formula:

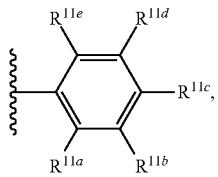

wherein at least one of $R^{11a}$, $R^{11b}$, $R^{11c}$, $R^{11d}$, and $R^{11e}$ is not hydrogen;

wherein $R^{11a}$ and $R^{11e}$ are independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted benzyl, optionally substituted phenoxy, nitro, —$NH_2$, —NH(C1-C4 alkyl), and —N(C1-C4 alkyl$)_2$;

wherein $R^{11b}$ and $R^{11d}$ are independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —$NH_2$, —NHC1-C4 alkyl, and —N(C1-C4 alkyl$)_2$; and wherein $R^{11c}$ is selected from hydrogen, fluoro, chloro, bromo, iodo, methyl, methoxy, fluoromethyl, fluoromethoxy, difluoromethyl, difluoromethoxy, trifluoromethyl, NH(C1-C4 alkyl)trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, —C(O)$R^{12}$, —C(O)O$R^{12}$, —C(O)NH$R^{12}$, —OC(O)$R^{12}$, —NHC(O)$R^{12}$, and —NHC(O)O$R^{12}$, wherein $R^{12}$ is hydrogen, methyl, ethyl, propyl, butyl, pentyl, or hexyl.

In additional embodiments, wherein $Ar^1$ is moiety having a structure represented by a formula:

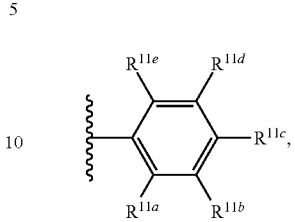

wherein at least two of $R^{11a}$, $R^{11b}$, $R^{11c}$, $R^{11d}$, and $R^{11e}$ are not hydrogen; and wherein each of $R^{11a}$, $R^{11b}$, $R^{11c}$, $R^{11d}$, and $R^{11e}$ is independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —$NH_2$, —NH(C1-C4 alkyl), and —N(C1-C4 alkyl$)_2$, —C(O)$R^{12}$, —C(O)O$R^{12}$, —C(O)NH$R^{12}$, —OC(O)$R^{12}$, —NHC(O)$R^{12}$, and —NHC(O)O$R^{12}$, wherein $R^{12}$ is hydrogen, methyl, ethyl, propyl, butyl, pentyl, or hexyl In further embodiments, $Ar^1$ is moiety having a structure represented by a formula:

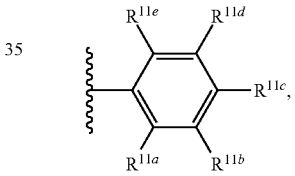

wherein at least three of $R^{11a}$, $R^{11b}$, $R^{11c}$, $R^{11d}$, and $R^{11e}$ are not hydrogen; and wherein each of $R^{11a}$, $R^{11b}$, $R^{11c}$, $R^{11d}$, and $R^{11e}$ is independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —$NH_2$, —NH(C1-C4 alkyl), and —N(C1-C4 alkyl$)_2$, —C(O)$R^{12}$, —C(O)O$R^{12}$, —C(O)NH$R^{12}$, —OC(O)$R^{12}$, —NHC(O)$R^{12}$, and —NHC(O)O$R^{12}$, wherein $R^{12}$ is hydrogen, methyl, ethyl, propyl, butyl, pentyl, or hexyl.

In more specific embodiments, $Ar^1$ is naphthyl or phenyl substituted with one or more of chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, and butoxy. In further embodiments, $Ar^1$ is naphthyl or phenyl substituted with one or more of chloro, methyl, methoxy, ethyl, ethoxy and combinations thereof.

The compounds as described are monophosphoramidites in which (c)(i) $R^2$ is selected from hydrogen and a hydroxyl protecting group and $R^3$ is a moiety having a structure represented by formula (II):

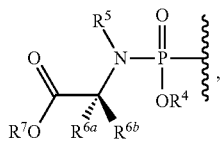

(II)

or are mono-cyclicphosphotriesters in which $R^2$ and $R^3$ together comprise a divalent moiety having a structure represented by formula (III):

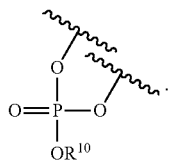

(III)

In specific embodiments, the compounds are monophosphoramidites in which (c)(i) $R^2$ is selected from hydrogen and a hydroxyl protecting group and $R^3$ is a moiety having a structure represented by formula (II). In more specific embodiments thereof, $R^2$ is hydrogen, $R^4$ is optionally substituted phenyl, C1-C6 alkyl, C2-C8 alkenyl, C2-C8 alkynyl, C3-C8 cycloalkyl, —(C1-C6 alkyl)-(C3-C8 cycloalkyl), and —(C1-C6 alkyl)-$Ar^2$, more specifically, phenyl or alkyl phenyl, $R^5$ is hydrogen, $R^{6a}$ is C1-C6 alkyl, C1-C6 monohaloalkyl, or C1-C6 polyhaloalkyl, $R^{6b}$ is hydrogen, and $R^7$ is C1-C6 alkyl, C1-C6 monohaloalkyl, or C1-C6 polyhaloalkyl. In yet more specific embodiments thereof, $R^{6a}$ is C1-C6 alkyl, and $R^7$ is C1-C6 alkyl.

Specific examples of the described compounds of the invention include, but are not limited to, those having a structure selected from the following, or a pharmaceutically acceptable salt, hydrate, solvate, or polymorph thereof:

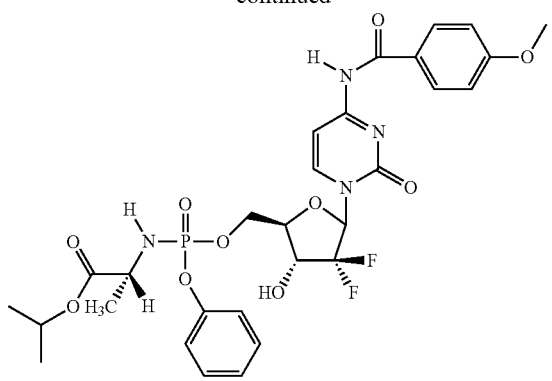

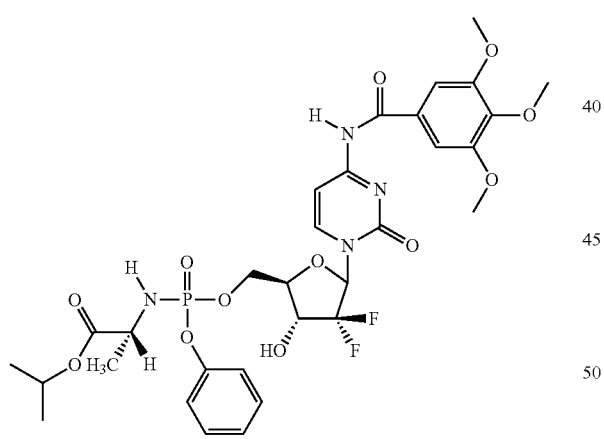

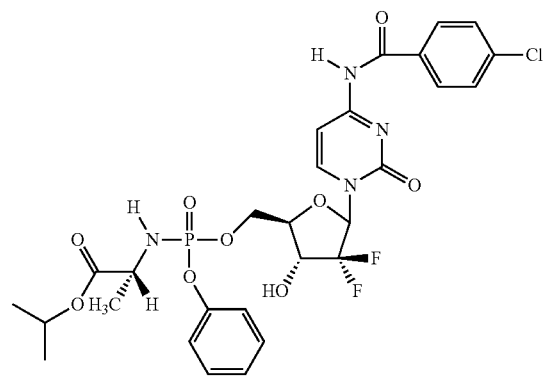

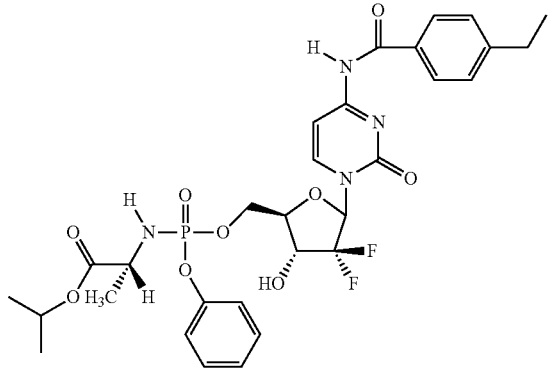

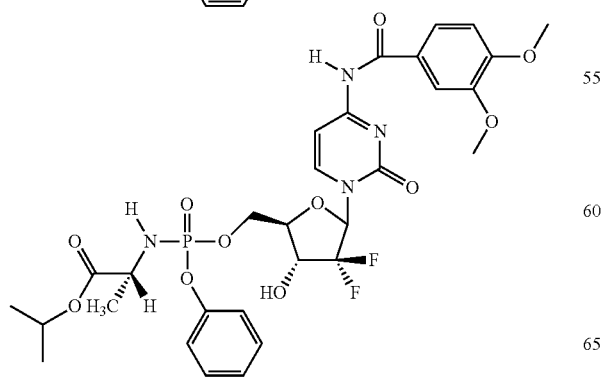

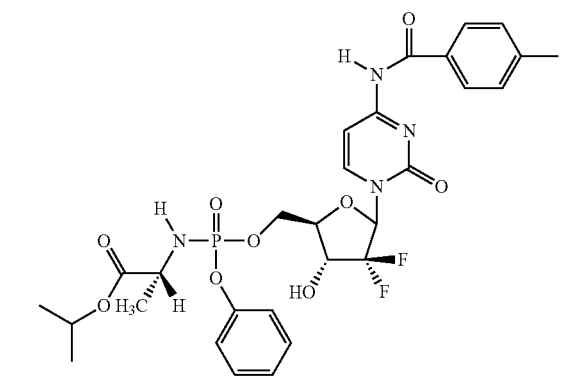

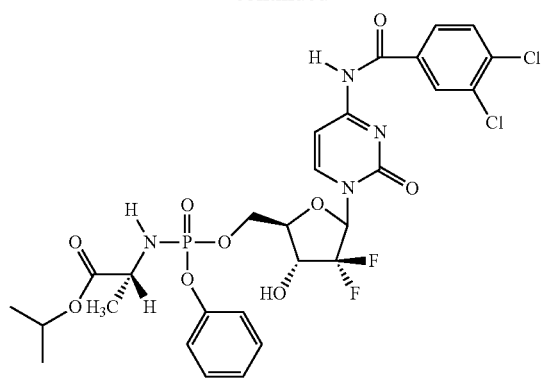
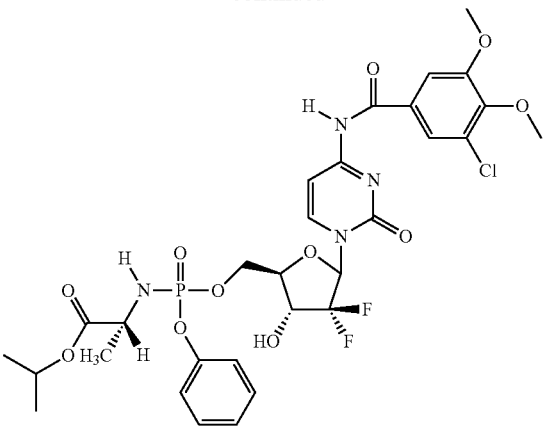
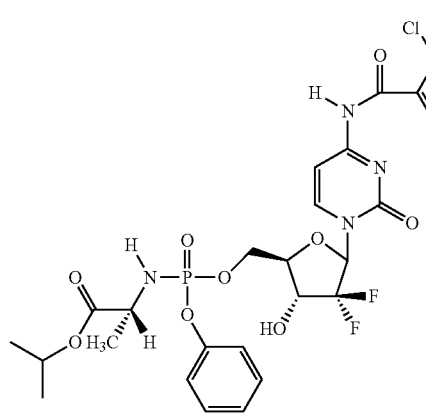
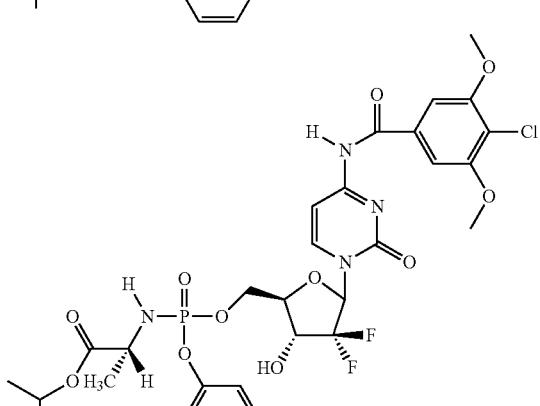
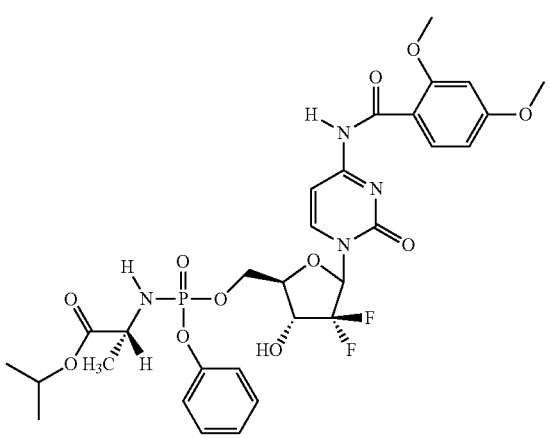
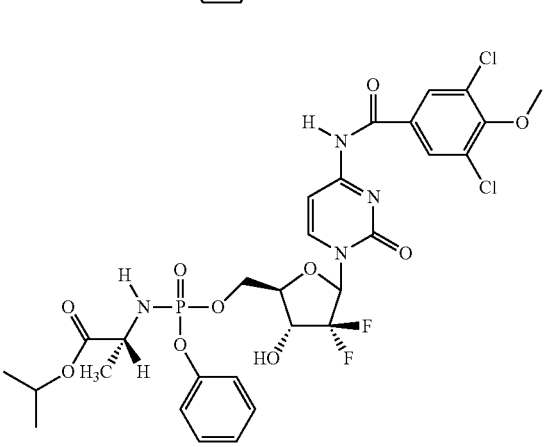
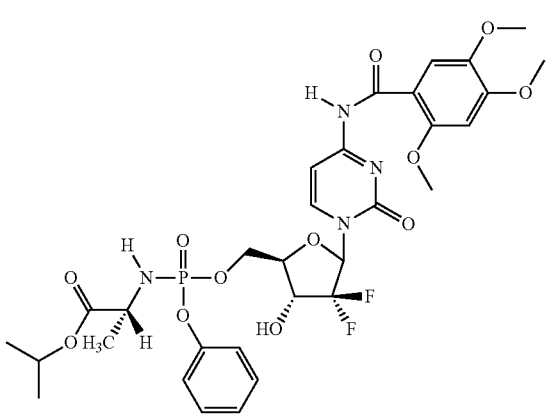
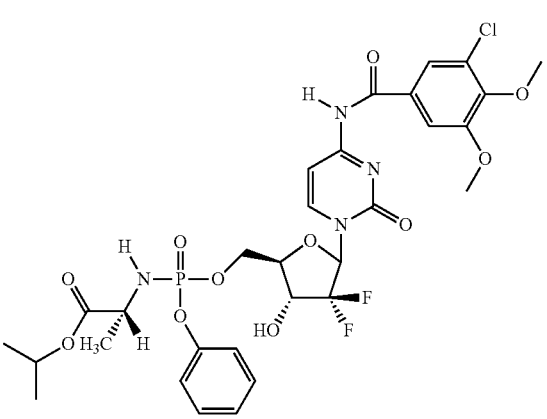

31
-continued
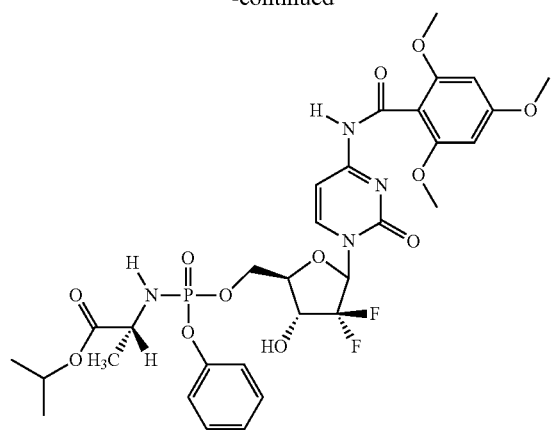
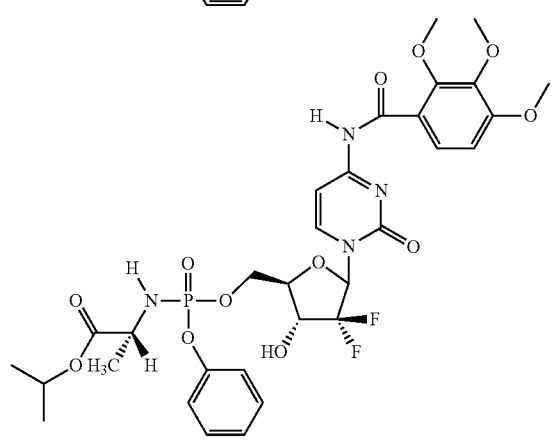
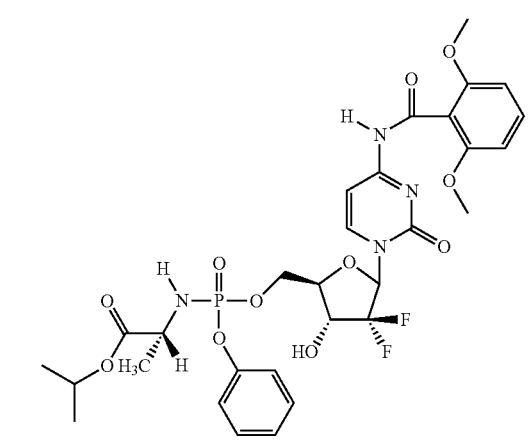
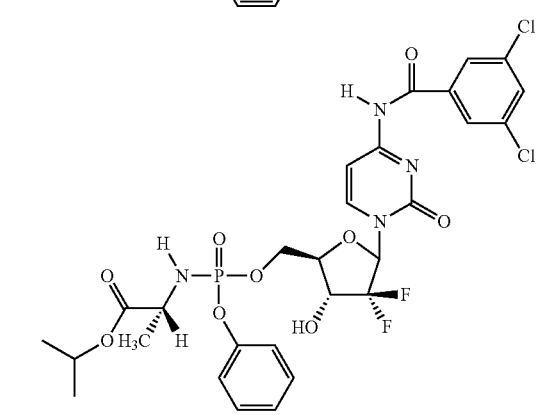
32
-continued
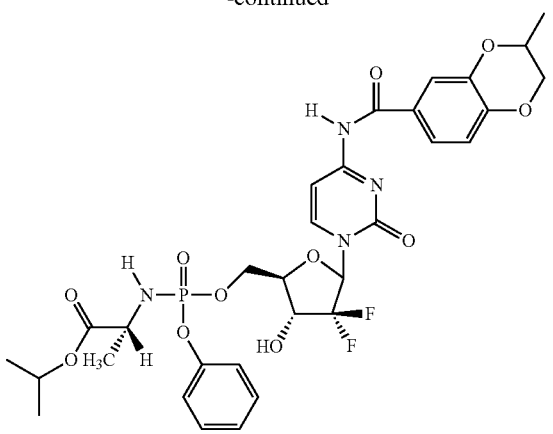
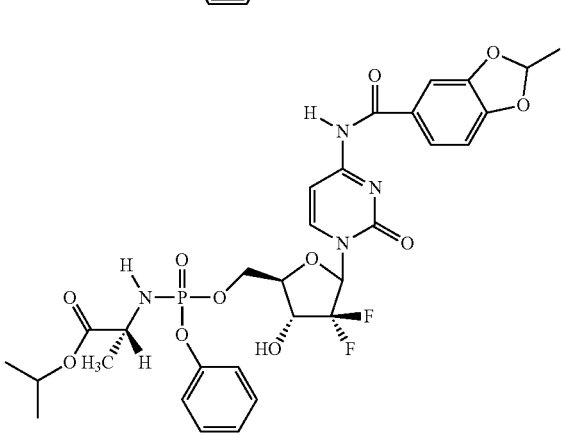
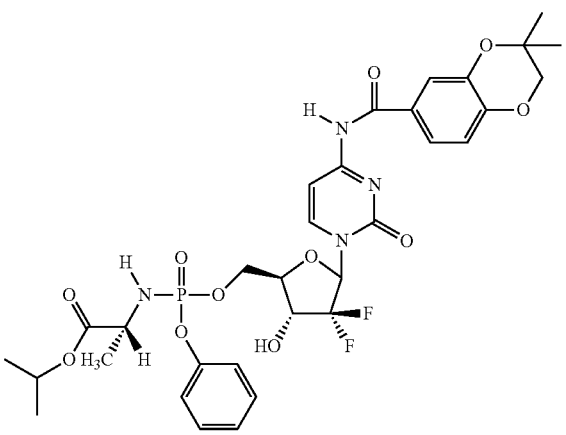
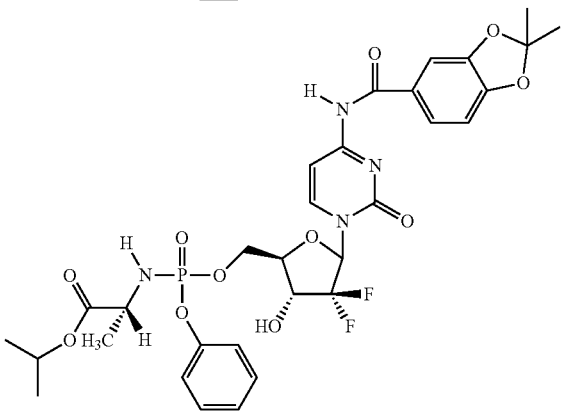

-continued
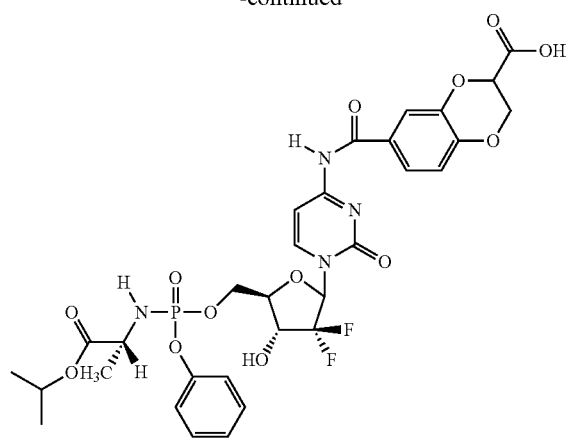
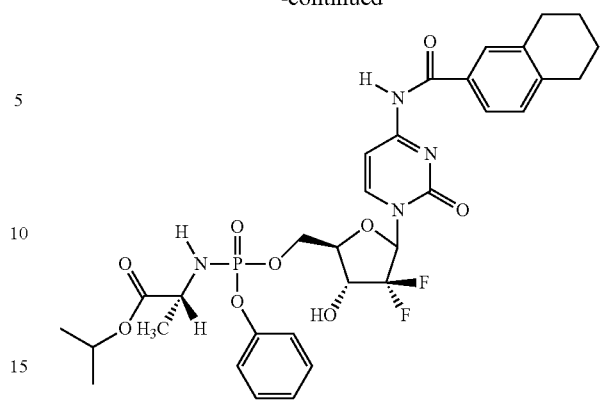
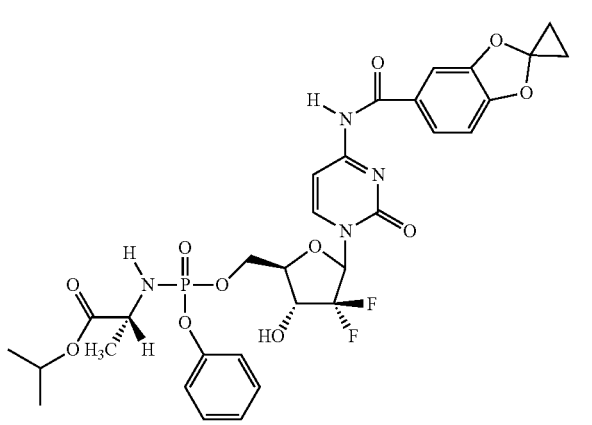
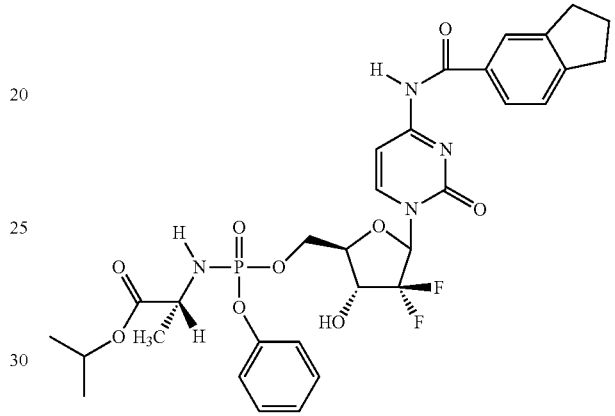
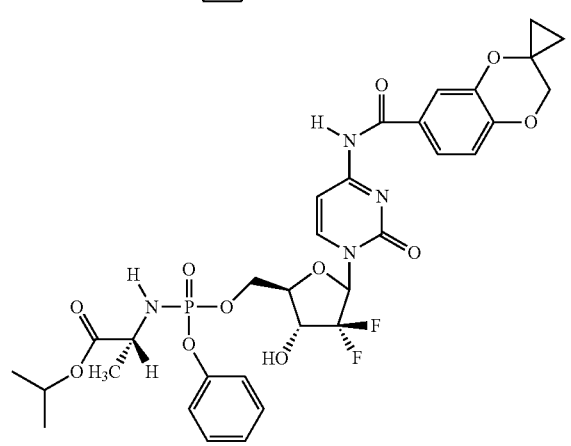
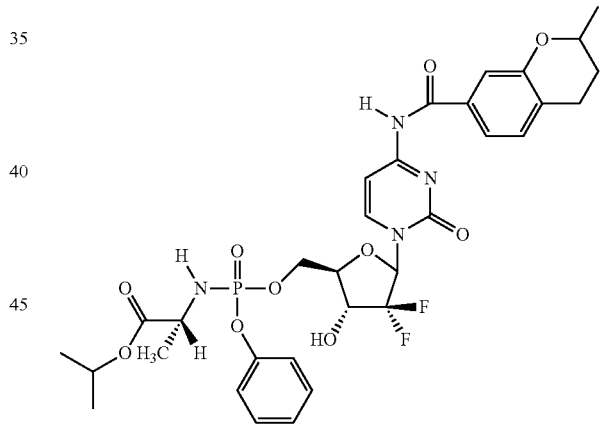
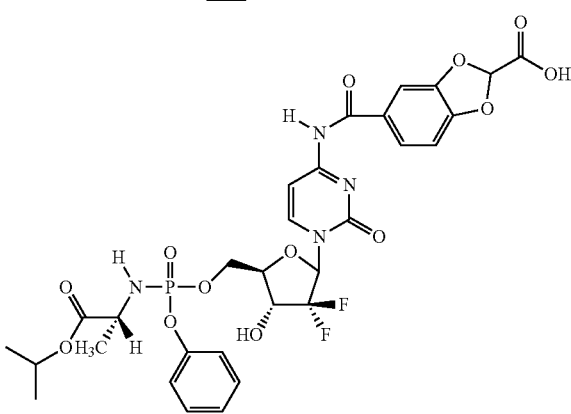
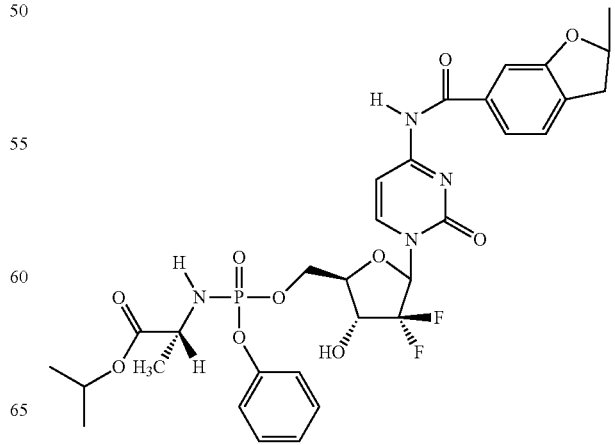

35
-continued
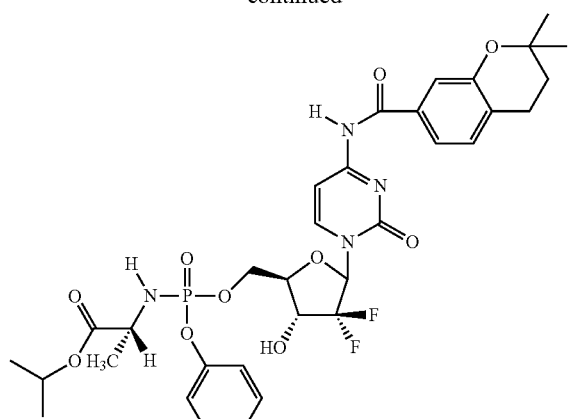
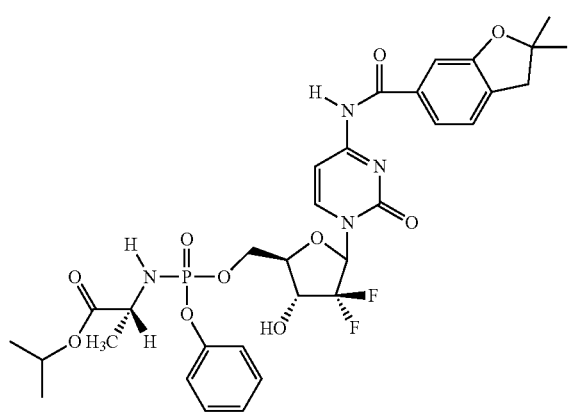
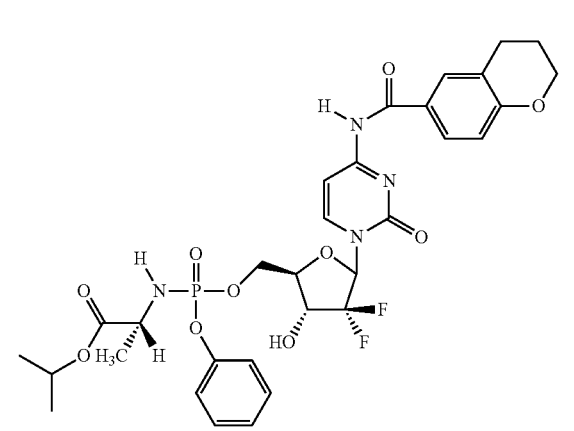
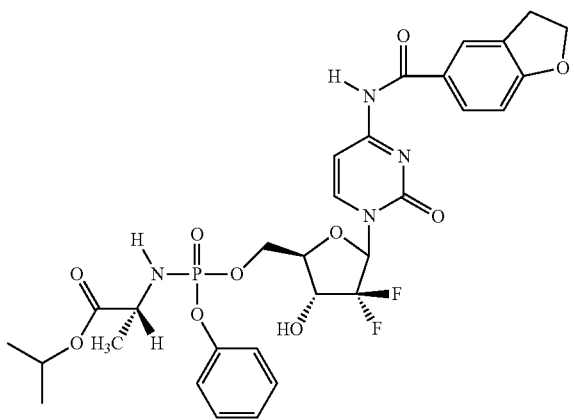
36
-continued
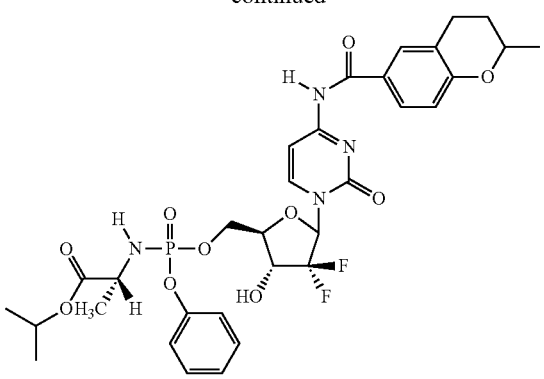
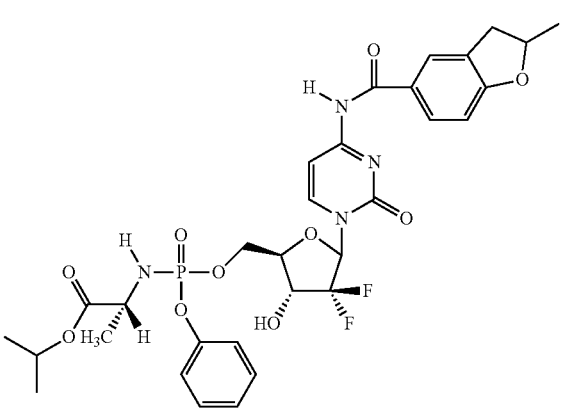
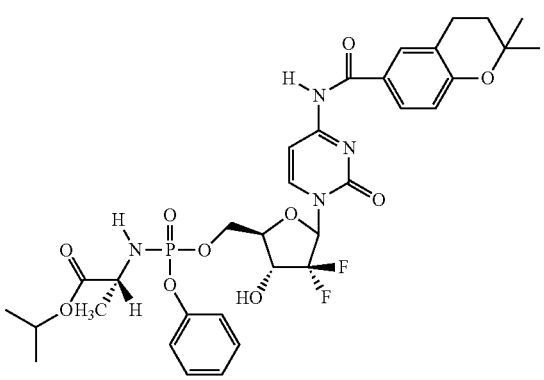
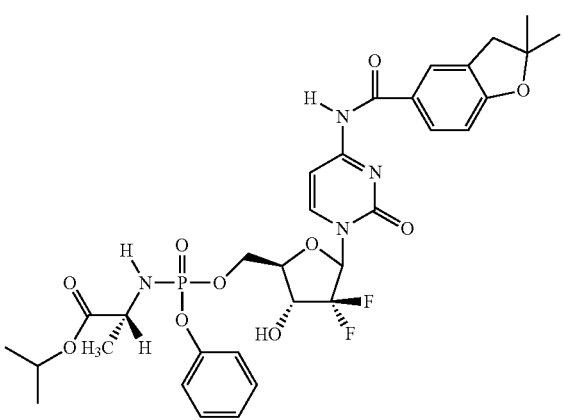

37
-continued
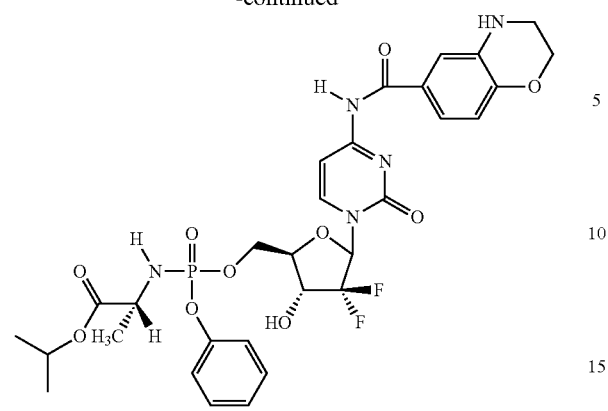
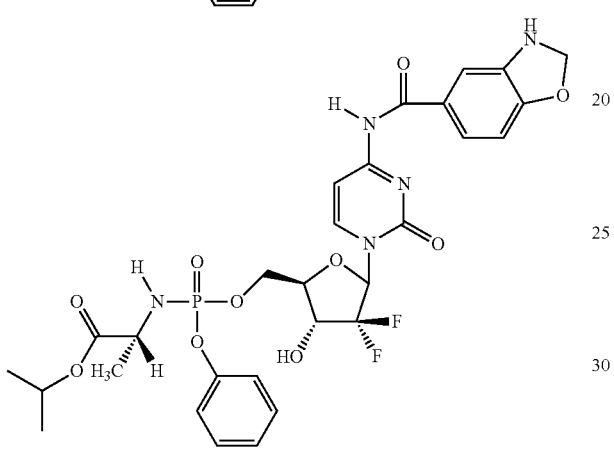
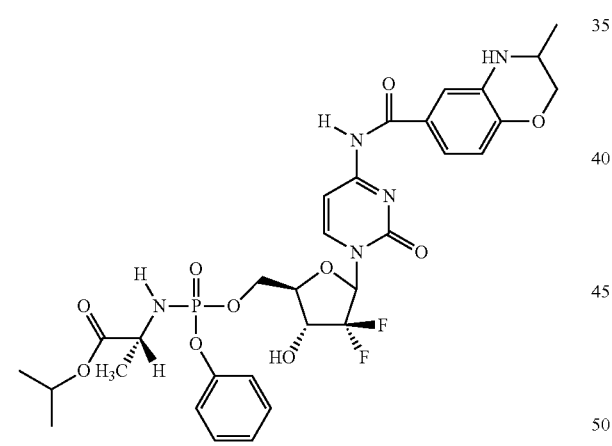
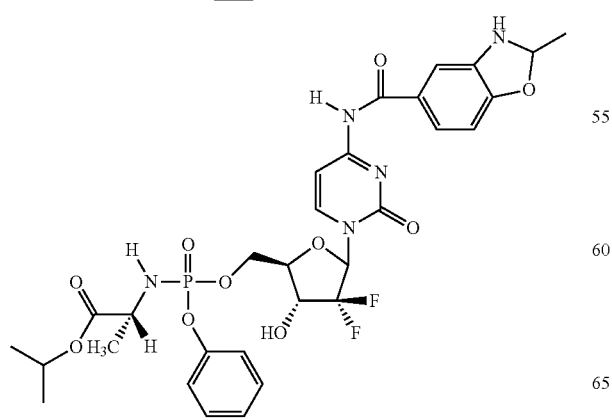
38
-continued
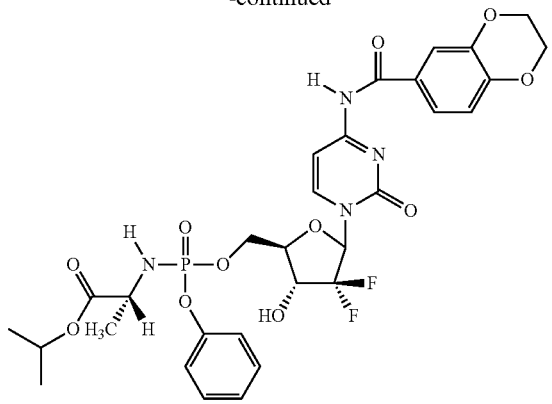
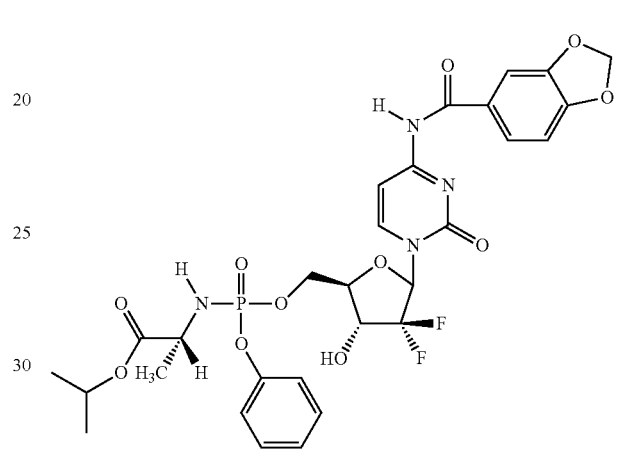
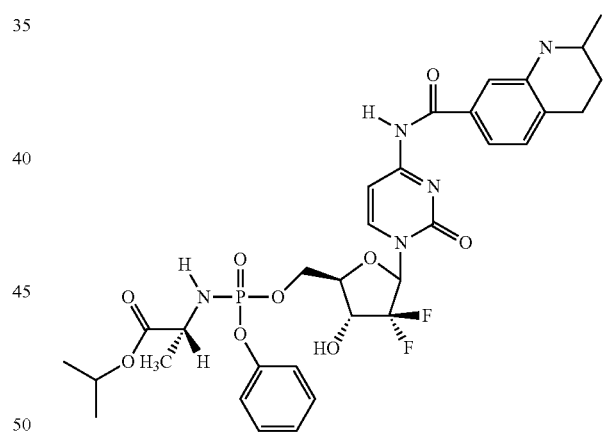
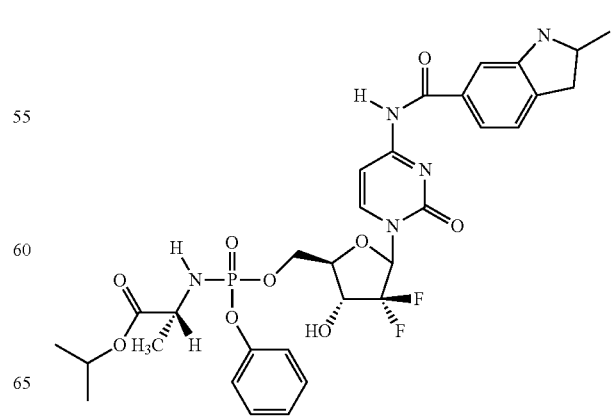

39
-continued
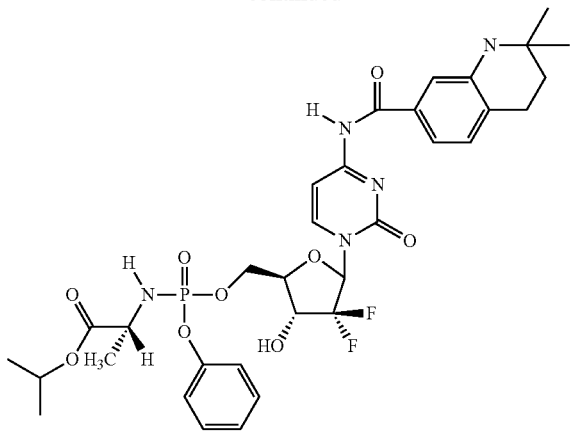
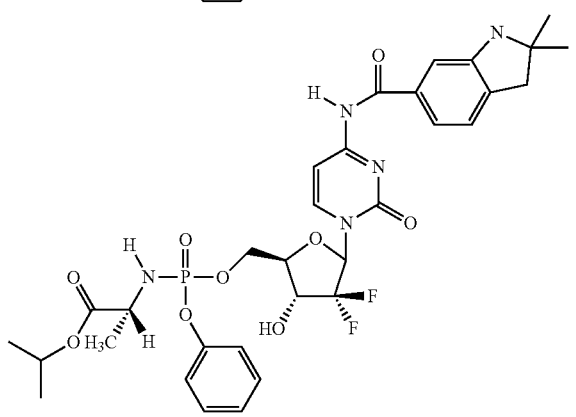
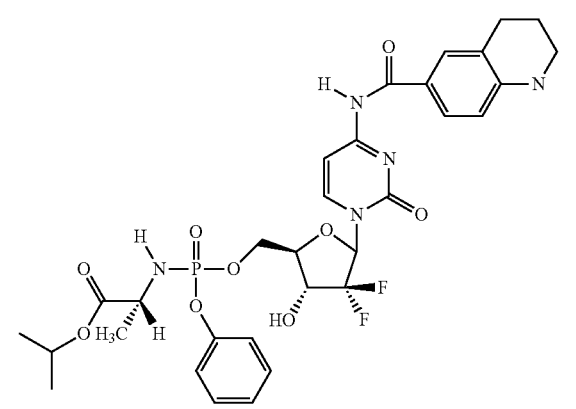
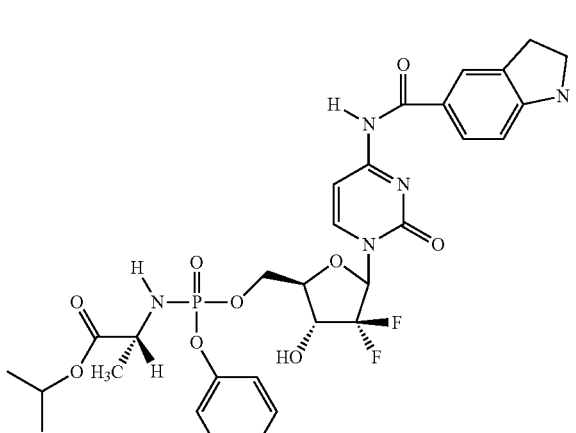
40
-continued
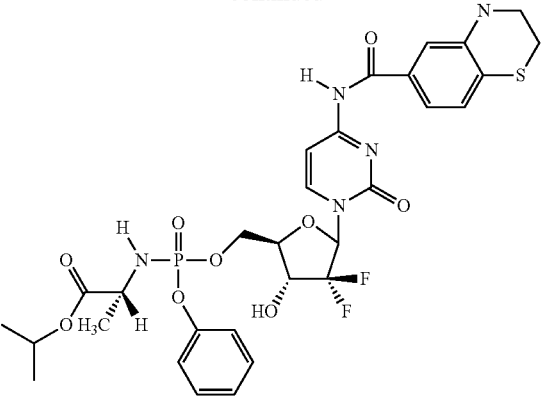
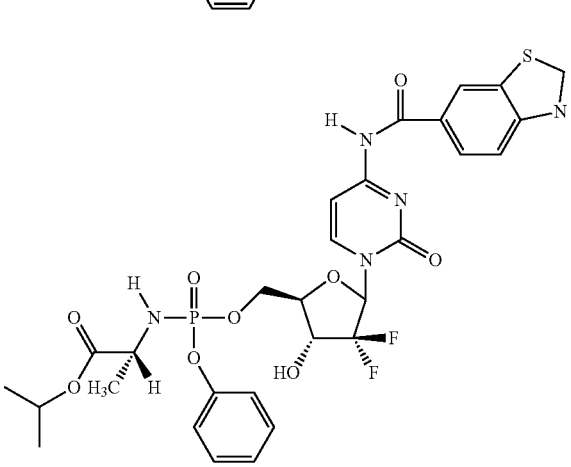
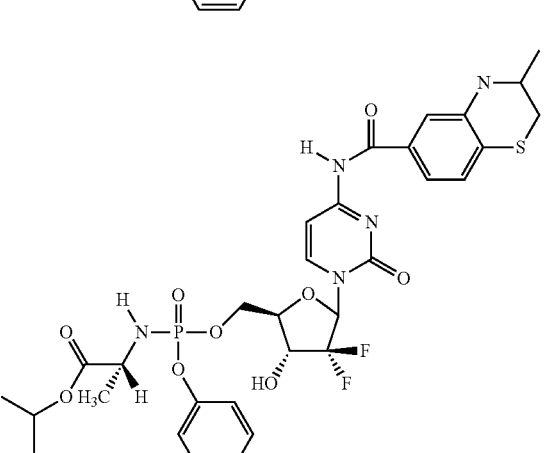
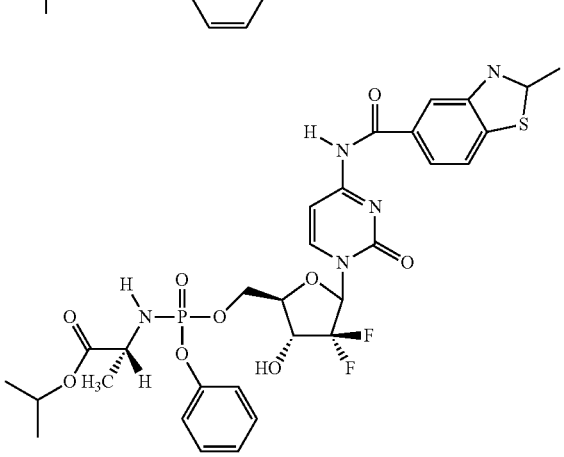

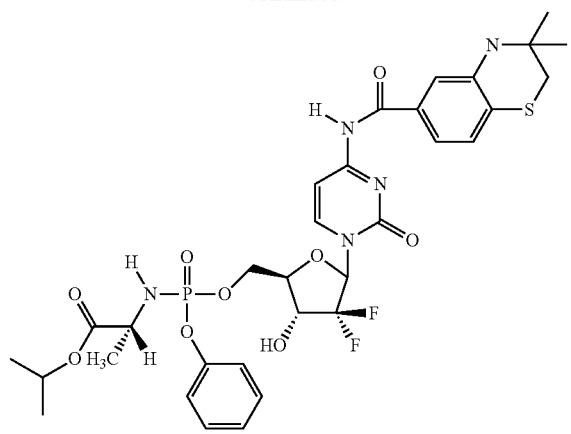
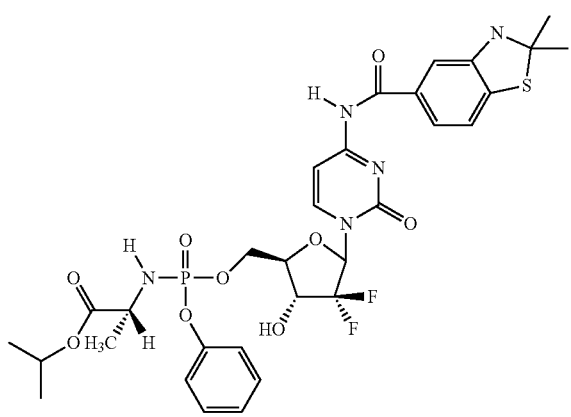
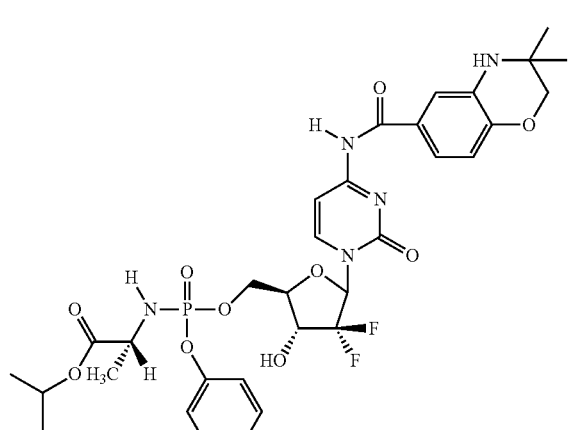
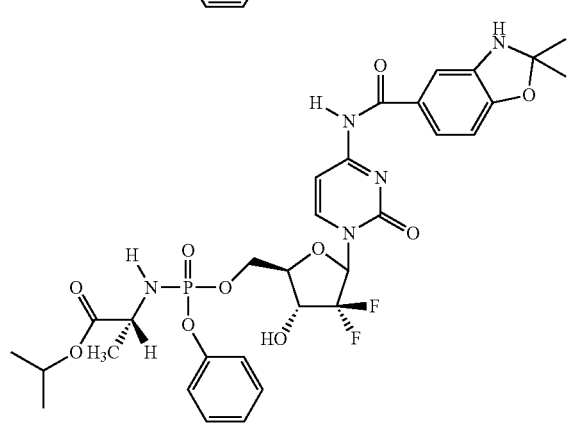
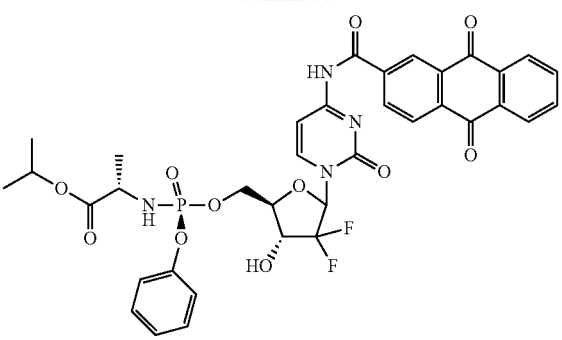
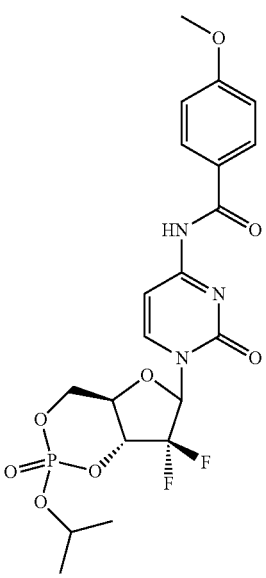
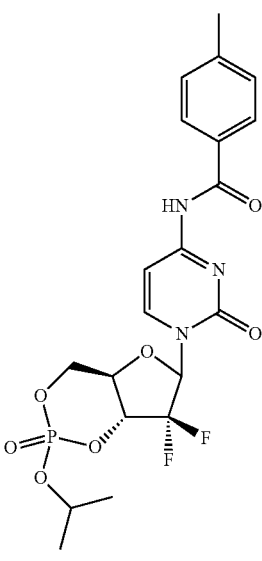

43
-continued
44
-continued
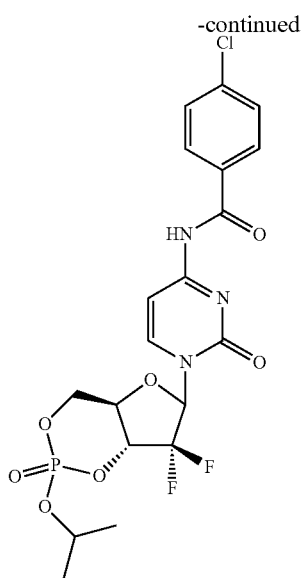
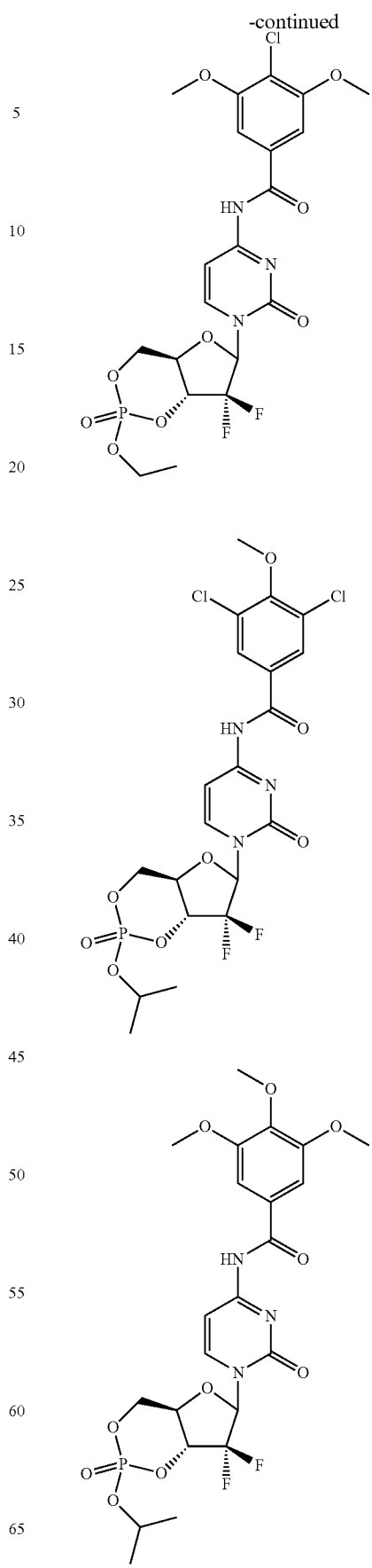

45
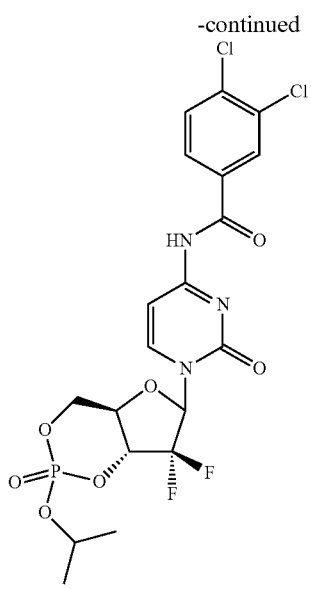
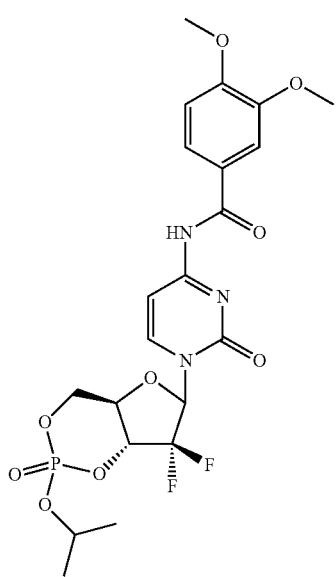
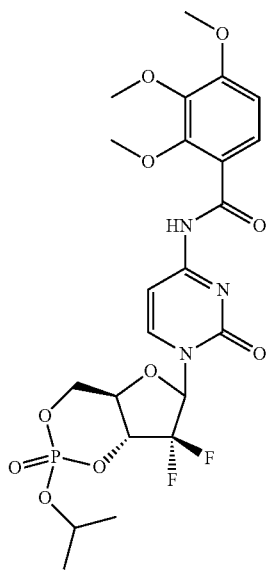
46
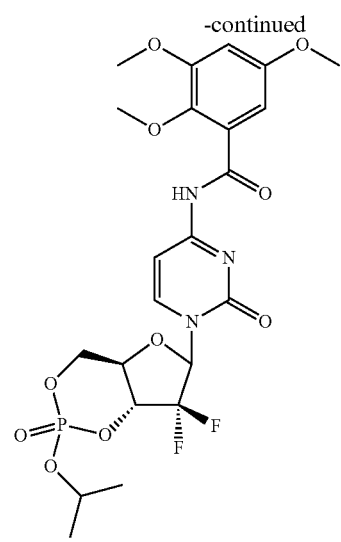
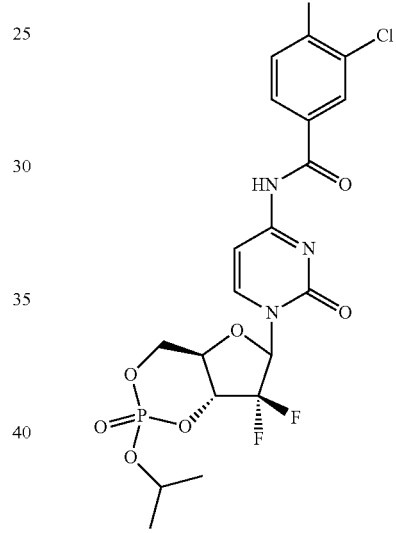
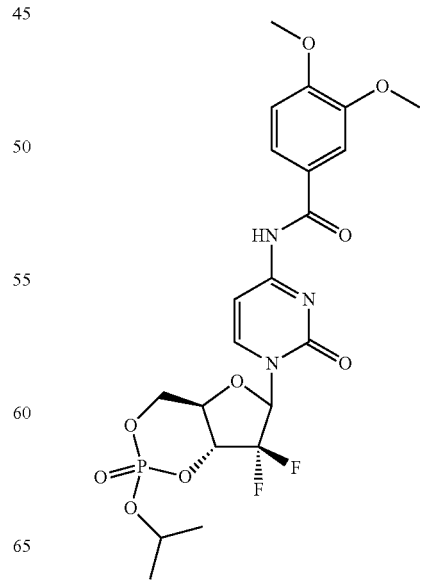

47
-continued
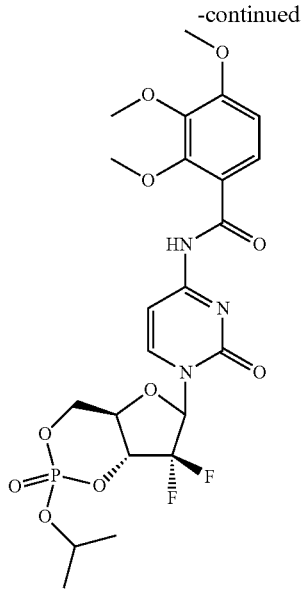
48
-continued
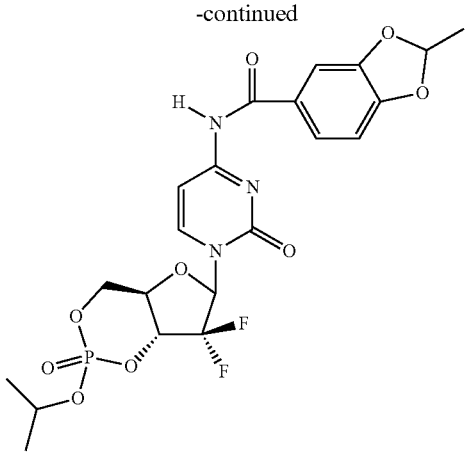
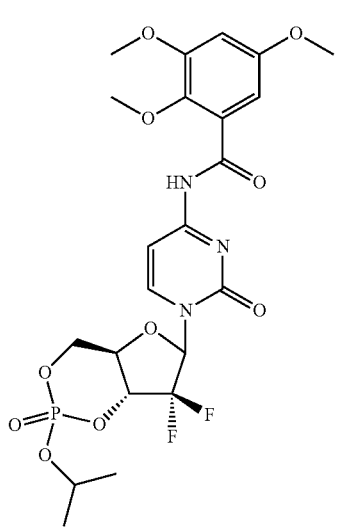
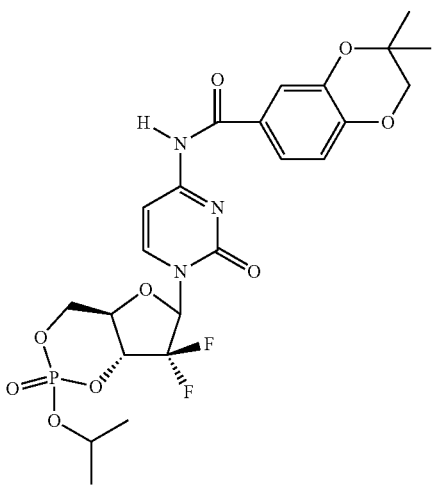
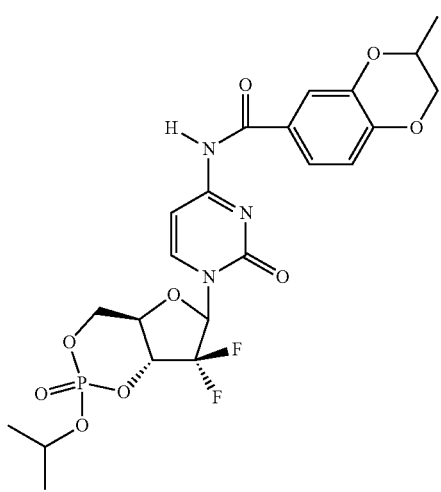
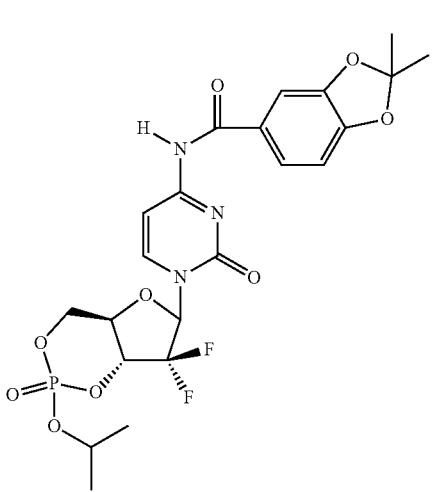

49
-continued
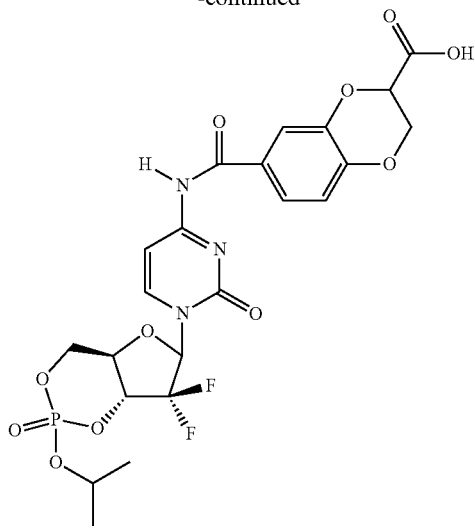
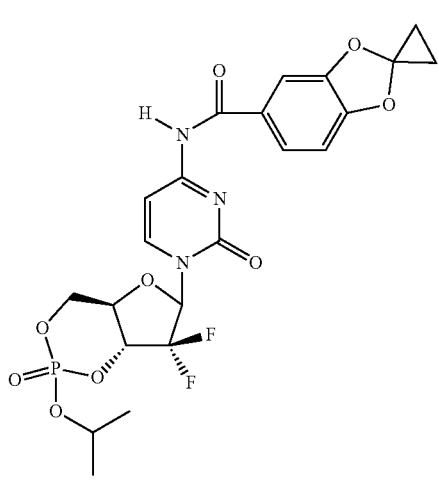
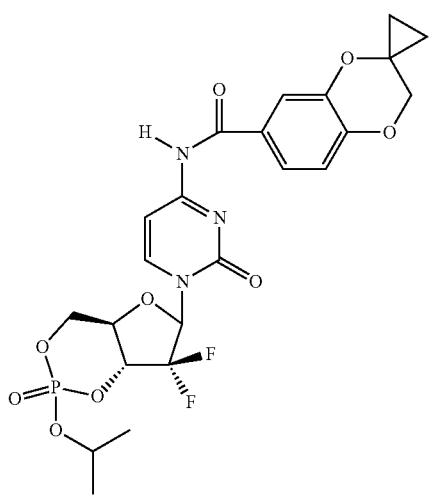
50
-continued
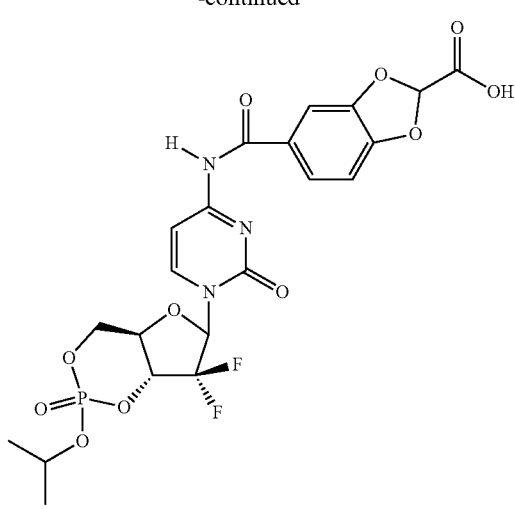
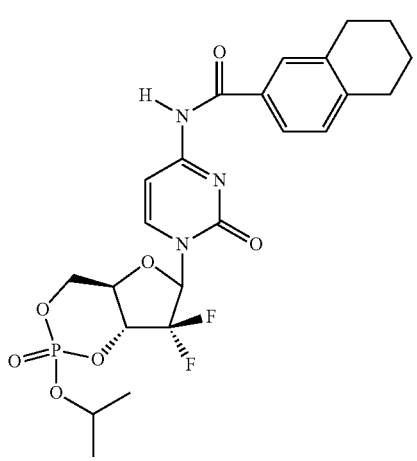
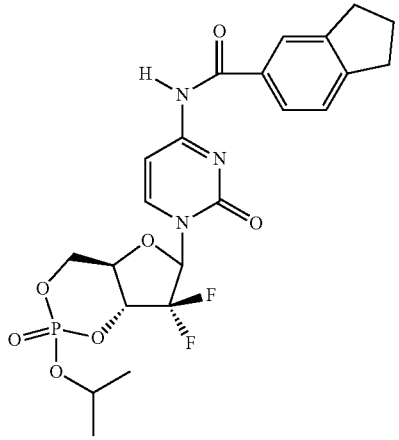

51
-continued
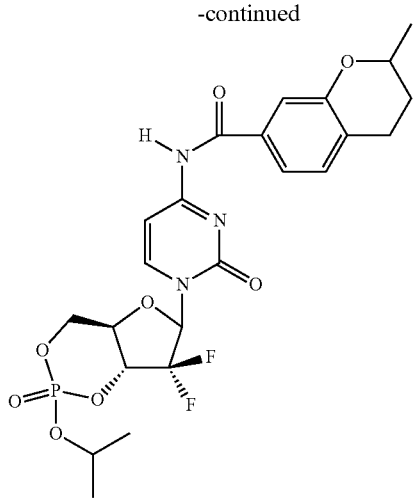
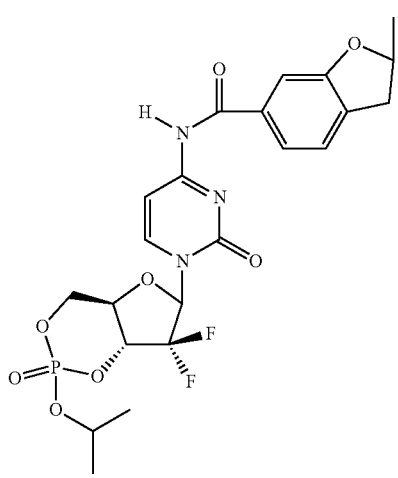
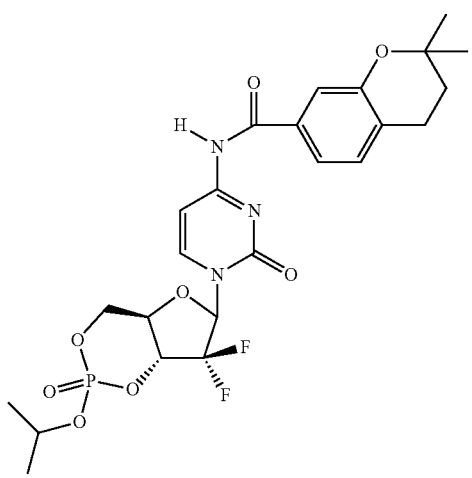
52
-continued
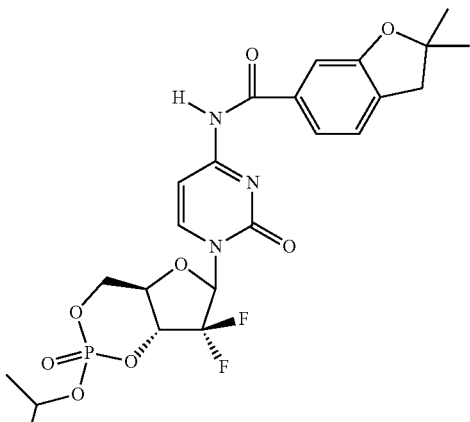
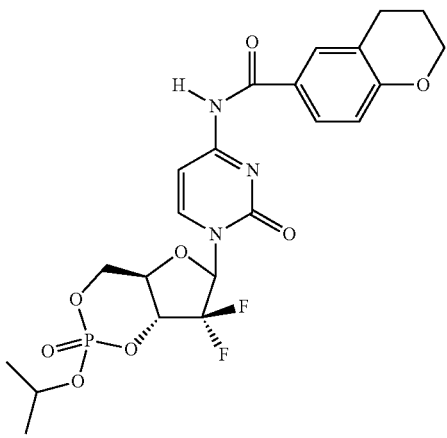
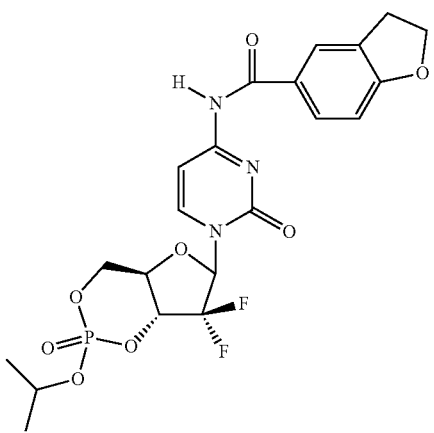

53
-continued
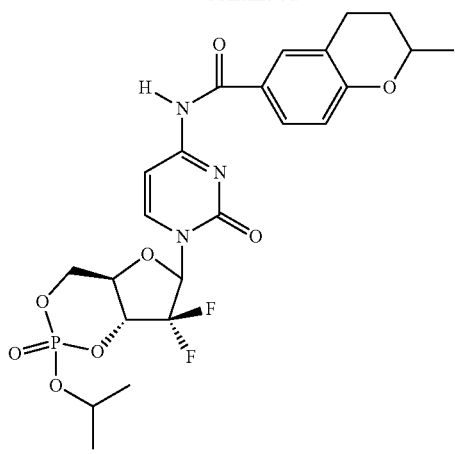
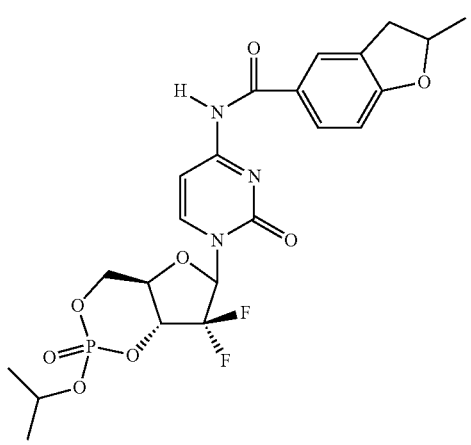
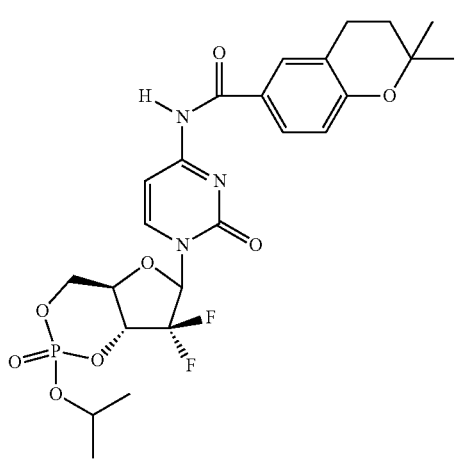
54
-continued
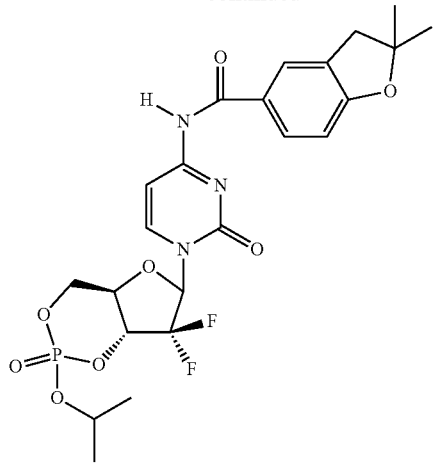
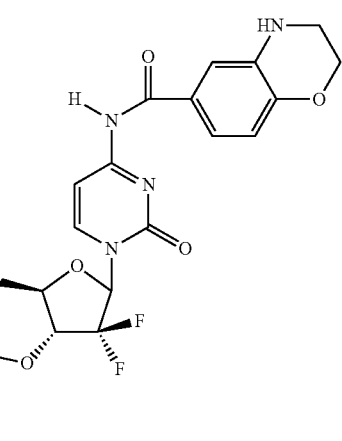
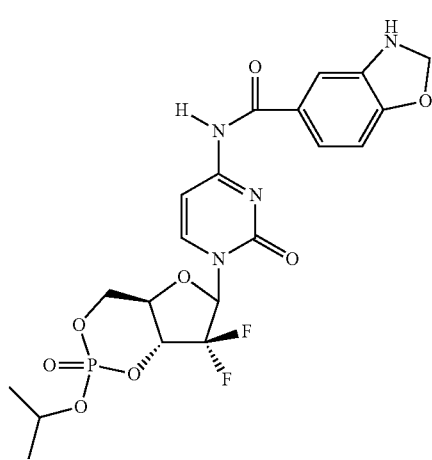

-continued
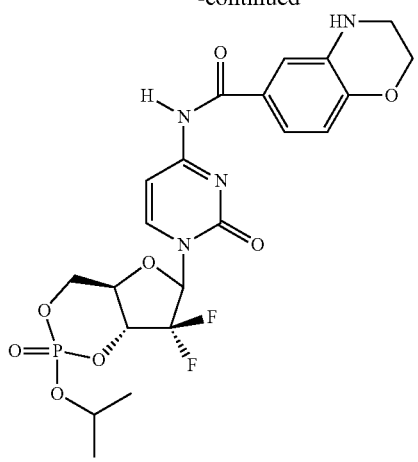
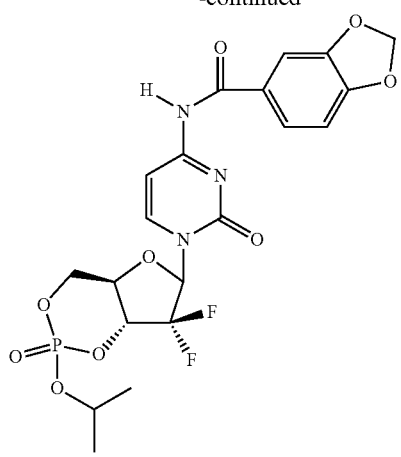
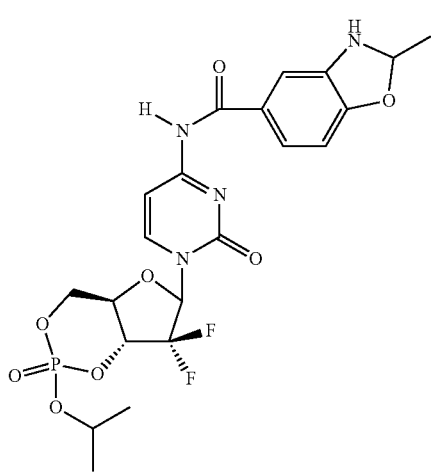
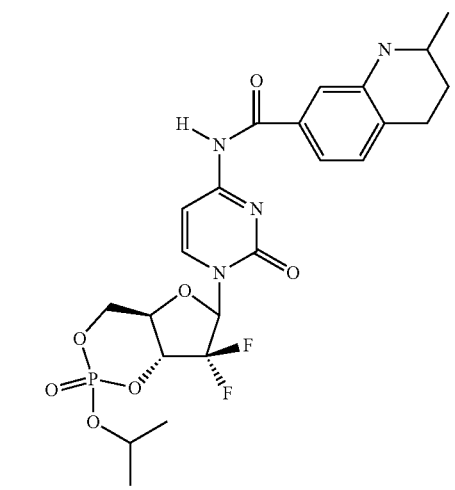
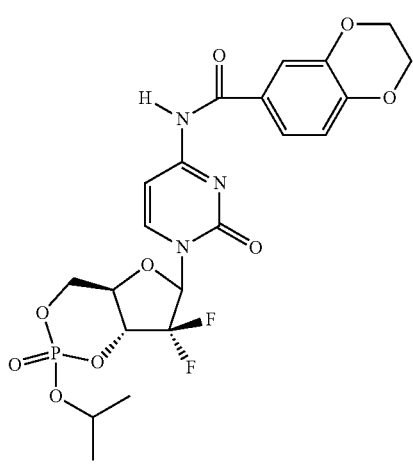
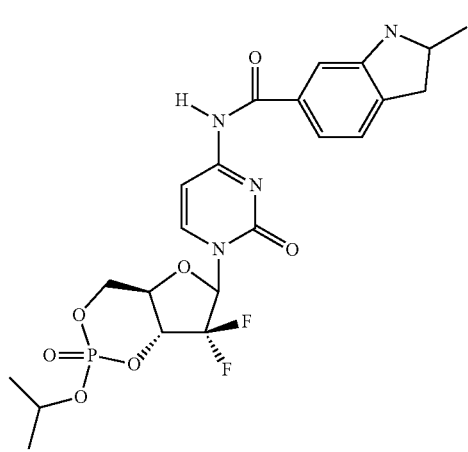

57
-continued
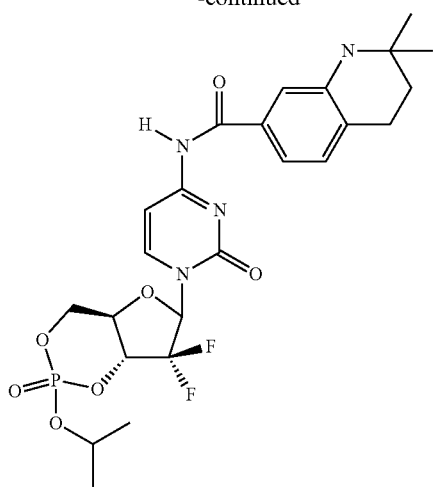
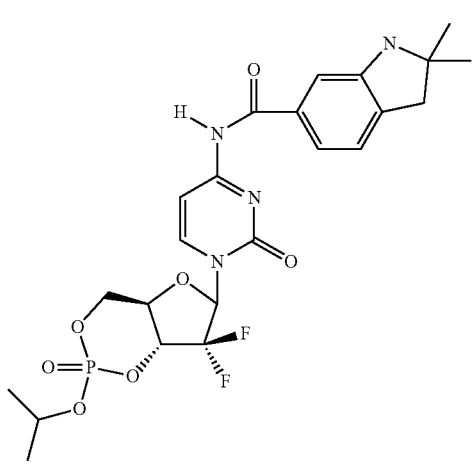
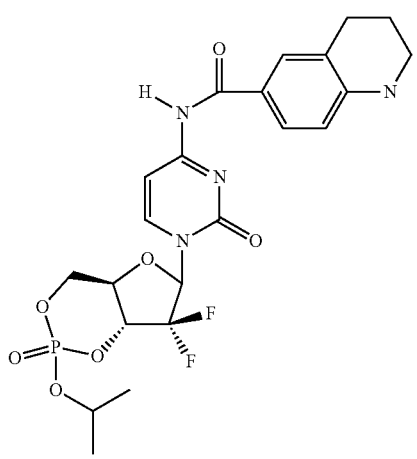
58
-continued
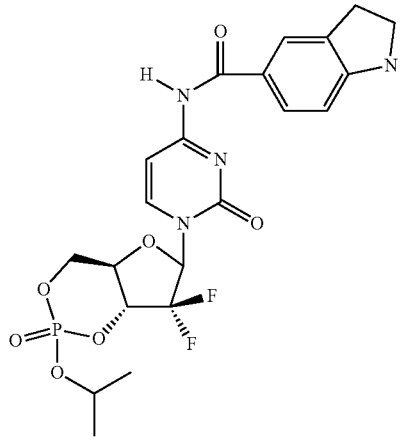
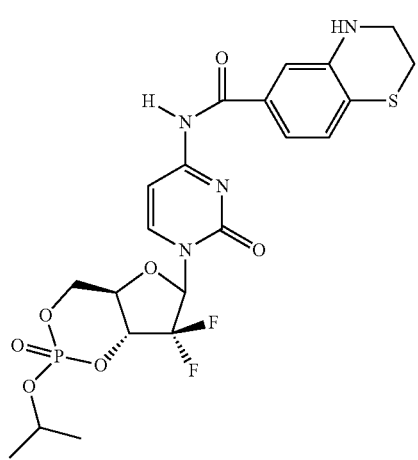
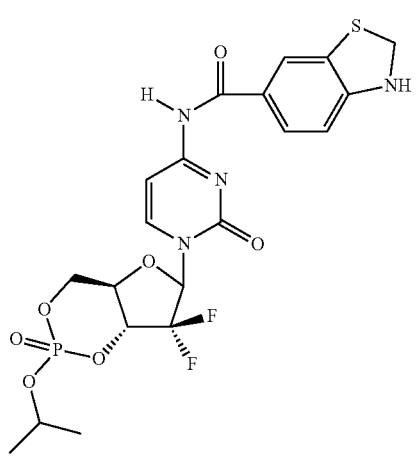

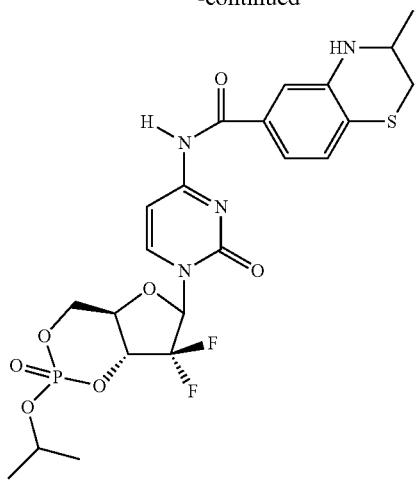
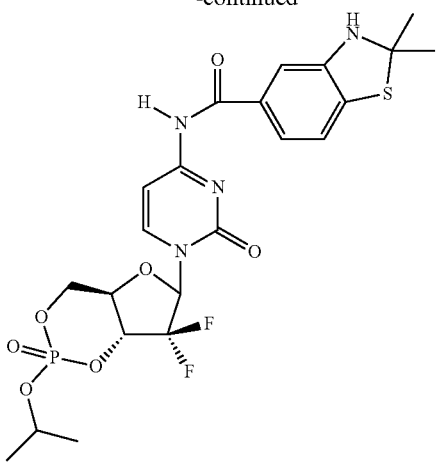
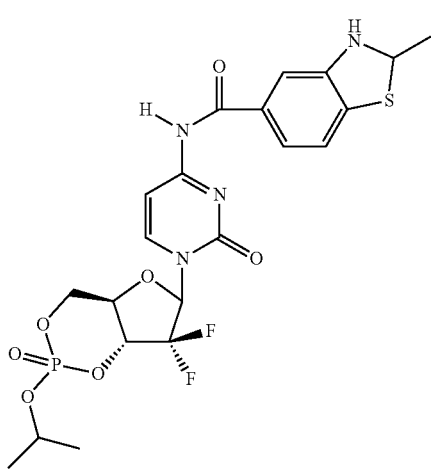
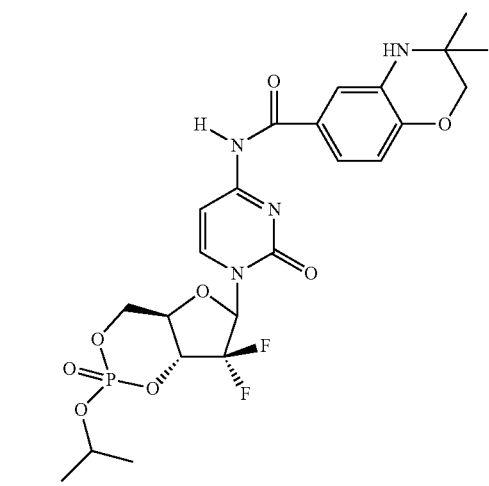
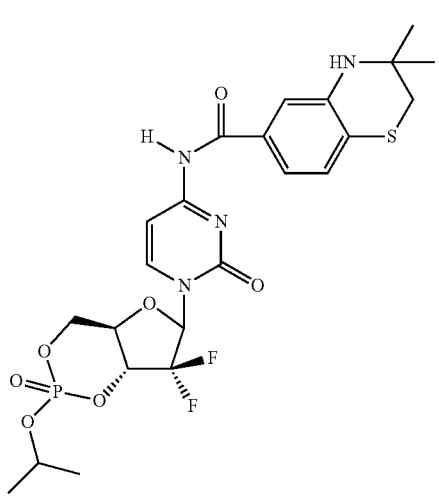
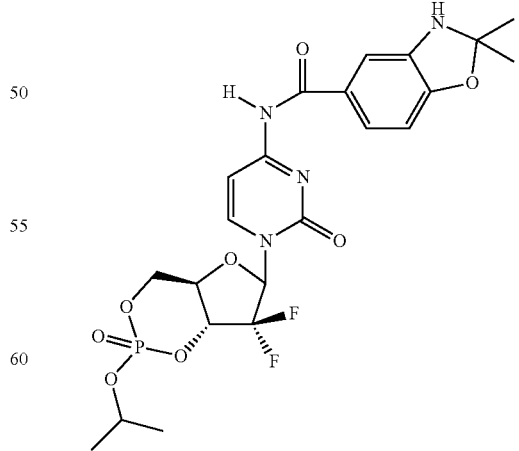
In another embodiment, the invention is directed to compounds of formula (IV):

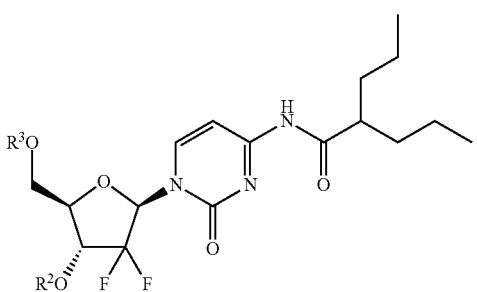

(IV)

wherein (i) $R^2$ is selected from hydrogen and a hydroxyl protecting group and $R^3$ is a moiety having a structure represented by formula (II):

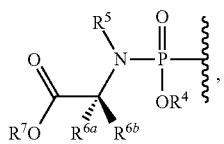

(II)

wherein $R^4$ is selected from C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, $Ar^2$, —(C1-C6 alkyl)-(C3-C8 cycloalkyl), —(C1-C6 alkyl)-(C2-C8 heterocycloalkyl), and —(C1-C6 alkyl)-$Ar^2$;

wherein $R^5$ is selected from hydrogen, C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, $Ar^2$, —(C1-C6 alkyl)-(C3-C8 cycloalkyl), —(C1-C6 alkyl)-(C2-C8 heterocycloalkyl), and —(C1-C6 alkyl)-$Ar^2$;

wherein each of $R^{6a}$ and $R^{6b}$ is selected from hydrogen, C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, $Ar^2$, —(C1-C6 alkyl)-(C3-C8 cycloalkyl), —(C1-C6 alkyl)-(C2-C8 heterocycloalkyl), and —(C1-C6 alkyl)-$Ar^2$, provided that each of $R^{6a}$ and $R^{6b}$ are not the same; and wherein $R^7$ is selected from C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, $Ar^2$, —(C1-C6 alkyl)-(C3-C8 cycloalkyl), —(C1-C6 alkyl)-(C2-C8 heterocycloalkyl), and —(C1-C6 alkyl)-$Ar^2$;

in which $Ar^2$ is an optionally substituted phenyl, naphthalene, monocyclic heteroaryl, bicyclic heteroaryl or polycyclic heteroaryl; or (ii) $R^2$ and $R^3$ together comprise a divalent moiety having a structure represented by formula (III):

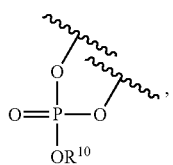

(III)

wherein $R^{10}$ is selected from hydrogen, C1-C6 alkyl, C1-C6 monohaloalkyl, C1-C6 polyhaloalkyl, C2-C8 alkenyl, C2-C8 alkynyl, C3-C8 cycloalkyl, C2-C8 heterocycloalkyl, $Ar^2$, —(C1-C6 alkyl)-(C3-C8 cycloalkyl), —(C1-C6 alkyl)-(C2-C8 heterocycloalkyl), —(C1-C6 alkyl)-$Ar^2$, in which $Ar^2$ is as defined above;

or a pharmaceutically acceptable salt, hydrate, solvate, or polymorph thereof.

In specific embodiments, the compounds are monophosphoramidites in which (c)(i) $R^2$ is selected from hydrogen and a hydroxyl protecting group and $R^3$ is a moiety having a structure represented by formula (II). In more specific embodiments thereof, $R^2$ is hydrogen, $R^4$ is optionally substituted phenyl, C1-C6 alkyl, C2-C8 alkenyl, C2-C8 alkynyl, C3-C8 cycloalkyl, —(C1-C6 alkyl)-(C3-C8 cycloalkyl), and —(C1-C6 alkyl)-$Ar^2$, more specifically, phenyl or alkyl phenyl, $R^5$ is hydrogen, $R^{6a}$ is C1-C6 alkyl, C1-C6 monohaloalkyl, or C1-C6 polyhaloalkyl, $R^{6b}$ is hydrogen, and $R^7$ is C1-C6 alkyl, C1-C6 monohaloalkyl, or C1-C6 polyhaloalkyl. In yet more specific embodiments thereof, $R^{6a}$ is C1-C6 alkyl, and $R^7$ is C1-C6 alkyl.

In a specific example, the compound is of formula (IV), wherein $R^4$ is phenyl or alkyl phenyl, $R^5$ is hydrogen, $R^{6a}$ is CH3, $R^{6b}$ is hydrogen, and $R^7$ is isopropyl, or is a pharmaceutically acceptable salt, hydrate, solvate, or polymorph thereof.

In yet another embodiment, the invention is directed to a compound of formula (V):

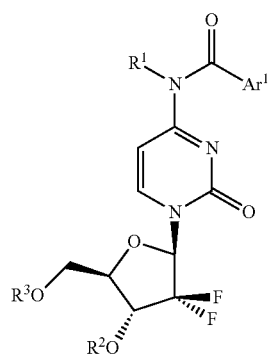

(V)

(a) wherein $Ar^1$ is naphthyl or is a bicyclic or polycyclic fused ring system comprising an aryl ring fused to one or more 4-, 5-, 6-, 7-, or 8-membered cycloalkyl, wherein the aryl ring of the bicyclic or polycyclic fused ring system is selected from phenyl, pyridinyl, pyrimidinyl, pyridazinyl, pyrazinyl, and triazinyl;

wherein the naphthyl or the aryl ring of the bicyclic or polycyclic fused ring system is optionally substituted with 1, 2, or 3 groups independently selected from halogen, —OH, —CN, —NH$_2$, thiol, C1-C6 alkyl, C1-C6 alkoxy, C1-C6 monohaloalkyl, C1-C6 polyhaloalkyl, C1-C6 alkylamino, and C1-C6 dialkylamino;

wherein the cycloalkyl of the bicyclic or polycyclic fused ring system is optionally substituted with 1, 2, 3, 4, or 5 groups independently selected from halogen, —OH, —CN, —NH$_2$, thiol, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)OR$^8$, and —(C=O)NR$^{9a}$R$^{9b}$, in which each R$^8$ is independently selected from hydrogen, C1-C6 alkyl, and a hydroxyl protecting group, and each of R$^{9a}$ and R$^{9b}$ is independently selected from hydrogen, C1-C4 alkyl, and an amine protecting group;

(b) wherein R¹ is selected from hydrogen, C1-C4 alkyl, and an amine protecting group; and (c) wherein R² is selected from hydrogen, C1-C6 alkyl and a hydroxyl protecting group and R³ is selected from hydrogen and a hydroxyl protecting group, or a pharmaceutically acceptable salt, hydrate, solvate, or polymorph thereof.

In specific embodiments of the compound of formula (V), the naphthyl or the aryl ring of the bicyclic or polycyclic fused ring system is optionally substituted with 1, 2, or 3 groups selected from chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, and butoxy. In further embodiments, the naphthyl or the aryl ring of the bicyclic or polycyclic fused ring system is substituted with one or more of chloro, methyl, methoxy, ethyl, ethoxy and combinations thereof.

Exemplary compounds of formula (V) include, but are not limited to, the following compounds:

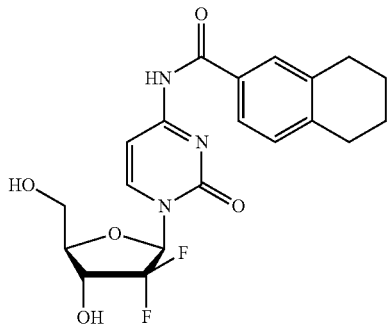

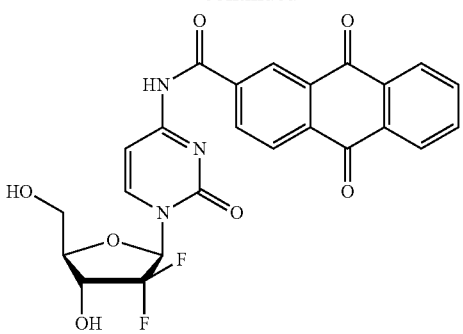

-continued

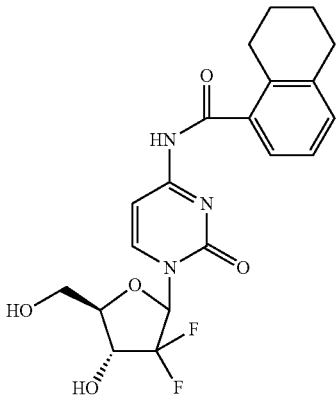

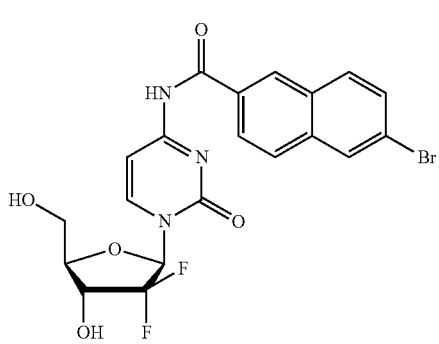

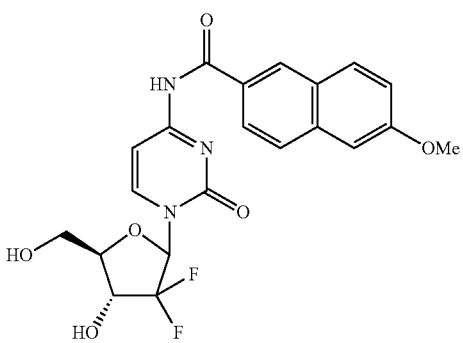

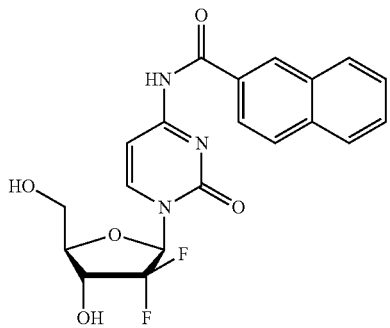

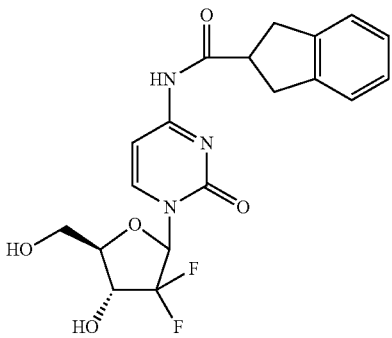

-continued

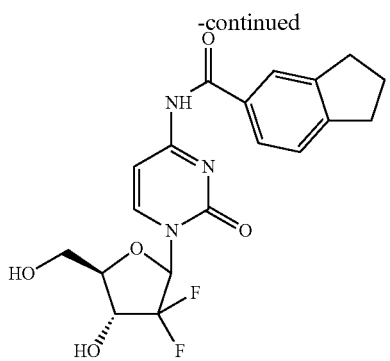

The gemcitabine analogs and monophosphorylated compounds of the present invention can be prepared by employing reactions as shown in the disclosed schemes, in addition to other standard manipulations that are known in the literature, exemplified in the experimental sections or clear to one skilled in the art. The following examples are provided so that the invention might be more fully understood, are illustrative only, and should not be construed as limiting. For clarity, examples having a fewer substituent can be shown where multiple substituents are allowed under the definitions disclosed herein. It is contemplated that each disclosed method can further comprise additional steps, manipulations, and/or components. It is also contemplated that any one or more step, manipulation, and/or component can be optionally omitted. It is understood that a disclosed method can be used to provide the disclosed compounds. It is also understood that the products of the disclosed methods can be employed in the disclosed compositions, kits, and uses.

Generally, according to one method, the gemcitabine analog compounds of the present invention are prepared by amidating the amine group of gemcitabine, and the monophosphorylated compounds are prepared by phosphorylating the resulting amide compound. Thus, according to one embodiment, a method of making the compounds of the invention comprises providing a first compound having a structure represented by the formula:

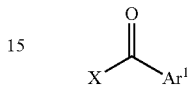

wherein $R^2$ is selected from hydrogen, C1-C4 alkyl, and amine protecting group; wherein $R^3$ is selected from hydrogen and hydroxyl protecting group; and wherein $R^4$ is selected from hydrogen, C1-C6 alkyl, and hydroxyl protecting group, or wherein $R^3$ and $R^4$ together comprise a divalent moiety having a structure represented by the formula:

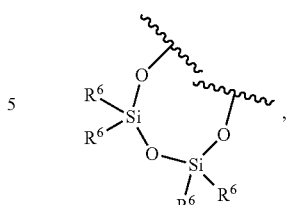

wherein each of $R^6$ is independently selected from methyl, ethyl, propyl, and butyl; and (b) reacting with a second compound having a structure represented by the formula:

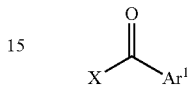

wherein X is halogen or pseudohalogen and $Ar^1$ is as defined above, thereby forming an amide bond.

More specifically, Gemcitabine can be treated with 1,3-dichloro-1,1,3,3-tetraisopropyldisiloxane (TIPDSiCl2) in dry pyridine to provide 4-amino-1-((6aR,8R,9aR)-9,9-difluoro-2,2,4,4-tetraisopropyltetrahydro-6H-furo[3,2-f][1,3,5,2,4]trioxadisilocin-8-yl)pyrimidin-2(1H)-one:

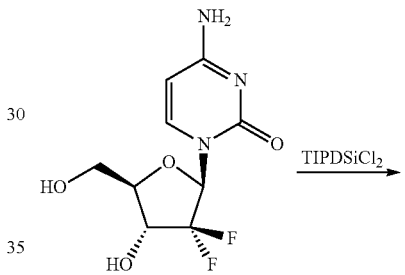

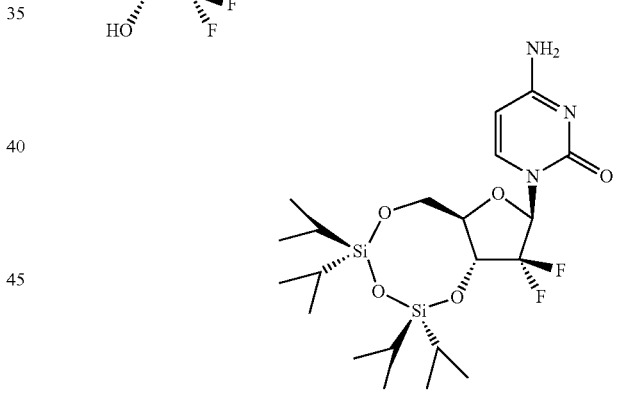

The protected gemcitabine is, in turn, treated with an appropriate carboxyl halide to form an amide bond to R:

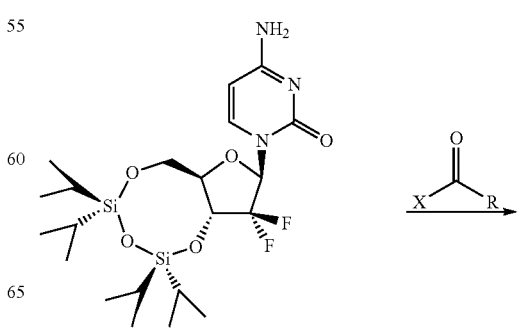

-continued

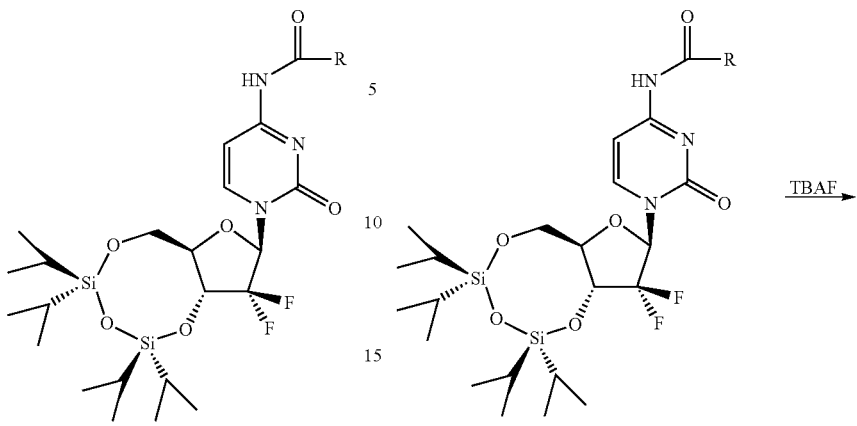

wherein R is Ar¹ or Ar³.

In one specific example, 3,4,5-trimethoxybenzoyl chloride provides N-(1-((6aR,8R,9aR)-9,9-difluoro-2,2,4,4-tetraisopropyltetrahydro-6H-furo[3,2-f][1,3,5,2,4]trioxadisilocin-8-yl)-2-oxo-1,2-dihydropyrimidin-4-yl)-3,4,5-trimethoxybenzamide:

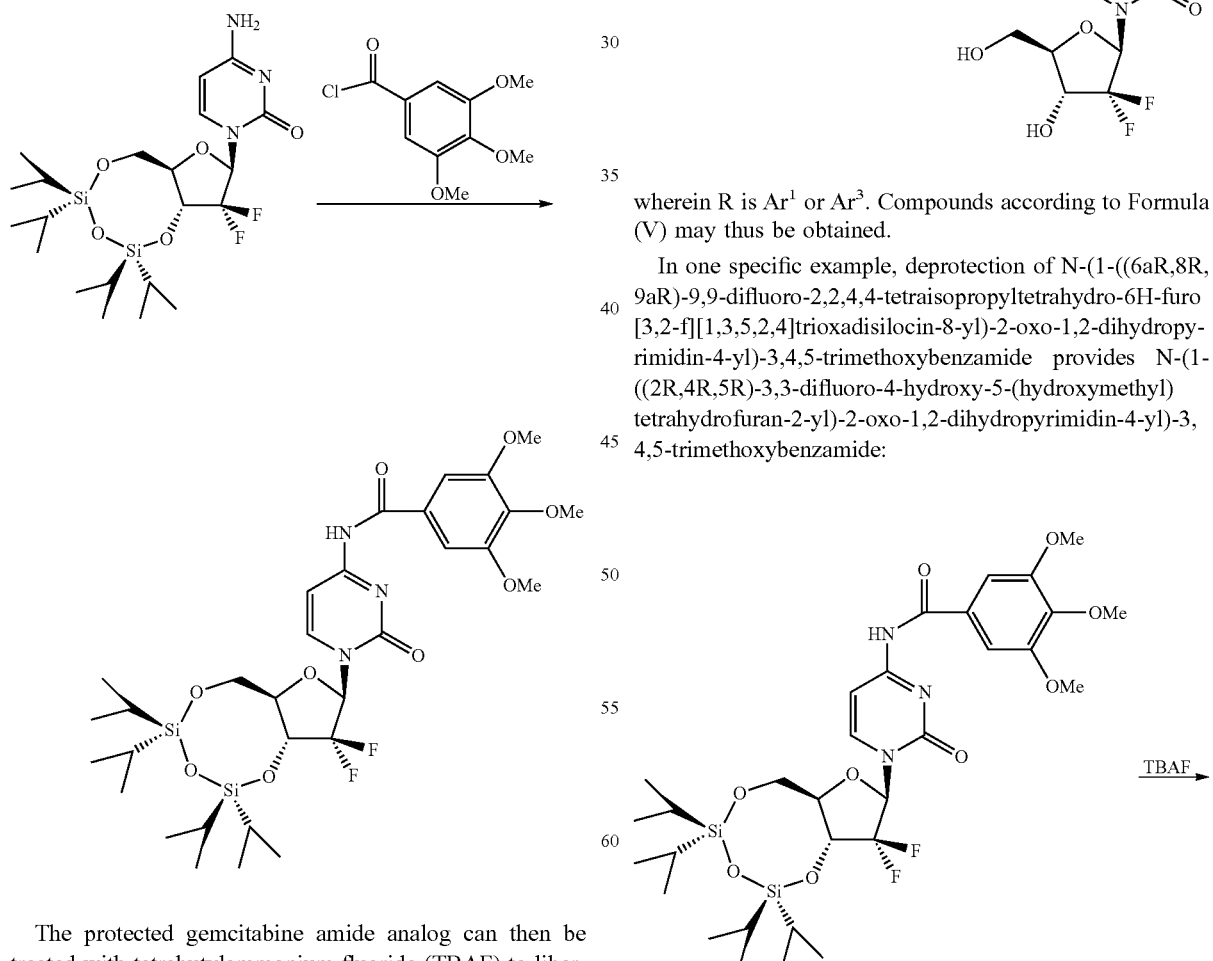

wherein R is Ar¹ or Ar³. Compounds according to Formula (V) may thus be obtained.

In one specific example, deprotection of N-(1-((6aR,8R,9aR)-9,9-difluoro-2,2,4,4-tetraisopropyltetrahydro-6H-furo[3,2-f][1,3,5,2,4]trioxadisilocin-8-yl)-2-oxo-1,2-dihydropyrimidin-4-yl)-3,4,5-trimethoxybenzamide provides N-(1-((2R,4R,5R)-3,3-difluoro-4-hydroxy-5-(hydroxymethyl)tetrahydrofuran-2-yl)-2-oxo-1,2-dihydropyrimidin-4-yl)-3,4,5-trimethoxybenzamide:

The protected gemcitabine amide analog can then be treated with tetrabutylammonium fluoride (TBAF) to liberate the hydroxyl groups. Deprotection provides the corresponding deprotected gemcitabine amide analog:

-continued

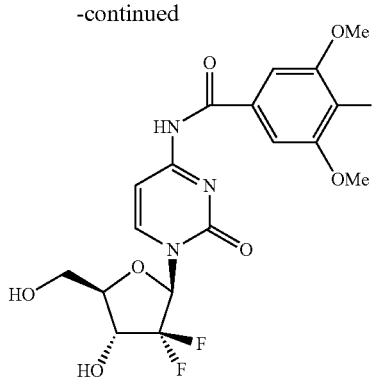

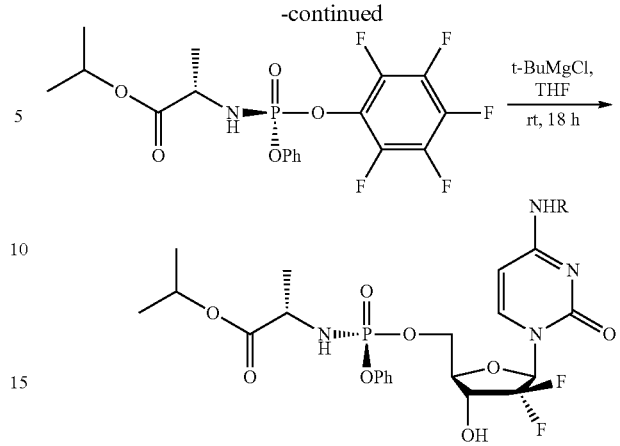

Alternatively, the amine group of gemcitabine may be amidated by reaction with a carboxylic acid compound in one or more suitable solvents, for example, according to the following general reaction scheme:

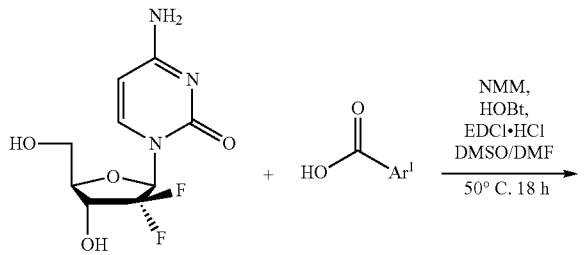

wherein R is $Ar^1$ or $Ar^3$.

Monophosphorylated compounds according to Formula (I) can be prepared by reaction of the 4-amido analog with the appropriate phosphorylated compound. For example, in one embodiment, the method may be according to the following reaction scheme:

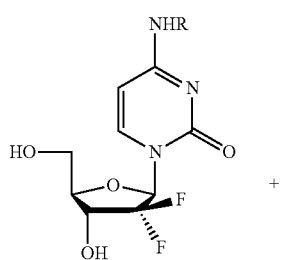

wherein R is $Ar^1$ and the 4-amido analog is reacted with a solution of (S)-2-[(S)-(2,3,4,5,6-pentafluorophenoxy)-phenoxyphosphorylamino] propionic acid isopropyl ester (23.06 mmol) in THF and in the presence of tert-butylmagnesium chloride. This reaction is further described in the Examples.

The disclosed methods of making can provide compounds that can contain one or more asymmetric centers and, thus, potentially give rise to enantiomers and diastereomers. Unless stated to the contrary, the compounds prepared by the disclosed methods include all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included.

In one aspect, the disclosed methods of making can provide racemic or scalemic mixtures that can be resolved to pure or substantially pure enantiomers using chiral phase chromatography or other suitable methods known to one skilled in the art. As known to one skilled in the art, a variety specific columns and/or mobile phases can affect the desired resolution of enantiomers, and the specific choice can be determined by one skilled in the art. As known to one skilled in the art, chiral chromatography can be carried out in a variety of formats (e.g. SFC, HPLC, and SMB), and other formats can be used to obtain similar results. Moreover, other suitable methods known to one skilled in the art for the separation and isolation of individual enantiomers from a racemic or scalemic mixture can be used to isolate specific enantiomers as needed.

C. Pharmaceutical Compositions

In another embodiment, the invention is directed to pharmaceutical compositions comprising the disclosed compounds. That is, a pharmaceutical composition can be provided comprising an effective amount of at least one disclosed compound, or a pharmaceutically acceptable salt, solvate, hydrate, or polymorph thereof, and a pharmaceutically acceptable carrier. In a further aspect, the effective amount is a therapeutically effective amount. In a still further aspect, the effective amount is a prophylactically effective amount. In one aspect, the invention relates to a medicament comprising one or more disclosed compounds; or a pharmaceutically acceptable salt, hydrate, solvate, or polymorph thereof.

The pharmaceutical compositions comprise the compound as described, or a pharmaceutically acceptable salt, solvate, hydrate, or polymorph thereof, as an active ingredient, and a pharmaceutically acceptable carrier. The compositions may optionally include one or more additional therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. In a specific embodiment, the compositions are suitable for oral administration. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic nontoxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. In specific embodiments, a salt is formed from citric, hydrobromic, hydrochloric, maleic, phosphoric, sulfuric, or tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral, parenteral (including intravenous), inhalation, etc. Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The pharmaceutical compositions may contain a compound of the invention in an amount effective for the desired therapeutic effect. In specific embodiments, the pharmaceutical compositions are in a unit dosage form and comprise from about 1 to about 1000 mg per unit dosage form. In further embodiments, the pharmaceutical compositions comprise from about 1 to about 500 mg per unit dosage form or from about 500 to 1000 mg per unit dosage form. Such dosage forms may be solid, semisolid or liquid, or adapted for delivery via aerosol or the like for inhalation administration.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

It is understood that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

Thus, in one aspect, the invention relates to a pharmaceutical composition comprising a pharmaceutically acceptable carrier and an effective amount of a disclosed compound. In further embodiments, the composition further comprises one or more of: (a) a drug known to treat a disorder of uncontrolled cellular proliferation; (b) a substance known to increase risk of uncontrolled cellular proliferation; (c) an antiviral agent; and (d) a substance known to increase risk of viral infection. In a more specific embodiment, the composition comprises a pharmaceutically acceptable carrier and an effective amount of a disclosed compound, and further comprises one or more of (a) a drug known to treat a disorder of uncontrolled cellular proliferation, and (b) a substance known to increase risk of uncontrolled cellular proliferation. In another more specific embodiment, the composition comprises a pharmaceutically acceptable carrier and an effective amount of a disclosed compound, and further comprises one or more of (a) an antiviral agent; and (b) a substance known to increase risk of viral infection. In a further aspect, the composition further comprises carboplatin.

D. Kits

In one aspect, the invention relates to kits comprising at least one disclosed compound; or a pharmaceutically acceptable salt, hydrate, solvate, or polymorph thereof, or at least one disclosed pharmaceutical composition and one or more of: (a) an antiviral agent or a substance known to increase risk of viral infection, and optionally, instructions for treating a viral infection; or (d) a drug known to treat a disorder of uncontrolled cellular proliferation or a substance known to increase risk of uncontrolled cellular proliferation, and optionally, instructions for treating a disorder of uncontrolled cellular proliferation. In a more specific embodiment, the drug known to treat a disorder of uncontrolled cellular proliferation is carboplatin.

In a specific embodiment, the at least one disclosed compound and the agent or substance are coformulated. In a still further embodiment, the at least one compound and the at least one agent or substance are co-packaged. The kits can also comprise compounds and/or products co-packaged, coformulated, and/or co-delivered with other components. For example, a drug manufacturer, a drug reseller, a physician, a compounding shop, or a pharmacist can provide a kit comprising a disclosed compound and/or product and another component for delivery to a patient.

E. Treatment Methods

In further embodiments, the invention is directed to treatment methods employing a disclosed compound or composition. In specific embodiments, the inventive compound or composition can be used as a single agent or, alternatively, in combination with one or more other drugs, in the treatment, prevention, control, amelioration or reduction of risk of the diseases, disorders and conditions described herein. A combination as described may be employed where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent. It is also contemplated that when used in combination with one or more other active ingredients, the disclosed compounds and the other active ingredients can be used in lower doses than when each is used singly.

In one aspect, the compound is used to treat a subject as defined herein. In specific embodiments, the subject is a mammal. In a yet a further embodiment, the mammal is a human. In a further aspect, the mammal has been diagnosed with a need for treatment of a disorder prior to the administering step.

The compounds disclosed herein are useful for treating, preventing, ameliorating, controlling or reducing the risk of a variety of disorders, including, for example, viral disorders (e.g., hepatitis) and disorders of uncontrolled cellular proliferation (e.g., cancers).

In one aspect, the invention relates to a method for treating a subject for viral infection. The method comprises the step of administering to the subject a therapeutically or prophylactically effective amount of a disclosed compound or pharmaceutical composition. In one aspect, the subject is a mammal. In a further aspect, the mammal is a human. In a further aspect, the mammal has been diagnosed with a need for treatment of the infection prior to the administering step. In a further aspect, the method further comprises the step of identifying a mammal in need of treatment of the infection.

In a specific embodiment, the viral infection is viral hepatitis. In a more specific embodiment, the viral infection is Hepatitis A, Hepatitis B, or Hepatitis C. In yet a more specific embodiment, the viral infection is Hepatitis C (HCV). In a further aspect, the viral infection is dengue virus, Human immunodeficiency virus, Herpes simplex, Cytomegalovirus, Epstein-Barr virus, or Yellow fever.

In another embodiment, the invention relates to a method for inhibiting viral replication within at least one cell. The method comprises the step of administering to the cell a disclosed compound or pharmaceutical composition in an amount effective to inhibit viral replication within the at least one cell. In one aspect, the cell is a mammalian cell. In a further aspect, the cell is a human cell. In a further aspect, administration to the cell is performed in vitro. In a further aspect, administration to the cell is performed in vivo. In a further aspect, the replication of viral hepatitis is inhibited. In a further aspect, the replication of Hepatitis A, Hepatitis B, or Hepatitis C is inhibited. In a further aspect, the replication of dengue virus, Human immunodeficiency virus, Herpes simplex, Cytomegalovirus, Epstein-Barr virus, or Yellow fever is inhibited.

In other embodiments, the invention relates to a method for treating a disorder of uncontrolled cellular proliferation. The method comprises administering to a subject a therapeutically or prophylactically effective amount of a disclosed compound or pharmaceutical composition. In one aspect, the subject is a mammal. In a further aspect, the mammal is a human. In a further aspect, the mammal has been diagnosed with a need for treatment of the disorder prior to the administering step. In a further aspect, the method further comprises the step of identifying a mammal in need of treatment of the disorder.

In a further aspect, the disorder is cancer. In a further aspect, the disorder is carcinoma. In a further aspect, the disorder is selected from non-small cell lung cancer, pancreatic cancer, bladder cancer, and breast cancer. In a further aspect, the disorder is esophageal cancer. In a further aspect, the disorder is lymphoma.

In specific embodiments, the invention relates to a method for arresting tumor growth. The method comprises administering to at least one tumor cell a disclosed compound or pharmaceutical composition in an amount effective to arrest growth of the tumor. In one aspect, the cell is a mammalian. In a further aspect, the cell is a human. In a further aspect, administration to the cell is performed in vitro. In a further aspect, administration to the cell is performed in vivo.

In a further aspect, the tumor is selected from non-small cell lung cancer, pancreatic cancer, bladder cancer, and breast cancer. In a further aspect, the tumor is esophageal cancer. In a further aspect, the tumor is lymphoma.

In a specific embodiment of the described methods of treatment, the subject has been identified as exhibiting resistance to treatment with gemcitabine.

Another aspect of the invention is the use of the disclosed compounds and compositions in any of the described methods or in manufacturing a medicament for use in any of the described methods. In one aspect, the invention relates to use of at least one disclosed compound or a pharmaceutically acceptable salt, hydrate, solvate, or polymorph thereof.

EXAMPLES

The following examples are put forth so as to provide those of ordinary skill in the art with a complete disclosure and description of how the compounds, compositions, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein. The Examples are provided herein to illustrate processes for preparing compounds of the invention, and should not be construed as limiting the invention in any way. The Examples are typically depicted in free base form. Examples are provided herein to illustrate the invention, and should not be construed as limiting the invention in any way.

All solvents were dried with solvent-purification system (Innovative Technology, Inc). Analytical TLC was carried out on E. Merck silica gel 60 F254 aluminum-backed plates. The preparation TLC was carried out on silica gel 60 F254 plates (20×20 cm, 1 mm) from EMD Chemicals, Inc. The 230-400 mesh size of the absorbent was utilized for all chromatographic purifications. $^1$H NMR and high-resolution mass spectra were obtained at The Ohio State University Campus Chemical Instrumentation Center.

Example 1, Synthesis of Gemcitabine Analogs According to Formula (I)

The following general procedure was employed to form the indicated compounds according to the invention.

A. Preparation of 3',5'-O-(1,1,3,3-Tetraisopropyldisiloxane-1,3-Dily) Gemcitabine To a solution of gemcitabine (136.6 mg, 0.52 mmol) in dry pyridine (40 mL), 1,3-dichloro-1,1,3,3-tetraisopropyldisiloxane (TIPDSiCl2) (0.17 mL) was added slowly with stirring. The mixture was stirred at room temperature for 48 h. Pyridine was then removed under reduced pressure and the residue was subjected to a silica gel column chromatography, with a gradient of methanol (1-2.5%) in $CH_2Cl_2$ to give 3',5'-O-(1,1,3,3-tetraisopropyldisiloxane-1,3-dily) gemcitabine as a white foam (189.7 mg, 72%).

B. Preparation of Amide Derivative

To the solution of 3',5'-O-(1,1,3,3-tetraisopropyldisiloxane-1,3-dily) gemcitabine (0.054 mmol) in dry pyridine (7 mL), the appropriate carboxyl chloride (1.5 eq.) was added slowly with stirring. The mixture was stirred at room temperature for overnight. The solvent was removed and the residue was used to the next reaction without further purification. TBAF (1 M in THF, 0.3 mL) was then added to the solution of the residue and the resulted solution was stirred at room temperature for 1.5 h. After the removal of the solvent, the residue was subjected to silica gel column chromatography, with a stepwise gradient of methanol (1-3%) in $CH_2Cl_2$ to give a raw product. The raw product was further purified by high performance liquid chromatography (HPLC) by using a gradient of water/methanol or water/acetonitrile. HPLC fractions containing pure a gemcitabine amide derivative were lyophilized overnight to yield a dried product with a purity of >99%.

C. Preparation of Phosphorolated Compound

The resulting gemcitabine amide analog was then phosphorylated by one of the following general procedures.

The general process for the phosphoramidite analogs: To a stirred suspension of gemcitabine amide analog (19.1 mmol, dried under vacuum at 50° C. for 20 h) in dry THF (75 mL) was added a 1.7 M solution of tert-butylmagnesium chloride in THF (40.35 mmol) using an addition funnel over a period of 30 min at 0° C. The white suspension was warmed to ambient temperature at which temperature it was stirred for additional 30 min. A solution of (S)-2-[(S)-(2,3,4,5,6-pentafluorophenoxy)-phenoxyphosphorylamino] propionic acid isopropyl ester (23.06 mmol) in THF (50 mL) was then added over a period of 30 min. The mixture was stirred at room temperature for 18 h. The reaction mixture was concentrated and dissolved in ethyl acetate (50 ml). The organic layer was washed with water (2×10 mL), and brine (10 mL). The organic layer was dried over anhydrous sodium sulfate, filtered, and evaporated. The residue was purified with flash chromatograph with DCM in MeOH, then further purified with HPLC using 30%-100% $CH_3CN$ in water as eluting solvent. HPLC fractions containing pure phosphorylated gemcitabine amide derivative were lyophilized overnight to yield a dried product with a purity of >99%.

The process for the cyclic phosphorylated analogs: To a stirred suspension of gemcitabine amide analog (12.8 mmol, dried under vacuum at 50° C. for 20 h) in dry DCM (100 mL) was added trimethylamine (51.2 mmol) at room temperature. The reaction mixture was cooled to −20° C., and then was added isopropyl phosphorodichloridate (16.6 mmol) over a period of 20 min. The mixture was stirred at −20° C. for 15 min and then NMI (26.9 mmol) was added dropwise over a period of 15 min. The mixture was stirred at this temperature for 1 h and then slowly warmed to room temperature in 20 h. The reaction mixture was concentrated and dissolved in ethyl acetate (150 mL). The organic layer was washed with water (3×20 mL), and brine (20 mL). The organic layer was dried over anhydrous sodium sulfate, filtered, and concentrated. The residue was purified with flash chromatograph with DCM in MeOH, then further purified with HPLC using 30%-100% $CH_3CN$ in water as eluting solvent. HPLC fractions containing pure phosphorylated gemcitabine amide derivative were lyophilized overnight to yield a dried product with a purity of >99%.

These general procedures were employed to form Compounds 1, 3, 4, and 13 as follows:

Compound 1: ((S)-isopropyl 2-(((S)-(((2R,3R,5R)-4,4-difluoro-3-hydroxy-5-(2-oxo-4-(2-propylpentanamido)pyrimidin-1(2H)-yl)tetrahydrofuran-2-yl)methoxy)(phenoxy)phosphoryl)amino)propanoate)

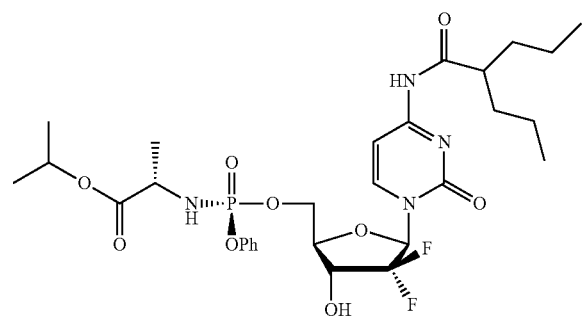

$^1$H NMR (400 MHz, DMSO-$d_6$): δ0.85 (td, J=7.2 Hz and 1.6 Hz, 6H), 1.10-1.40 (m, 15H), 1.46-1.60 (m, 2H), 2.58-2.69 (m, 1H), 3.75-3.88 (m, 1H), 4.06-4.13 (m, 1H), 4.16-4.40 (m, 3H), 4.80-4.92 (m, 1H), 6.10-6.26 (m, 2H), 6.51 (d, J=6.4 Hz, 1H), 7.14-7.26 (m, 3H), 7.28-7.43 (m, 3H), 7.98 (d, J=7.6 Hz, 1H), 11.10 (s, 1H); MS-ESI (m/z): calcd for $C_{29}H_{41}F_2N_4O_9P$ [M+H]$^+$659.3. found 659.5.

Compound 3: ((S)-isopropyl 2-(((S)-(((2R,3R,5R)-4,4-difluoro-3-hydroxy-5-(2-oxo-4-((3,4,5-trimethoxybenzyl)amino)pyrimidin-1(2H)-yl)tetrahydrofuran-2-yl)methoxy)(phenoxy)phosphoryl)amino)propanoate)

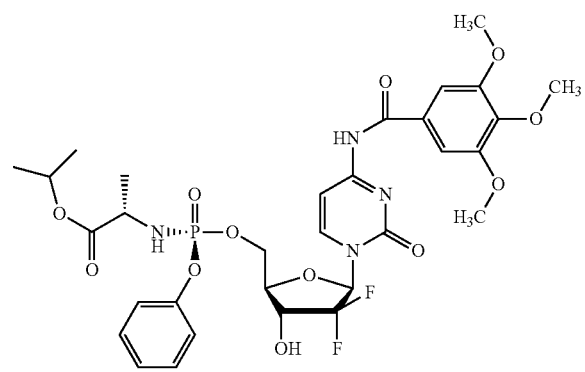 [SMILES: COc1cc(C(=O)Nc2ccn([C@@H]3O[C@H](CO[P@@](=O)(N[C@@H](C)C(=O)OC(C)C)Oc4ccccc4)[C@H](O)C3(F)F)c(=O)n2)cc(OC)c1OC]

$^1$H NMR (250 MHz, DMSO-$d_6$): δ 1.13-1.17 (m, 6H), 1.24 (d, J=7.0 Hz, 3H), 3.74 (s, 3H), 3.75-3.85 (m, 1H), 3.86 (s, 6H), 4.08-4.14 (m, 1H), 4.22-4.38 (m, 3H), 4.80-4.92 (m, 1H), 6.11-6.28 (m, 2H), 6.52 (d, J=6.0 Hz, 1H), 7.16-7.26 (m, 3H), 7.36-7.42 (m, 5H), 7.98 (d, J=7.6 Hz, 1H), 11.42 (bs, 1H); MS-ESI (m/z): calcd for $C_{31}H_{37}F_2N_4O_{12}P$ [M+H]$^+$ 727.2. found 727.4.

Compound 4: ((S)-isopropyl 2-(((S)-(((2R,3R,5R)-5-(4-((benzo[d][1,3]dioxol-5-ylmethyl)amino)-2-oxopyrimidin-1(2H)-yl)-4,4-difluoro-3-hydroxytetrahydrofuran-2-yl)methoxy)(phenoxy)phosphoryl)amino)propanoate)

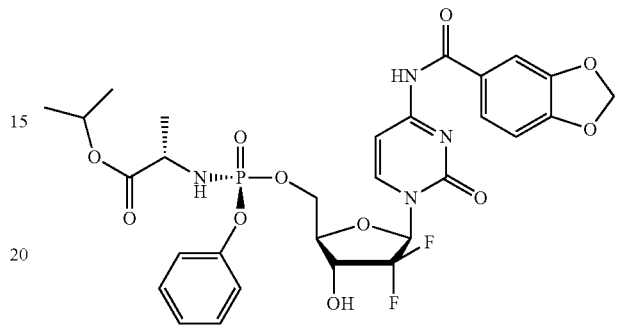

$^1$H NMR (600 MHz, DMSO-$d_6$): δ 1.13-1.17 (m, 6H), 1.25 (d, J=7.2 Hz, 3H), 3.79-3.87 (m, 1H), 4.09-4.14 (m, 1H), 4.22-4.39 (m, 3H), 4.84-4.91 (m, 1H), 5.76 (s, 1H), 6.14-6.15 (m, 2H), 6.23-6.26 (m, 1H), 6.51 (d, J=6.6 Hz, 1H), 7.04-7.68 (m, 9H), 8.03 (d, J=7.2 Hz, 1H), 11.23 (s, 1H); MS-ESI (m/z): calcd for $C_{29}H_{31}F_2N_4O_{11}P$ [M+H]$^+$ 681.2. found 681.6.

Compound 13: (2S)-isopropyl 2-(((R)-(((2R,3R)-5-(4-(2,3-dihydro-1H-indene-2-carboxamido)-2-oxopyrimidin-1(2H)-yl)-4,4-difluoro-3-hydroxytetrahydrofuran-2-yl)methoxy)(phenoxy)phosphoryl)amino)-propanoate

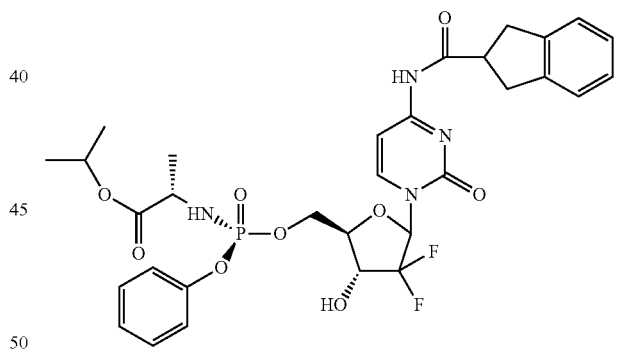

MS-ESI (m/z): calcd for $C_{31}H_{35}F_2N_4O_9P$ [M+Na]$^+$ 699.2. found 699.2.

General Procedures for Synthesis of Gemcitabine Cyclic Phosphorylated Derivatives.

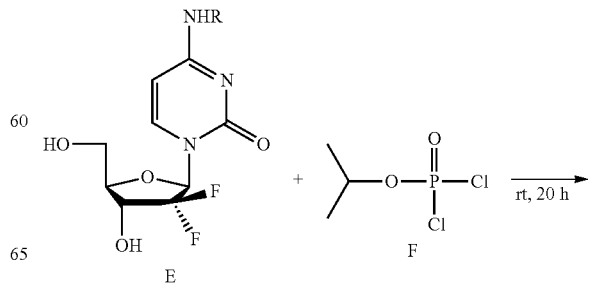

-continued

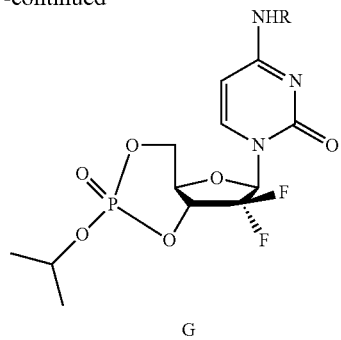

G

Scheme 4. Reagents and Conditions:
(a) NEt₃, NMI, DCM, −20° C. to room temperature.

To a stirred suspension of gemcitabine amide analog E (12.8 mmol, dried under vacuum at 50° C. for 20 h) in dry DCM (100 mL) was added trimethylamine (51.2 mmol) at room temperature. The reaction mixture was cooled to −20° C., and then was added isopropyl phosphorodichloridate F (16.6 mmol) over a period of 20 min. The mixture was stirred at −20° C. for 15 min and then NMI (26.9 mmol) was added dropwise over a period of 15 min. The mixture was stirred at this temperature for 1 h and then slowly warmed to room temperature in 20 h. The reaction mixture was concentrated and dissolved in ethyl acetate (150 mL). The organic layer was washed with water (3×20 mL), and brine (20 mL). The organic layer was dried over anhydrous sodium sulfate, filtered, and concentrated. The residue was purified with flash chromatograph with DCM in MeOH, then further purified with HPLC using 30%-100% CH₃CN in water as eluting solvent. HPLC fractions containing pure phosphorylated gemcitabine amide derivative were lyophilized overnight to yield a dried product G with a purity of >99%.

Compound 2 was made according to this general procedure:

Compound 2: (N-(1-((2S,4aR,6R,7aR)-7,7-difluoro-2-isopropoxy-2-oxidotetrahydro-4H-furo[3,2-d][1,3,2]-dioxaphosphinin-6-yl)-2-oxo-1,2-dihydropyrimidin-4-yl)-2-propylpentanamide)

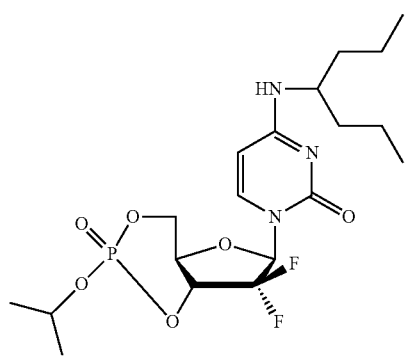

¹H NMR (600 MHz, DMSO-d₆): δ 0.86 (td, J=7.8 Hz and 3.6 Hz, 6H), 1.19-1.28 (m, 4H), 1.31-1.38 (m, 8H), 1.49-1.57 (m, 2H), 2.62-2.67 (m, 1H), 4.42-4.46 (m, 1H), 4.66-4.78 (m, 3H), 4.16-4.40 (m, 3H), 5.32 (m, 1H), 6.45 (bs, 1H), 7.35 (d, J=7.8 Hz, 1H), 8.28 (d, J=7.8 Hz, 1H), 11.15 (s, 1H).

MS-ESI (m/z): calcd for $C_{20}H_{30}F_2N_3O_7P$ [M+H]⁺ 494.2. found 494.4.

Example 2, Synthesis of Gemcitabine Analogs According to Formula (V)

All solvents were dried with solvent-purification system (Innovative Technology, Inc). Analytical TLC was carried out on E. Merck silica gel 60 F254 aluminum-backed plates. The preparation TLC was carried out on silica gel 60 F254 plates (20×20 cm, 1 mm) from EMD Chemicals, Inc. The 230-400 mesh size of the absorbent was utilized for all chromatographic purifications. ¹H NMR, ¹³C NMR, ESI mass spectra were obtained at The Ohio State University Campus Chemical Instrumentation Center.

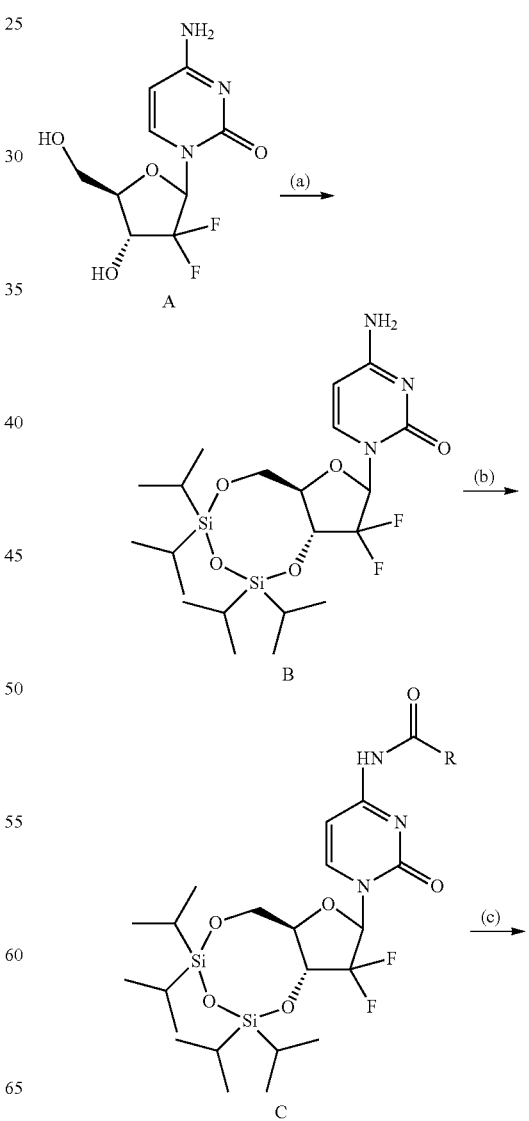

-continued

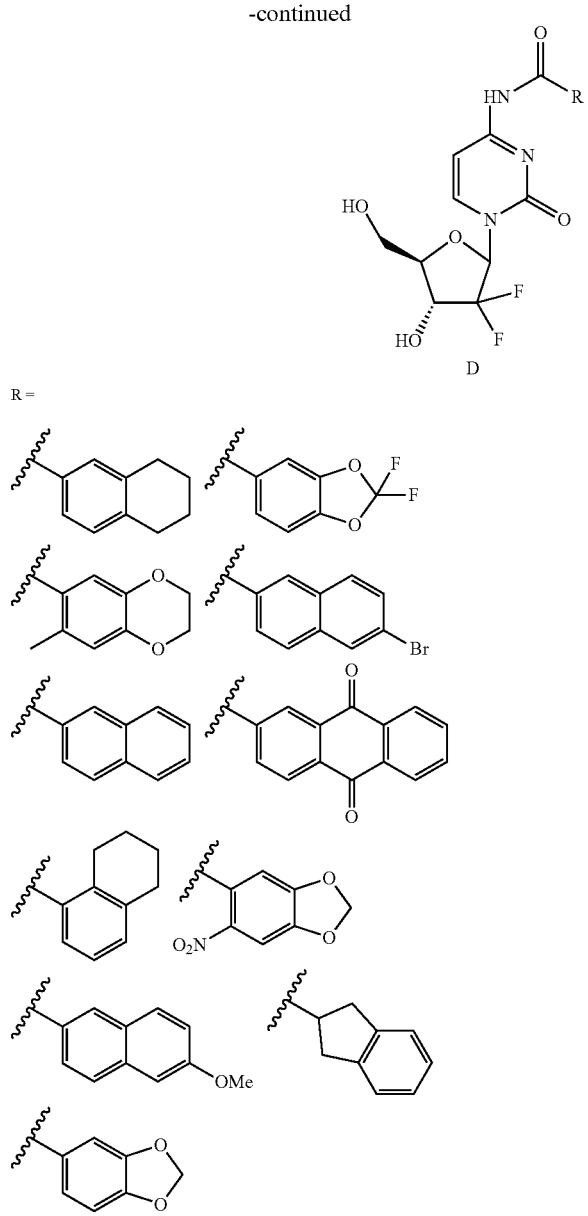

Scheme 1. Reagents and Conditions in Each Step:

(a) TPDSCl$_2$, pyridine, room temperature; (b) RCOCl, pyridine, room temperature; (c) TBAF/THF, room temperature.

Preparation of 3',5'-O-(1,1,3,3-Tetraisopropyldisiloxane-1,3-dily) Gemcitabine B To the solution of gemcitabine A (136.6 mg, 0.52 mmol) in dry pyridine (40 mL), 1,3-dichloro-1,1,3,3-tetraisopropyldisloxane (TPDSCl$_2$) (0.17 mL) was added slowly with stirring. The mixture was stirred at room temperature for 48 h. Pyridine was then removed under reduced pressure and the residue was subjected to a silica gel column chromatography, with a gradient of methanol (1-2.5%) in CH$_2$Cl$_2$ to give B as a white foam (189.7 mg, 72%).

$^1$H NMR (600 MHz, DMSO-d$_6$): δ 0.97-1.09 (m, 24H), 3.93-4.0 (m, 2H), 4.14-4.19 (m, 1H), 4.23-4.45 (m, 1H), 5.81 (d, J=7.8 Hz, 1H), 6.01-6.20 (m, 1H), 7.41 (s, 1H), 7.46-7.51 (m, 2H).

13C NMR (600 MHz, DMSO-d6): d 12.1, 12.2, 12.5, 12.8, 16.7, 16.8, 16.9, 17.2, 17.3, 17.4, 0.4, 70.4, 78.1, 83.9, 95.1, 122.5 (t, J=255.0 Hz), 139.5, 154.7, 165.8.

MS-ESI (m/z): calcd for C21H37F2N3O5Si2 [M+Na]+ 528.2. found 528.2.

General Procedures for Synthesis of Gemcitabine Derivatives of Formula (V).

To the solution of Compound B (0.054 mmol) in dry pyridine (7 mL), carboxyl chloride (1.5 eq.) was added slowly with stirring. The mixture was stirred at room temperature for overnight. The solvent was removed and the residue C was used to the next reaction without further purification. TBAF (1 M in THF, 0.3 mL) was then added to the solution of the residue and the resulted solution was stirred at room temperature for 1.5 h. After the removal of the solvent, the residue was subjected to silica gel column chromatography, with a stepwise gradient of methanol (1-5%) in CH$_2$Cl$_2$ to give the raw product of D. The raw product was further purified by C-18 reverse phase preparative HPLC (a gradient of acetonitrile/water). HPLC fractions containing pure gemcitabine derivative were lyophilized overnight to yield a dried product in 60-80% yield with a purity of >99%.

These general procedures were employed to form Compounds 5-11 as follows:

Compound 5: N-(1-((4R,5R)-3,3-difluoro-4-hydroxy-5-(hydroxymethyl)tetrahydrofuran-2-yl)-2-oxo-1,2-dihydropyrimidin-4-yl)-5,6,7,8-tetrahydronaphthalene-2-carboxamide

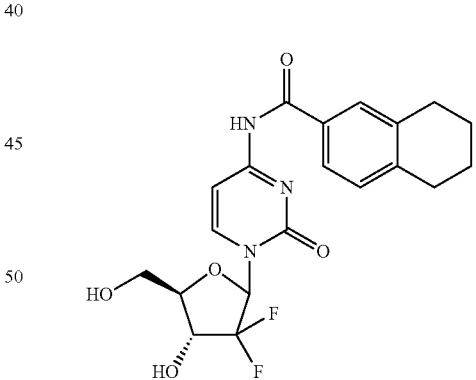

$^1$H NMR (600 MHz, DMSO-d$_6$): δ 1.76, (s, 4H), 2.78 (s, 4H), 3.65-3.71 (m, 1H), 3.81-3.86 (m, 1H), 3.90-3.94 (m, 1H), 4.18-4.27 (m, 1H), 5.34 (t, J=4.8 Hz, 1H), 6.22 (t, J=7.2 Hz, 1H), 6.34 (d, J=6.6 Hz, 1H), 7.19 (d, J=7.8 Hz, 1H), 7.41 (d, J=7.2 Hz, 1H), 7.72 (d, J=8.4 Hz, 1H), 7.77 (s, 1H), 8.31 (d, J=7.8 Hz, 1H), 11.22 (brs, 1H).

13C NMR (100 MHz, DMSO-d6): d 22.6, 22.7, 28.9, 29.1, 59.0, 68.6 (t, J=21.9 Hz), 81.2, 84.4 (t, J=32.8 Hz), 96.8, 123.2 (t, J=257.0 Hz), 125.7, 129.2, 129.5, 130.2, 137.0, 142.6, 144.8, 154.4, 163.9, 167.5.

MS-ESI (m/z): calcd for C20H21F2N3O5 [M+Na]+ 444.1. found 444.1.

Compound 6: 6-bromo-N-(1-((4R,5R)-3,3-difluoro-4-hydroxy-5-(hydroxymethyl)tetrahydrofuran-2-yl)-2-oxo-1,2-dihydropyrimidin-4-yl)-2-naphthamide

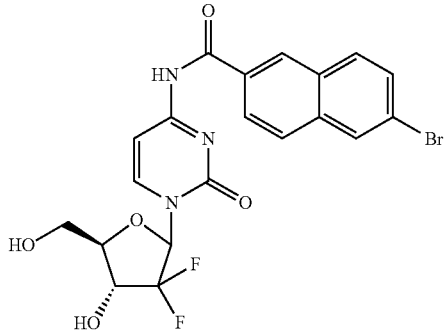 [SMILES: O=C(Nc1ccn(C2O[C@H](CO)[C@@H](O)C2(F)F)c(=O)n1)c1ccc2cc(Br)ccc2c1]

$^1$H NMR (600 MHz, DMSO-$d_6$): δ 3.66-3.72 (m, 1H), 3.81-3.87 (m, 1H), 3.91-3.96 (m, 1H), 4.20-4.29 (m, 1H), 5.35 (t, J=5.4 Hz, 1H), 6.24 (t, J=7.2 Hz, 1H), 6.36 (d, J=6.6 Hz, 1H), 7.46 (d, J=7.8 Hz, 1H), 7.77 (d, J=9.0 Hz, 1H), 8.02-8.10 (m, 3H), 8.34 (s, 1H), 8.36 (d, J=7.2 Hz, 1H), 8.74 (s, 1H), 11.55 (brs, 1H).

$^{13}$C NMR (600 MHz, DMSO-$d_6$): δ 59.0, 68.6 (t, J=22.5 Hz), 81.3, 84.4 (t, J=33.2 Hz), 96.8, 122.2, 123.2 (t, J=257.4 Hz), 125.9, 127.6, 129.9, 130.0, 130.3, 130.6, 131.0, 131.7, 136.1, 145.0, 154.4, 163.9, 167.4.

MS-ESI (m/z): calcd for $C_{20}H_{16}BrF_2N_3O_5$ [M+Na]$^+$ 518.0. found 518.0.

Compound 7: N-(1-((4R,5R)-3,3-difluoro-4-hydroxy-5-(hydroxymethyl)tetrahydrofuran-2-yl)-2-oxo-1,2-dihydropyrimidin-4-yl)-2-naphthamide

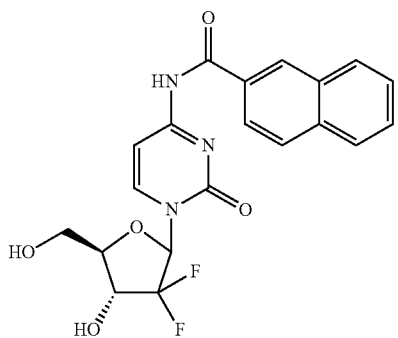 [SMILES: O=C(Nc1ccn(C2O[C@H](CO)[C@@H](O)C2(F)F)c(=O)n1)c1ccc2ccccc2c1]

$^1$H NMR (600 MHz, DMSO-$d_6$): δ 3.66-3.72 (m, 1H), 3.82-3.87 (m, 1H), 3.91-3.95 (m, 1H), 4.19-4.28 (m, 1H), 5.41 (t, J=5.4 Hz, 1H), 6.23 (t, J=7.2 Hz, 1H), 6.43 (d, J=6.6 Hz, 1H), 7.46 (brs, 1H), 7.64 (t, J=7.8 Hz, 1H), 7.68 (t, J=7.2 Hz, 1H), 7.99-8.09 (m, 4H), 8.35 (d, J=7.2 Hz, 1H), 8.71 (s, 1H), 11.49 (brs, 1H).

$^{13}$C NMR (600 MHz, DMSO-$d_6$): δ 59.0, 68.6 (t, J=22.1 Hz), 81.3, 84.4 (t, J=29.1 Hz), 97.0, 123.2 (t, J=257.4 Hz), 124.9, 127.3, 127.9, 128.4, 128.8, 129.6, 130.0, 130.4, 132.1, 135.0, 144.9, 154.4, 163.9, 167.7.

MS-ESI (m/z): calcd for $C_{20}H_{17}F_2N_3O_5$[M+Na]$^+$ 440.1. found 440.1.

Compound 8: N-(1-((4R,5R)-3,3-difluoro-4-hydroxy-5-(hydroxymethyl)tetrahydrofuran-2-yl)-2-oxo-1,2-dihydropyrimidin-4-yl)-9,10-dioxo-9,10-dihydroanthracene-2-carboxamide

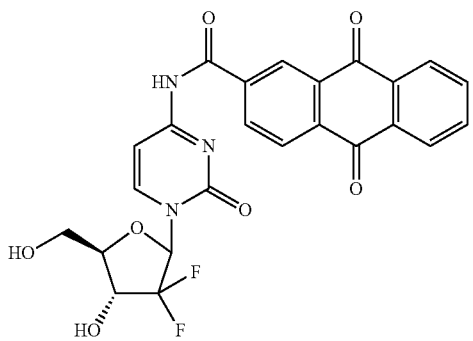 [SMILES: O=C(Nc1ccn(C2O[C@H](CO)[C@@H](O)C2(F)F)c(=O)n1)c1ccc2c(c1)C(=O)c1ccccc1C2=O]

$^1$H NMR (600 MHz, DMSO-$d_6$): δ 3.66-3.73 (m, 1H), 3.82-3.87 (m, 1H), 3.91-3.95 (m, 1H), 4.17-4.28 (m, 1H), 5.42 (t, J=5.4 Hz, 1H), 6.20 (t, J=7.2 Hz, 1H), 6.44 (d, J=6.6 Hz, 1H), 7.35 (brs, 1H), 7.90-7.94 (m, 2H), 8.16-8.21 (m, 2H), 8.24 (d, J=8.4 Hz, 1H), 8.31-8.35 (m, 1H), 8.36-8.39 (m, 1H), 8.65 (s, 1H), 11.79 (brs, 1H).

$^{13}$C NMR (600 MHz, DMSO-$d_6$): δ 59.0, 68.5 (t, J=22.2 Hz), 81.3, 84.4 (t, J=32.7 Hz), 97.0, 123.2 (t, J=257.3 Hz), 127.1, 127.2, 127.3, 133.0, 133.2, 134.0, 135.0, 135.5, 138.1, 145.1, 154.2, 163.6, 166.5, 182.0, 182.2.

MS-ESI (m/z): calcd for $C_{24}H_{17}F_2N_3O_7$[M+Na]$^+$ 520.1. found 520.1.

Compound 9: N-(1-((4R,5R)-3,3-difluoro-4-hydroxy-5-(hydroxymethyl)tetrahydrofuran-2-yl)-2-oxo-1,2-dihydropyrimidin-4-yl)-5,6,7,8-tetrahydronaphthalene-1-carboxamide

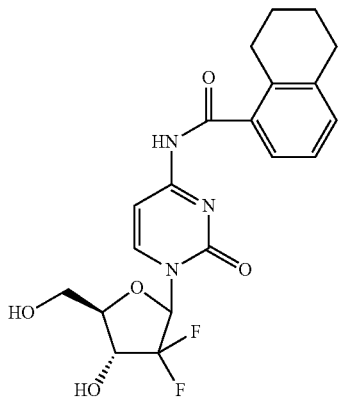 [SMILES: O=C(Nc1ccn(C2O[C@H](CO)[C@@H](O)C2(F)F)c(=O)n1)c1cccc2c1CCCC2]

$^1$H NMR (600 MHz, DMSO-$d_6$): δ 1.73 (s, 4H), 2.76-2.81 (m, 4H), 3.65-3.71 (m, 1H), 3.81-3.86 (m, 1H), 3.90-3.94 (m, 1H), 4.18-4.27 (m, 1H), 5.34 (t, J=5.4 Hz, 1H), 6.21 (t, J=6.6 Hz, 1H), 6.34 (d, J=6.6 Hz, 1H), 7.15-7.23 (m, 2H), 7.27 (d, J=7.2 Hz, 1H), 7.39 (d, J=7.8 Hz, 1H), 8.32 (d, J=7.8 Hz, 1H), 11.25 (brs, 1H).

$^{13}$C NMR (600 MHz, DMSO-$d_6$): δ 22.4, 22.7, 26.6, 29.4, 59.0, 68.6 (t, J=22.1 Hz), 81.3, 84.4 (t, J=30.9 Hz), 96.6, 123.2 (t, J=257.1 Hz), 125.3, 131.6, 134.7, 135.6, 137.7, 145.0, 154.4, 163.5, 170.3.

MS-ESI (m/z): calcd for $C_{20}H_{21}F_2N_3O_5[M+Na]^+$ 444.1. found 444.1.

Compound 10: N-(1-((4R,5R)-3,3-difluoro-4-hydroxy-5-(hydroxymethyl)tetrahydrofuran-2-yl)-2-oxo-1,2-dihydropyrimidin-4-yl)-6-methoxy-2-naphthamide

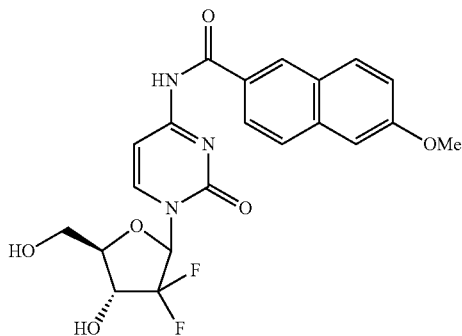 [SMILES: COc1ccc2cc(C(=O)Nc3ccn(C4O[C@H](CO)[C@@H](O)C4(F)F)c(=O)n3)ccc2c1]

$^1$H NMR (600 MHz, DMSO-$d_6$): δ 3.66-3.72 (m, 1H), 3.81-3.87 (m, 1H), 3.90-3.95 (m, 4H), 4.17-4.28 (m, 1H), 5.41 (t, J=5.4 Hz, 1H), 6.22 (t, J=7.2 Hz, 1H), 6.42 (d, J=6.6 Hz, 1H), 7.27 (d, J=9.0 Hz, 1H), 7.42 (brs, 1H), 7.46 (d, J=7.2 Hz, 1H), 7.90-7.94 (m, 1H), 7.96-8.0 (m, 2H), 8.34 (d, J=7.8 Hz, 1H), 8.64 (s, 1H), 11.38 (brs, 1H).

$^{13}$C NMR (600 MHz, DMSO-$d_6$): δ 55.7, 59.0, 68.6 (t, J=22.5 Hz), 81.2, 84.4 (t, J=32.3 Hz), 97.0, 106.2, 119.9, 123.2 (t, J=256.5 Hz), 125.3, 127.1, 127.4, 127.9, 129.9, 131.2, 136.9, 144.9, 154.5, 159.5, 164.0, 167.6.

MS-ESI (m/z): calcd for $C_{21}H_{19}F_2N_3O_6[M+Na]^+$ 470.1. found 470.1.

Compound 11: N-(1-((4R,5R)-3,3-difluoro-4-hydroxy-5-(hydroxymethyl)tetrahydrofuran-2-yl)-2-oxo-1,2-dihydropyrimidin-4-yl)-2,3-dihydro-1H-indene-2-carboxamide

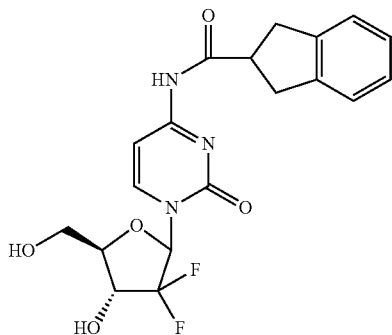 [SMILES: O=C(Nc1ccn(C2O[C@H](CO)[C@@H](O)C2(F)F)c(=O)n1)C1Cc2ccccc2C1]

$^1$H NMR (600 MHz, DMSO-$d_6$): δ 3.09-3.23 (m, 4H), 3.54 (quin, J=16.8, 8.4 Hz, 1H), 3.64-3.70 (m, 1H), 3.79-3.85 (m, 1H), 3.88-3.93 (m, 1H), 4.16-4.25 (m, 1H), 5.31 (t, J=4.8 Hz, 1H), 6.20 (t, J=6.6 Hz, 1H), 6.33 (d, J=6.0 Hz, 1H), 7.12-7.17 (m, 2H), 7.19-7.24 (m, 2H), 7.32 (d, J=7.2 Hz, 1H), 8.27 (d, J=7.8 Hz, 1H), 11.20 (s, 1H).

$^{13}$C NMR (600 MHz, DMSO-$d_6$): δ 36.0, 36.1, 45.2, 55.1, 59.0, 68.6 (t, J=22.1 Hz), 81.2, 84.4 (t, J=33.2 Hz), 96.2, 123.2 (t, J=257.1 Hz), 124.4, 126.7, 141.6, 141.7, 145.1, 154.4, 163.3, 176.0.

MS-ESI (m/z): calcd for $C_{19}H_{19}F_2N_3O_5[M+Na]^+$ 430.1. found 430.1.

Compound 12: N-(1-((4R,5R)-3,3-difluoro-4-hydroxy-5-(hydroxymethyl)tetrahydrofuran-2-yl)-2-oxo-1,2-dihydropyrimidin-4-yl)-2,3-dihydro-1H-indene-5-carboxamide

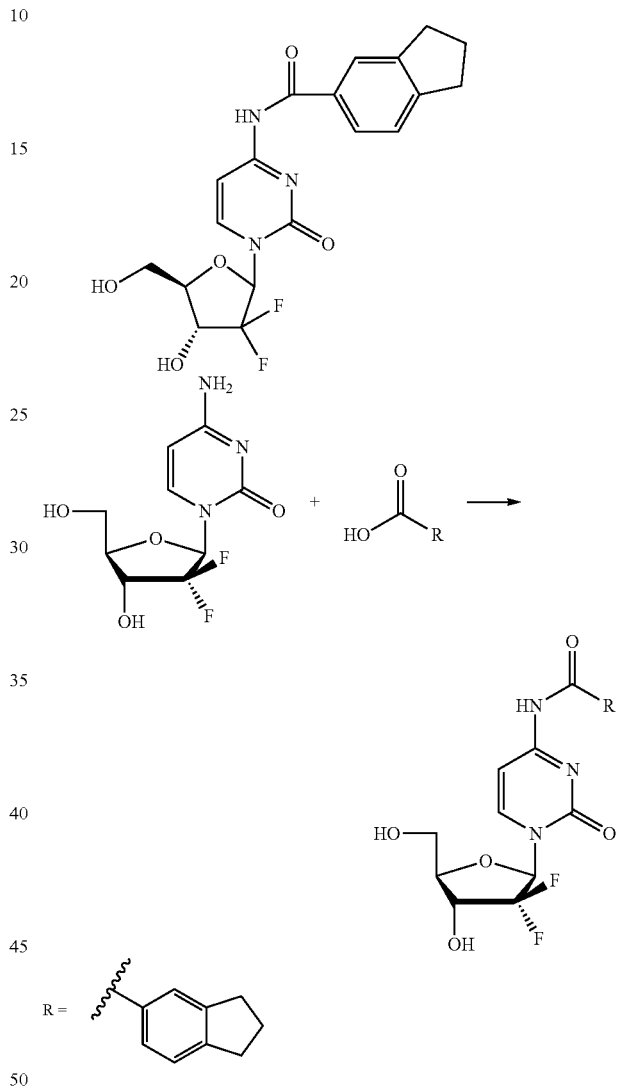

Scheme 2. Reagents and Conditions:
NMM (4-methylmorpholine), HOBt, EDCl.HCl, DMF/DMSO (3:1), 55° C., 24 h.

To a stirred solution of gemcitabine (0.22 g, 0.84 mmol) in DMF/DMSO (3:1) (4 mL) was added NMM (85 mg, 0.84 mmol), HOBt (114 mg, 0.84 mmol), EDCl.HCl (0.21 g, 1.09 mmol) and carboxyl acid (1.1 eq.) at room temperature and stirred for 24 hours at 55° C. The reaction mixture was cooled to rt, then added 10 mL H$_2$O slowly. The mixture was extracted with ethyl acetate (3×10 mL). The combined organic layers were dried over Na$_2$SO$_4$, filtered and concentrated on rotary evaporator to get the crude product which was purified with silica gel column chromatography (1-10%) methanol in DCM and then purified by preparative HPLC using 30-100% water/acetonitrile solvent system.

$^1$H NMR (600 MHz, DMSO-$d_6$): δ 2.06 (quin, J=14.4, 7.2 Hz, 2H), 2.92 (q, J=7.2, 6.0 Hz, 4H), 3.65-3.71 (m, 1H), 3.80-3.86 (m, 1H), 3.90-3.94 (m, 1H), 4.18-4.27 (m, 1H), 5.34 (t, J=5.4 Hz, 1H), 6.22 (t, J=7.2 Hz, 1H), 6.34 (d, J=6.6 Hz, 1H), 7.35 (d, J=8.4 Hz, 1H), 7.39-7.45 (m, 1H), 7.80 (d, J=7.8 Hz, 1H), 7.88 (s, 1H), 8.31 (d, J=7.2 Hz, 1H), 11.24 (s, 1H).

$^{13}$C NMR (600 MHz, DMSO-d$_6$): δ 25.2, 32.2, 32.6, 59.0, 68.6 (t, J=22.2 Hz), 81.2, 84.4 (t, J=30.0 Hz), 96.9, 123.2 (t, J=257.3 Hz), 124.4, 124.7, 127.1, 131.3, 144.4, 144.8, 149.7, 154.4, 164.0, 167.8.

MS-ESI (m/z): calcd for $C_{19}H_{19}F_2N_3O_5$[M+Na]$^+$ 430.1. found 430.1.

Example 3, IC$_{50}$ and TC$_{50}$ Assays for Antiviral Activity

The following procedures were used to determine the antiviral activity of various disclosed compounds.

A. Experimental Procedures for IC$_{50}$ Assay

Huh7 cells containing the HCV luciferase replicon were maintained at 37° C. in a humidified atmosphere at 5% CO$_2$ in Dulbecco's modified Eagle's medium (DMEM) containing 10% fetal bovine serum (FBS) and 250 µg/mL G418. To determine the IC$_{50}$ of each compound for the inhibition of the HCV luciferase replicon, these cells were first seeded in 96-well plates at 10,000 cells/well, and the plates were incubated at 37° C. for 24 h to allow for cell attachment. The cells were then treated with each compound at final concentrations ranging from 500 µM to 0 µM in triplicate in DMEM media containing 2% FBS and 0.5% dimethyl sulfoxide (DMSO). After 48 h of treatment at 37° C., the media in each well was removed, the cells were gently washed once with phosphate buffered saline (PBS) and subsequently lysed by the addition of Glo Lysis Buffer (Promega). After a 15 min incubation at room temperature to allow for complete cell lysis, Bright-Glo luciferase reagent (Promega) was added to each well and the relative luciferase activity in each well was determined by using a Glowmax 96 microplate luminometer (Promega). The relative luciferase activity detected in each well was then plotted as a function of compound concentration, and the data were then fit to the following 4 parameter logistic equation by using Kaleidagraph (Synergy Software):

$$y = \frac{\text{Bottom Plateau} + (\text{Top Plateau} - \text{Bottom Plateau})}{\left(1 + \left(\frac{x}{IC_{50}}\right)\right)^{Slope}}$$

where y is the relative luciferase activity detected, Bottom Plateau is the lowest relative luciferase activity detected, Top Plateau is the relative luciferase activity in cells that were not treated with compound, x is the compound concentration, IC$_{50}$ is the concentration of the compound at which the luciferase activity is reduced by 50%, and Slope is the slope of the curve.

IC$_{50}$ values determined using the above methods for inhibition of the HCV luciferase replicon in Huh7 cells are set forth in Table 1.

B. Experimental Procedures for TC$_{50}$ Assay

Huh7 cells were maintained at 37° C. in a humidified atmosphere at 5% CO$_2$ in DMEM containing 10% FBS. To determine the TC$_{50}$ of each compound, Huh7 cells were first seeded in 96-well plates at 5,000 cells/well, and the plates were incubated at 37° C. for 24 h to allow for cell attachment. The cells were then treated with each compound at concentrations ranging from 500 µM to 0 µM in triplicate in DMEM media containing 2% FBS and 0.5% DMSO and without phenol red. After 48 h of treatment at 37° C., the relative number of living cells in each well was determined by using the CellTiter 96 system (Promega) according to the manufacturer's instructions. The 3-(4,5-dimethylthiazol-2-yl)-5-(3-carboxymethoxyphenyl)-2-(4-sulfophenyl)-2H-tetrazolium (MTS) and phenazine methosulfate (PMS) reagents were added to each well of the 96-well plate and the plate was incubated at 37° C. for approximately 2 h. The absorbance at 490 nm and 650 nm in each well was then determined by using a Flexstation 3 microplate reader (Molecular Dynamics). The absorbance determined at 650 nm was then subtracted from the absorbance determined at 490 nm to correct for light scattering. The corrected absorbance values representing the relative number of live cells in each condition were then plotted as a function of compound concentration, and the data were then fit to the following sigmoidal E$_{max}$ equation by using Kaleidagraph:

$$y = (E_{max} \ast x^{Slope}) / (TC_{50}^{Slope} + x^{Slope})$$

where y is the relative corrected absorbance value, E$_{max}$ is the maximum relative inhibition, x is the compound concentration, TC$_{50}$ is the concentration of the compound at which the total cell population is reduced by 50%, and Slope is the slope of the curve.

TC$_{50}$ values determined using the above described methods in Huh7 cells are set forth in Table 1.

C. Antiviral IC$_{50}$ and TC$_{50}$ Data for Representative Disclosed Compounds The IC$_{50}$ and TC$_{50}$ data obtained using the methods described above for Compounds 1-4, their non-phosphorylated analogs, and gemcitabine are summarized in Table 1 below. The data in Table 1 were determined for cells exposed to drug for 48 h. The IC$_{50}$ is the concentration of each compound necessary to inhibit the replication of the HCV luciferase replicon to 50%. "TC$_{50}$," refers to toxic concentration necessary to reduce the cell population by 50%. All compounds were purified by HPLC.

TABLE 1

Antiviral Activity Of Gemcitabine And Gemcitabine Analogs.

| Compound | Structure | IC$_{50}$ (nM) | TC$_{50}$ (µM) | Therapeutic Index (TC$_{50}$/IC$_{50}$) |
|---|---|---|---|---|
| Gemcitabine | 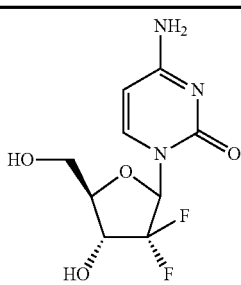 | 58 ± 6 | 35 ± 12 | 597 |

TABLE 1-continued

Antiviral Activity Of Gemcitabine And Gemcitabine Analogs.

| Compound | Structure | IC$_{50}$ (nM) | TC$_{50}$ (µM) | Therapeutic Index (TC$_{50}$/IC$_{50}$) |
|---|---|---|---|---|
| Compound 1 | 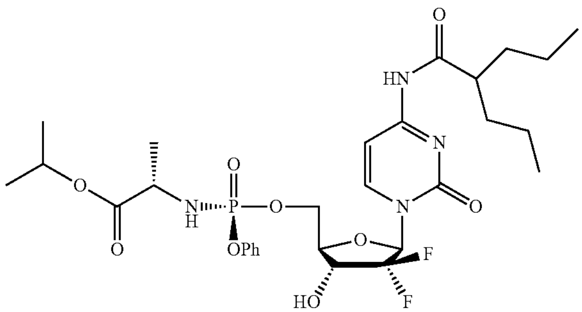 | 88.4 ± 13.3 | 17.4 ± 3.4 | 198 |
| Non-phosphorylated analog of Compound 1 | 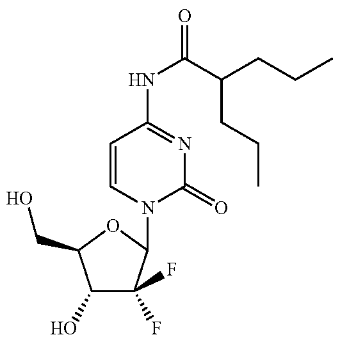 | 451 ± 79 | 383 ± 51 | 850 |
| Compound 2 | 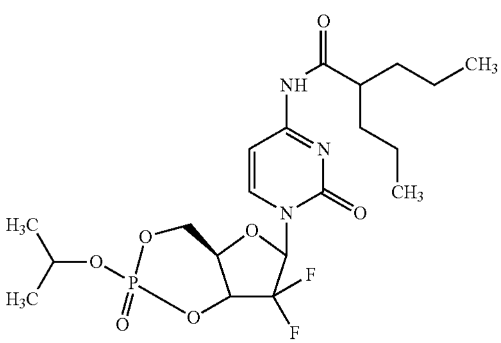 | 7,480 ± 1,060 | 175 ± 23 | 23.4 |
| Non-phosphorylated analog of Compound 2 | 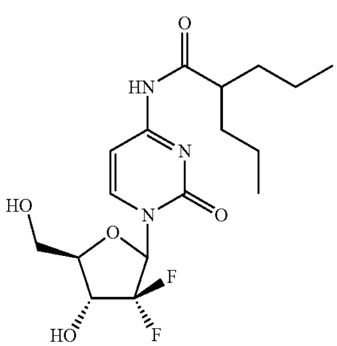 | 451 ± 79 | 383 ± 51 | 850 |

TABLE 1-continued

Antiviral Activity Of Gemcitabine And Gemcitabine Analogs.

| Compound | Structure | $IC_{50}$ (nM) | $TC_{50}$ (μM) | Therapeutic Index ($TC_{50}/IC_{50}$) |
|---|---|---|---|---|
| Compound 3 | 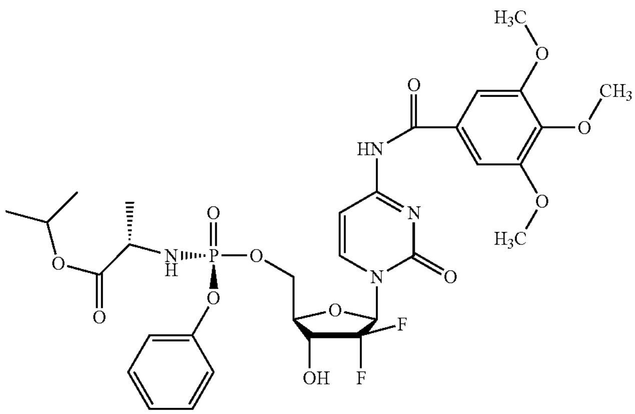 | 274 ± 80 | 57.5 ± 11.6 | 210 |
| Non-phosphorylated analog of Compound 3 | 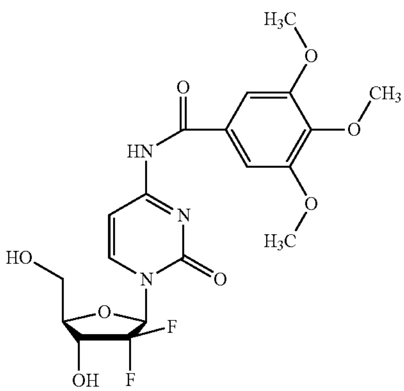 | 49.3 ± 8.8 | 495 ± 97 | 10040 |
| Compound 4 | 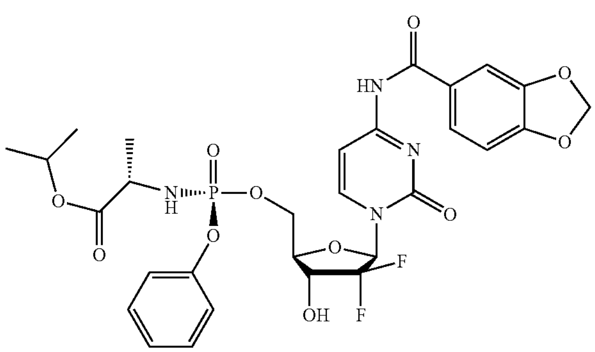 | 309 ± 45 | 41.45 ± 5.6 | 134 |
| Non-phosphorylated analog of Compound 4 | 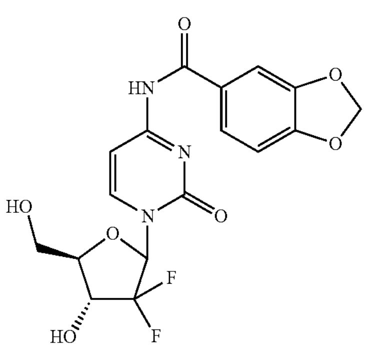 [SMILES: O=C(Nc1ccn(C2O[C@H](CO)[C@@H](O)C2(F)F)c(=O)n1)c1ccc2c(c1)OCO2] | 59.8 ± 8.4 | 473 ± 74 | 7910 |

TABLE 1-continued

Antiviral Activity Of Gemcitabine And Gemcitabine Analogs.

| Compound | Structure | IC$_{50}$ (nM) | TC$_{50}$ (μM) | Therapeutic Index (TC$_{50}$/IC$_{50}$) |
|---|---|---|---|---|
| Compound 13 | 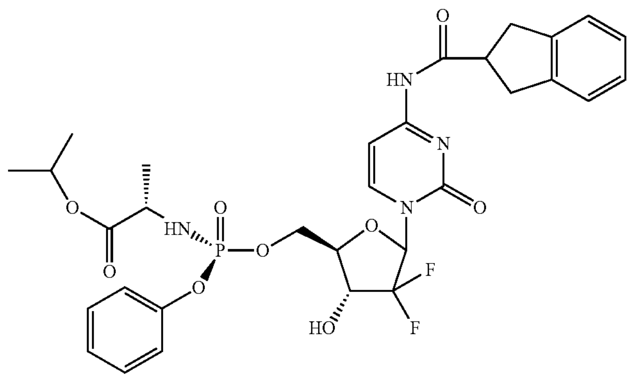 [SMILES: CC(C)OC(=O)[C@H](C)N[P@](=O)(OC[C@H]1OC(n2ccc(NC(=O)C3Cc4ccccc4C3)nc2=O)C(F)(F)[C@@H]1O)Oc1ccccc1] | 345 +/− 142 | 236 +/− 73 | 684 |

The IC$_{50}$ and TC$_{50}$ data obtained using the methods described above for additional gemcitabine analog compounds of formula (V) are summarized in Table 1A below.

TABLE 1A

Antiviral Activity Of Gemcitabine Analogs.

| Compound | Structure | IC$_{50}$ (nM) | TC$_{50}$ (μM) | Therapeutic Index (TC$_{50}$/IC$_{50}$) |
|---|---|---|---|---|
| Compound 5 | 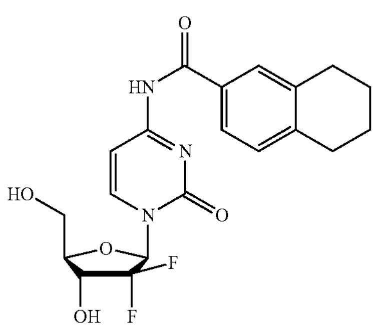 | 86.0 +/− 26.5 | 132 +/− 40 | 1,535 |
| Compound 6 | 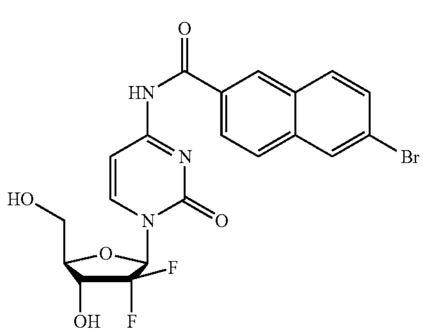 | 185 +/− 15 | 74 +/− 43 | 400 |

TABLE 1A-continued

Antiviral Activity Of Gemcitabine Analogs.

| Compound | Structure | $IC_{50}$ (nM) | $TC_{50}$ (μM) | Therapeutic Index ($TC_{50}/IC_{50}$) |
| --- | --- | --- | --- | --- |
| Compound 7 | 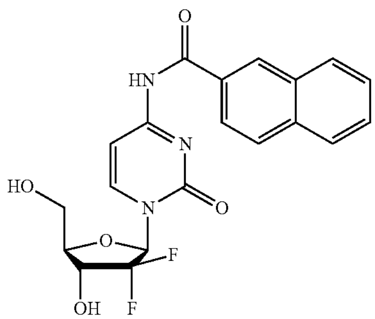 | 126 +/− 16 | 125 +/− 27 | 992 |
| Compound 8 | 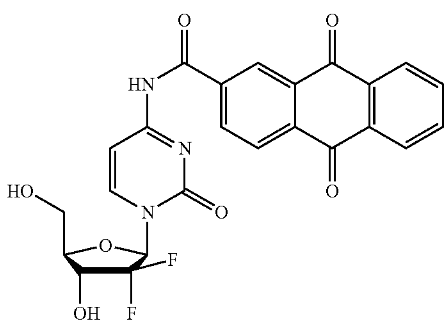 | 12.8 +/− 0.7 | 249 +/− 86 | 19,450 |
| Compound 9 | 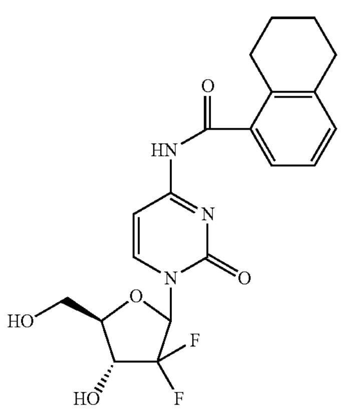 [SMILES: O=C(Nc1ccn(C2O[C@H](CO)[C@@H](O)C2(F)F)c(=O)n1)c1cccc2c1CCCC2] | 161 +/− 46 | 92 +/− 39 | 571 |
| Compound 10 | 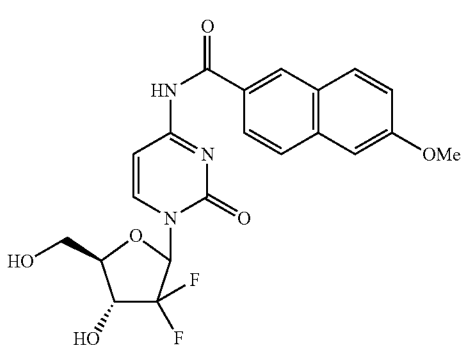 [SMILES: COc1ccc2cc(C(=O)Nc3ccn(C4O[C@H](CO)[C@@H](O)C4(F)F)c(=O)n3)ccc2c1] | 93.5 +/− 18.2 | 168 +/− 31 | 1,796 |

TABLE 1A-continued

Antiviral Activity Of Gemcitabine Analogs.

| Compound | Structure | $IC_{50}$ (nM) | $TC_{50}$ (μM) | Therapeutic Index ($TC_{50}/IC_{50}$) |
|---|---|---|---|---|
| Compound 11 | 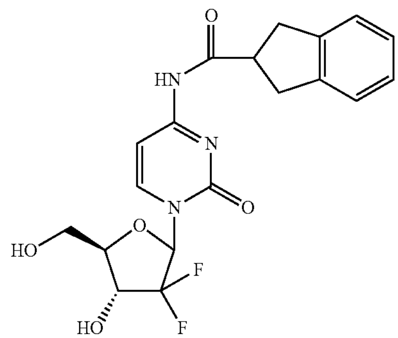 [SMILES: O=C(Nc1ccn(C2O[C@H](CO)[C@@H](O)C2(F)F)c(=O)n1)C1Cc2ccccc2C1] | 10.0 +/− 0.9 | >500 | >50,000 |
| Compound 12 | 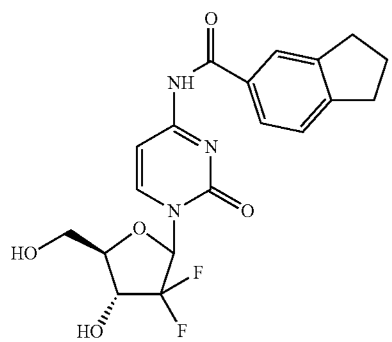 [SMILES: O=C(Nc1ccn(C2O[C@H](CO)[C@@H](O)C2(F)F)c(=O)n1)c1ccc2c(c1)CCC2] | 58.6 +/− 24.5 | 378 +/− 119 | 6,451 |

All of these compounds were effective inhibitors and surprisingly potent in the HCV replicon assays.

Example 4, $TC_{50}$ Assays with Human Cancer Cell Lines

Huh7, HEPG2, HEK293, MCF-7 and BxPC3 cell lines were maintained at 37° C. in a humidified atmosphere at 5% $CO_2$ in DMEM containing 10% FBS. To determine the $TC_{50}$ of each compound in these cell lines at 96 h after treatment, these cell lines were first seeded in 96-well plates at 1,000 cells/well, and the plates were incubated at 37° C. for 24 h to allow for cell attachment. The cells were then treated with each compound at concentrations ranging from 500 μM to 0 μM in triplicate in DMEM media containing 2% FBS and 0.5% DMSO and without phenol red. After 96 h of treatment at 37° C., the $TC_{50}$ value of each compound was then determined by using the $TC_{50}$ assay procedures described above.

The data obtained by methods described herein after 96 h of test drug treatment above are summarized in Table 2.

TABLE 2

Toxicity Of Gemcitabine And Its Analogs In Human Cancer Cell Lines.

| Compound | Huh7 (μM) | HEPG2 (μM) | HEK293 (μM) | MCF-7 (μM) | BxPC3 (μM) |
|---|---|---|---|---|---|
| Gemcitabine | 3.41 ± 1.36 | 0.311 ± 0.055 | 0.56 ± 0.13 | 0.067 ± 0.014 | 0.0029 ± 0.003 |
| Phosphorylated analog of Gemcitabine | 4.15 +/− 0.88 | 0.89 +/− 0.14 | 0.38 +/− 0.06 | 0.115 +/− 0.017 | 0.76 +/− 0.50 |
| Compound 1 | 3.28 ± 0.57 | 1.31 ± 0.21 | 4.10 ± 0.50 | 1.76 ± 0.67 | 7.01 ± 0.97 |
| Non-phosphorylated analog of Compound 1 | 3.89 ± 0.68 | 4.32 ± 0.34 | 15.1 ± 1.77 | 9.06 ± 1.95 | 1.02 ± 0.15 |
| Compound 3 | 8.37 +/− 0.90 | 1.57 +/− 0.38 | 1.10 +/− 0.09 | 0.683 +/− 0.123 | 4.07 +/− 1.03 |
| Non-phosphorylated analog of Compound 3 | 5.05 +/− 1.22 | 1.67 +/− 0.42 | 1.28 +/− 0.26 | 0.566 +/− 0.118 | 1.83 +/− 0.43 |
| Compound 4 | 5.50 +/− 0.96 | 3.22 +/− 0.60 | 2.70 +/− 0.37 | 1.93 +/− 0.31 | 4.05 +/− 0.91 |
| Non-phosphorylated analog of Compound 4 | 7.04 +/− 1.42 | 2.81 +/− 0.53 | 4.09 +/− 0.73 | 1.19 +/− 0.33 | 0.72 +/− 0.18 |

Example 5, TC$_{50}$ Assays in Gemcitabine Resistant Cancer Cells

PK9 and RPK9 cells were maintained at 37° C. in a humidified atmosphere at 5% CO$_2$ in Roswell Park Memorial Institute (RPMI) media containing 10% FBS. To determine the TC$_{50}$ of each compound in these cell lines at 48 h after treatment, these cell lines were first seeded in 96-well plates at 2,500 cells/well, and the plates were incubated at 37° C. for 24 h to allow for cell attachment. The cells were then treated with each compound at concentrations ranging from 500 M to 0 μM in triplicate in RPMI media containing 2% FBS and 0.5% DMSO and without phenol red. After 48 h of treatment at 37° C., the TC$_{50}$ value of each compound was then determined by using the TC$_{50}$ assay procedures described above. The RPK9 cells were derived from the parental PK9 cell line, and are deficient for dCK activity due to the partial deletion of the dCK gene. Phosphorylation by dCK is an essential step within the gemcitabine activation pathway (FIG. 1). Without wishing to be bound by a particular theory, we predict that dCK activity will not be required for the activation of Compound 1, or nucleoside analogs bearing the disclosed 5'phosphoramidite moiety. The resulting data is set forth in Table 3:

TABLE 3

Cytotoxicity Of Gemcitabine And Gemcitabine Analogs in PK9 and RPK9 Cells.

| Compound | Structure | TC$_{50}$ (μM) in PK9 cells at 48 hr | TC$_{50}$ (μM) in RPK9 cells at 48 hr |
|---|---|---|---|
| Gemcitabine | 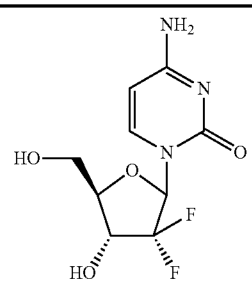 | 0.095 ± 0.035 | >500 |
| Phosphorylated analog of Gemcitabine | 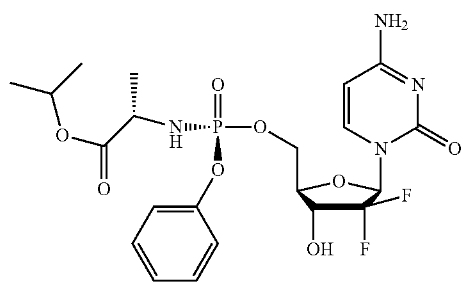 | 11.2 +/− 1.5 | 21.0 +/− 4.6 |
| Compound 1 | 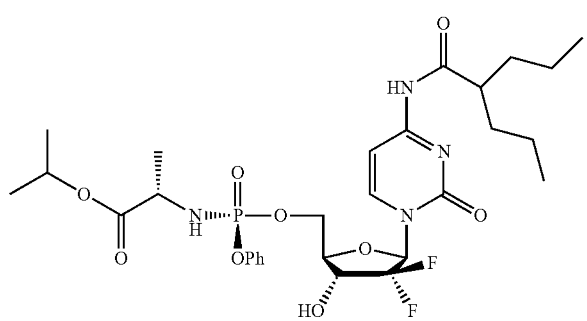 | 25.2 ± 13.6 | 24.2 ± 6.4 |
| Non-phosphorylated analog of Compound 1 | 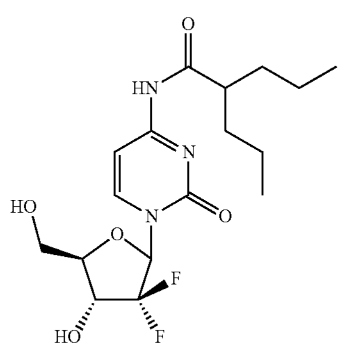 | 1.27 ± 0.09 | >500 |

TABLE 3-continued

Cytotoxicity Of Gemcitabine And Gemcitabine Analogs in PK9 and RPK9 Cells.

| Compound | Structure | $TC_{50}$ (μM) in PK9 cells at 48 hr | $TC_{50}$ (μM) in RPK9 cells at 48 hr |
| --- | --- | --- | --- |
| Compound 2 | 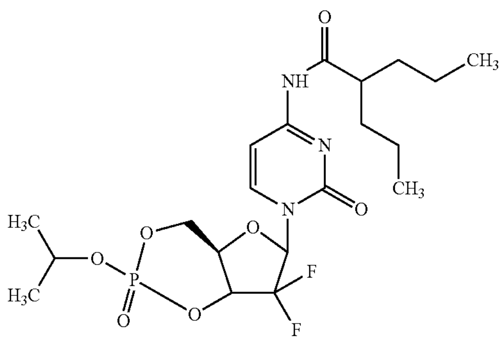 | 716 ± 104 | 537 ± 55 |
| Non-phosphorylated analog of Compound 2 | 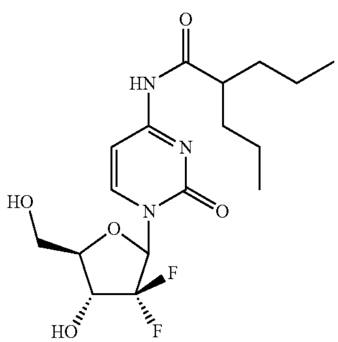 | 1.27 ± 0.09 | >500 |
| Compound 3 | 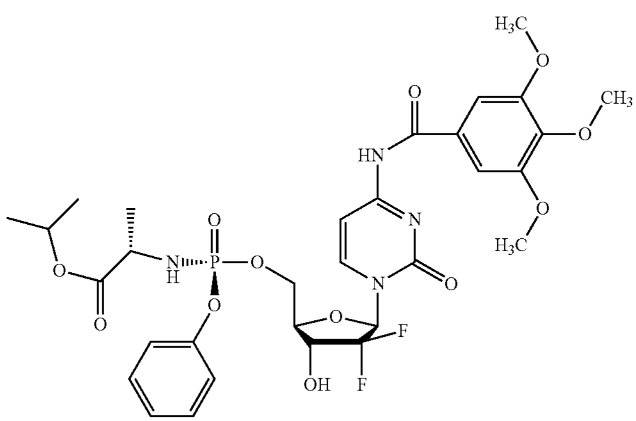 | 18.5 ± 11.9 | 24.2 ± 4.2 |
| Non-phosphorylated analog of Compound 3 | 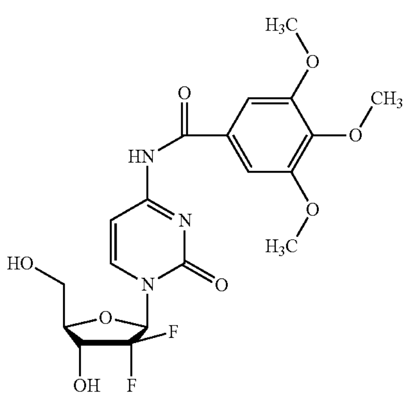 | 1.69 ± 0.10 | >500 |

TABLE 3-continued

Cytotoxicity Of Gemcitabine And Gemcitabine Analogs in PK9 and RPK9 Cells.

| Compound | Structure | $TC_{50}$ (µM) in PK9 cells at 48 hr | $TC_{50}$ (µM) in RPK9 cells at 48 hr |
| --- | --- | --- | --- |
| Compound 4 | 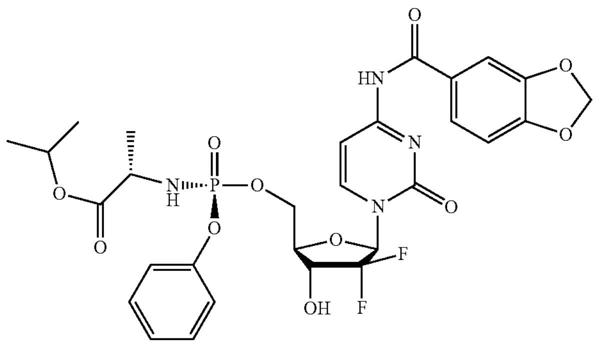 | 16.0 ± 4.8 | 20.3 ± 3.9 |
| Non-phosphorylated analog of Compound 4 | 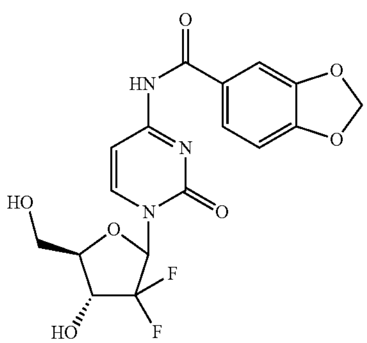 [SMILES: O=C(Nc1ccn(C2O[C@H](CO)[C@@H](O)C2(F)F)c(=O)n1)c1ccc2c(c1)OCO2] | 1.63 ± 0.10 | >500 |

Example 6, Time Course of Huh7 Cell Cytotoxicity

Figure 2:
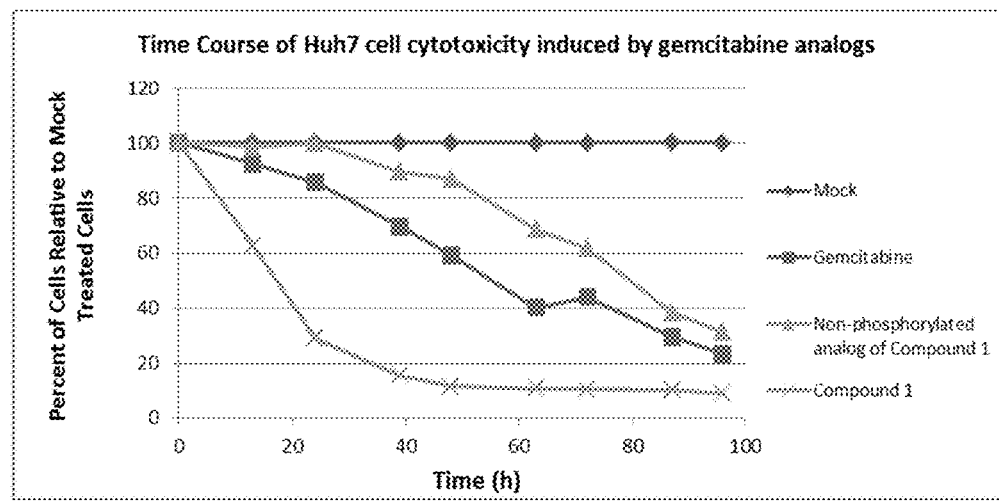
FIG. 2 discloses the results of a time course study as described in the Example 6 wherein Huh7 cells were treated with media alone, gemcitabine (50 μM), or the indicated gemcitabine analog (50 μM). After various treatment times, the cells were assayed for cell proliferation by using the CellTiter 96 kit (Promega). The relative number of live cells under each condition at each time point is plotted as a percent of the relative number of mock treated cells.

To determine cytotoxic effect of these compounds over time, Huh7 cells were first seeded in 96-well plates at 1,000 cells/well, and the plates were incubated at 37° C. for 24 h to allow for cell attachment. At various times, cells were treated in triplicate by replacing the media with media containing no drug (mock), 50 µM gemcitabine or 50 µM of the indicated nucleoside analog. At 96 h after treating the first set of wells, the number of living cells in each well was determined by using the CellTiter 96 system (Promega) as described above. The percent of live cells remaining after each drug treatment relative to the corresponding mock treated control were then plotted as a function of total drug treatment time (FIG. 2).

Huh7 cells were mock treated or treated with 50 µM of gemcitabine, 50 µM Compound 1 or 50 µM of the non-phosphorylated analog of Compound 1. The percent of viable cells relative to the mock treated cells at various time points over the course of 96 hours was determined. The data obtained are shown in FIG. 2.

Example 7, Cell Transport

Gemcitabine is known to enter cells principally through Equilibrative Nucleoside Transporter 1 (ENT1). Loss of ENT1 transporter activity results in gemcitabine resistance. To determine if the nucleoside analog prodrugs utilize the ENT1 transporter for cell entry, a cytotoxicity assay was performed in the presence of the ENT1 inhibitor S-(4-Nitrobenzyl)-6-thioinosine (NBTI). To this end, Huh7 cells or PK9 cells were seeded in 96-well plates at a density of 5,000 cells/well or 2,500 cells/well, respectively, and the plates were incubated at 37° C. for 24 h to allow for cell attachment. The media was then removed from the plates and replaced with media containing 2% FBS, 0.5% DMSO and 10 µM NBTI. The cells were then incubated at 37° C. for 1 h to allow for inhibition of the ENT1 transporter. Subsequently, the cells were treated with each compound at final concentrations ranging from 500 µM to 0 µM in triplicate in media containing 2% FBS, 0.5% DMSO and 10 µM NBTI. After 48 h of treatment at 37° C., the $TC_{50}$ value of each nucleoside analog was then determined by using the $TC_{50}$ assay procedures described above. The $TC_{50}$ values of each compound in the presence or absence of the ENT1 inhibitor were then compared. The results are set forth in Table 4.

TABLE 4

Comparison of the cytotoxicity of gemcitabine and the gemcitabine analogs after 48 hours of treatment of Huh7 or PK9 cells in the presence of 10 μM of the ENT1 transporter inhibitor NBTI.

| Compound | $TC_{50}$ (μM) in Huh7 cells at 48 h | | $TC_{50}$ (μM) in PK9 cells at 48 h | |
| --- | --- | --- | --- | --- |
| | Without NBTI | With NBTI | Without NBTI | With NBTI |
| Gemcitabine | 35 +/− 12 | >500 | 0.095 +/− 0.035 | 1.92 +/− 0.78 |
| Compound 1 | 17.4 +/− 3.4 | 16.4 +/− 3.5 | 25.2 +/− 13.6 | 16.9 +/− 6.8 |
| Non-phosphorylated analog of compound 1 | 383 +/− 51 | 260 +/− 45 | 1.27 +/− 0.09 | 6.6 +/− 2.5 |

Without wishing to be bound by a particular theory, we conclude that Compound 1, non-phosphorylated analogs of Compound 1, and nucleoside analogs similar to either Compound 1 or non-phosphorylated analogs of Compound 1 do not require the ENT1 transporter for cell entry. And thus, cells that have lost the ENT1 transporter activity will not be resistant to the disclosed nucleoside analogs.

Example 8, pH Stability

In order for a prodrug to be orally bioavailable, it must be stable over a wide range of pH values. To assess the pH stability of the phosphoramidite gemcitabine analogs, Compound 1 was diluted to 200 μM in buffered solutions with pH values of 1.0 to 8.0 and incubated at 40° C. for 4 h. The relative amount of intact prodrug was then determined by first separating the intact prodrug from any potential degradation products by using reverse-phase high performance liquid chromatography (HPLC) and subsequently quantifying the relative amount of remaining prodrug by uv spectrophotometry. The results for Compound 1 are set forth in Table 5.

TABLE 5 pH stability of Compound 1 treated in aqueous buffer at 40° C. for 4 hours.

| Condition | % of Compound 1 remaining |
| --- | --- |
| Pretreatment | 100 |
| pH 1 | 58 |
| pH 2 | 85 |
| pH 4 | 92 |

TABLE 5-continued pH stability of Compound 1 treated in aqueous buffer at 40° C. for 4 hours.

| Condition | % of Compound 1 remaining |
| --- | --- |
| pH 6 | 100 |
| pH 8 | 47 |

We conclude that gemcitabine analogs like Compound 1 are stable at a wide range of pH values. This wide range of pH stability is consistent with the hypothesis that the gemcitabine analogs will be orally bioavailable.

Example 9, Synergism of Disclosed Compounds with Other Antiviral Compounds

Isobologram analysis was conducted to assess the potential synergistic interaction of representative disclosed compounds with representative antiviral compounds. The isobolgram analysis was conducted as previously described by Chou and Talalay (see Chou T. C. and Talalay P. "Analysis of combined drug effects: a new look at a very old problem." Trends Pharmacol Sci 1983; 4:450-4; and Chou T. C. and Talalay P. "Quantitative analysis of dose-effect relationships: the combined effects of multiple drugs or enzyme inhibitors." Adv Enzyme Regul 1984; 22:27-55; both of which are incorporated herein by reference in their entirety). The definitions of synergism are those described by Chou (see Chou, T. C. (2006) Theoretical basis, experimental design, and computerized simulation of synergism and antagonism in drug combination studies. Pharmacol Rev. 58(3):621-81, which is incorporated herein by reference in its entirety).

In the synergism studies described herein, the antiviral compound shown in Table 6 was assessed in combination with a representative disclosed compound, Compound 1.

TABLE 6

An approved anti-HCV drug in Japan and Europe.

| | Description |
| --- | --- |
| BMS-790052 | Other names: daclatasvir; carbamic acid, N,N'-[[1,1'-biphenyl]-4,4'-diylbis[1H-imidazole-5,2-diyl-(2S)-2,1-pyrrolidinediyl[(1S)-1-(1-methylethyl)-2-oxo-2,1-ethanediyl]]]bis-, C,C'-dimethyl ester |
| | Structure: 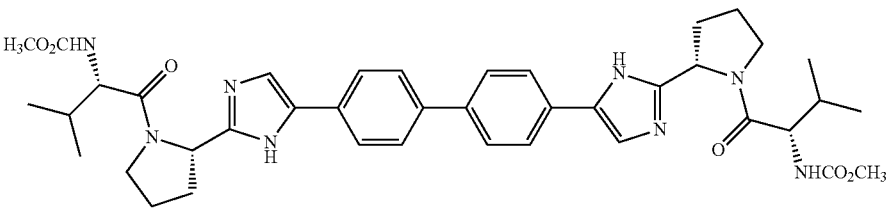 |

Figure 3:
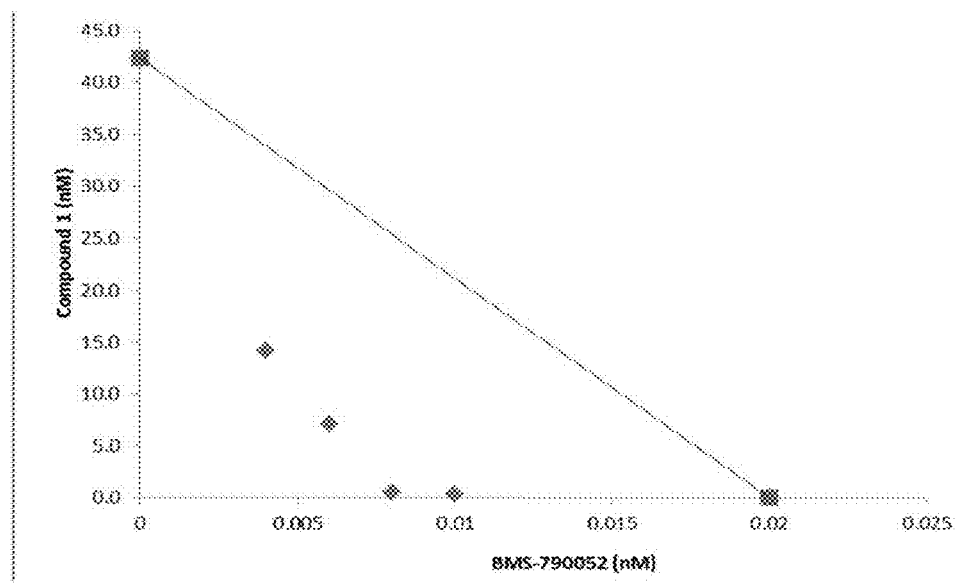
FIG. 3 discloses representative data for $IC_{50}$ isobologram analysis of Compound 1 and BSM-790052.

The test compound concentrations and corresponding combination index (with associated level of synergism) are shown in Table 7. The resulting isobologram analysis is depicted in FIG. 3. The data show that BMS-790052, an NS5A inhibitor, appears to potentiate the activity of Compound 1, i.e., these two compounds show synergism in the inhibition of the HCV luciferase replicon. Without wishing to be bound by a particular theory, potentiation of the activity of a disclosed gemcitabine analog can result from co-treatment with a compound that inhibits a different HCV protein, e.g. NS5A, than the target of the disclosed gemcitabine analogs, i.e. the HCV RNA-dependent RNA polymerase.

TABLE 7

Isobologram Data

| Compound 1 (nM) | BMS-790052 (nM) | Combination Index | |
|---|---|---|---|
| 42.3 | 0 | 1.000 | |
| 14.2 | 0.004 | 0.535 | synergism |
| 7.1 | 0.006 | 0.468 | synergism |
| 0.4 | 0.008 | 0.410 | synergisn |
| 0.2 | 0.010 | 0.505 | synergism |
| 0.0 | 0.020 | 1.000 | |

Example 10, In Vivo Toxicology Assessment in Mice

All in vivo toxicology assays were performed with CD-1 ICR mice (female, 4-6 week old; 20-30 gram body weight). Compound 1 (Table 1) was first dissolved in Formulation I containing 5% dimethyl sulfoxide (DMSO), 20% solutol, 20% PEG 400, and 55% sodium phosphate (50 mM, pH 6.0). Five mice were administered with Compound 1 in Formulation I via oral gavage at a dosage of 20 mg/kg while two other mice were orally treated with Formulation I alone (no inhibitor). All of the seven mice showed no signs of toxicity during the seven day period of observation. After Day 7, these mice were sacrificed and showed that their internal organs were healthy with no abnormality.

Example 11, Oral Administration of Inhibitors to HCV-Infected Chimpanzees

Via oral gavage, two HCV-infected chimpanzees I (male, 56.49 kg and 11 years old; genotype 1b HCV) and II (male, 61.91 kg and 34 years old; genotype 1a HCV) each received a single dosage of 200 mg of Compound 1 in Formulation I while the HCV-infected chimpanzee III (male, 56.19 kg and 18 years old; genotype 1a HCV) was administered a single dosage of 260 mg of the non-phosphorylated analog of Compound 1 (Table 1) in Formulation I. After 12 hours, the HCV viral titer decreased from 24,100 to 10,200 IU/ml (or 58% drop) in Chimpanzee I, from 38,500 to 27,000 IU/ml (or 30% drop) in Chimpanzee II, and from 154,000 to 142,000 IU/ml (or 8% drop) in Chimpanzee III. These data indicates that Compound 1 was more effective than its non-phosphorylated analog in inhibiting HCV in chimpanzees. Notably, the animals were sedated with ketamine HCl to effect, approximately 5-15 mg/kg, prior to scheduled dosing and blood sample collection. All animals were fasted overnight prior to dosing and a minimum of 2 hours prior to scheduled blood sample collections. Viral load determinations were performed on plasma samples using the HCV TaqMan assay (COBAS® AmpliPrep/COBAS® TaqMan® HCV Test, Version 2, Test Code 1220) for quantitative analysis. Single oral dosages of Compound 1 (200 mg) and its non-phosphorylated analog (260 mg) in Hepatitis-C infected chimpanzees were well tolerated. There were no adverse effects, illness, nor distress seen with the three chimpanzees during the study requiring veterinarian intervention.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A compound of formula (I):

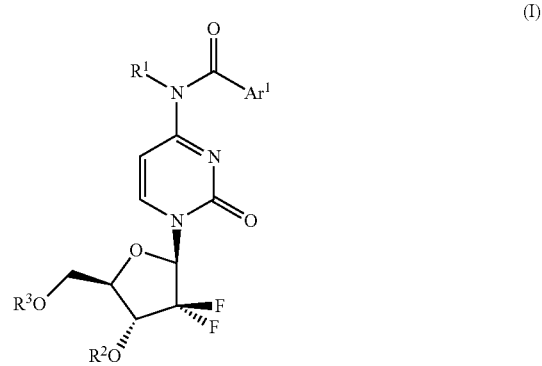

or a pharmaceutically acceptable salt, hydrate, solvate, or polymorph thereof, wherein:

$Ar^1$ is selected from phenyl, naphthyl, a bicyclic fused ring system or a polycyclic fused ring system,
  wherein the phenyl or naphthyl is substituted with 1, 2, 3, 4, or 5 groups independently selected from halo, cyano, nitro, hydroxy, thiol, —$NR^{9a}R^{9b}$, $C_1$-$C_6$ alkyl, $C_1$-$C_6$ monohaloalkyl, $C_1$-$C_6$ polyhaloalkyl, $C_1$-$C_6$ alkoxy, $C_1$-$C_6$ monohaloalkoxy, $C_1$-$C_6$ polyhaloalkoxy, $C_1$-$C_6$ hydroxyalkyl, $C_1$-$C_6$ alkylthiol, optionally substituted phenyl, optionally substituted benzyl, and optionally substituted phenoxy, —C(O)$R^{12}$, —C(O)O$R^{12}$, —C(O)NH$R^{12}$, —OC(O)$R^{12}$, —NHC(O)$R^{12}$, and —NHC(O)O$R^{12}$, in which each of $R^{9a}$ and $R^{9b}$ is independently selected from hydrogen, $C_1$-$C_4$ alkyl, and an amine protecting group, and $R^{12}$ is $C_1$-$C_6$ alkyl,
  wherein the bicyclic fused ring system or the polycyclic fused ring system comprises an aryl ring fused to one or more 4-, 5-, 6-, 7-, or 8-membered cycloalkyl or heterocycloalkyl or fused to a 4-, 5-, 6-, 7-, or 8-membered cycloalkyl or heterocycloalkyl which is fused to a second aryl ring,
  wherein the aryl rings of the bicyclic or polycyclic fused ring system are each independently selected from phenyl, pyridinyl, pyrimidinyl, pyridazinyl, pyrazinyl, and triazinyl,
  wherein the aryl rings of the bicyclic or polycyclic fused ring system are each optionally substituted with 1, 2, or 3 groups independently selected from halogen, —OH, —CN, —$NH_2$, thiol, $C_1$-$C_6$ alkyl, $C_1$-$C_6$ alkoxy, $C_1$-$C_6$ monohaloalkyl, $C_1$-$C_6$ polyhaloalkyl, $C_1$-$C_6$ alkylamino, and $C_1$-$C_6$ dialkylamino, wherein the cycloalkyl or heterocycloalkyl of the bicyclic fused ring system is optionally substituted with 1, 2, 3, 4, or 5 groups independently selected from halogen, —OH, —CN, —NH$_2$, thiol, oxo, $C_1$-$C_6$ alkyl, $C_1$-$C_6$ alkoxy, $C_1$-$C_6$ monohaloalkyl, $C_1$-$C_6$ polyhaloalkyl, $C_1$-$C_6$ alkylamino, $C_1$-$C_6$ dialkylamino, $C_1$-$C_6$ aminoalkyl, $C_1$-$C_6$ hydroxyalkyl, —(C=O)OR$^8$, and —(C=O)NR$^{9a}$R$^{9b}$, in which each R$^8$ is independently selected from hydrogen, $C_1$-$C_6$ alkyl, and a hydroxyl protecting group, and each of R$^{9a}$ and R$^{9b}$ is as defined above;

R$^1$ is selected from hydrogen, $C_1$-$C_4$ alkyl, and an amine protecting group; and R$^2$ is selected from hydrogen and a hydroxyl protecting group and R$^3$ is a moiety having a structure represented by formula (II):

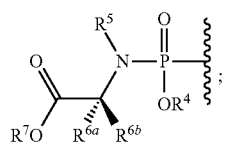

(II)

R$^4$ is selected from $C_1$-$C_6$ alkyl, $C_1$-$C_6$ monohaloalkyl, $C_1$-$C_6$ polyhaloalkyl, $C_2$-$C_8$ alkenyl, $C_2$-$C_8$ alkynyl, $C_3$-$C_8$ cycloalkyl, $C_2$-$C_8$ heterocycloalkyl, Ar$^2$, —($C_1$-$C_6$ alkyl)-($C_3$-$C_8$ cycloalkyl), —($C_1$-$C_6$ alkyl)-($C_2$-$C_8$ heterocycloalkyl), and —($C_1$-$C_6$ alkyl)-Ar$^2$;

R$^5$ is selected from hydrogen, $C_1$-$C_6$ alkyl, $C_1$-$C_6$ monohaloalkyl, $C_1$-$C_6$ polyhaloalkyl, $C_2$-$C_8$ alkenyl, $C_2$-$C_8$ alkynyl, $C_3$-$C_8$ cycloalkyl, $C_2$-$C_8$ heterocycloalkyl, Ar$^2$, —($C_1$-$C_6$ alkyl)-($C_3$-$C_8$ cycloalkyl), —($C_1$-$C_6$ alkyl)-($C_2$-$C_8$ heterocycloalkyl), and —($C_1$-$C_6$ alkyl)-Ar$^2$;

R$^{6a}$ and R$^{6b}$ are each selected from hydrogen, $C_1$-$C_6$ alkyl, $C_1$-$C_6$ monohaloalkyl, $C_1$-$C_6$ polyhaloalkyl, $C_2$-$C_8$ alkenyl, $C_2$-$C_8$ alkynyl, $C_3$-$C_8$ cycloalkyl, $C_2$-$C_8$ heterocycloalkyl, Ar$^2$, —($C_1$-$C_6$ alkyl)-($C_3$-$C_8$ cycloalkyl), —($C_1$-$C_6$ alkyl)-($C_2$-$C_8$ heterocycloalkyl), and —($C_1$-$C_6$ alkyl)-Ar$^2$, provided that each of R$^{6a}$ and R$^{6b}$ are not the same; and R$^7$ is selected from $C_1$-$C_6$ alkyl, $C_1$-$C_6$ monohaloalkyl, $C_1$-$C_6$ polyhaloalkyl, $C_2$-$C_8$ alkenyl, $C_2$-$C_8$ alkynyl, $C_3$-$C_8$ cycloalkyl, $C_2$-$C_8$ heterocycloalkyl, Ar$^2$, —($C_1$-$C_6$ alkyl)-($C_3$-$C_8$ cycloalkyl), —($C_1$-$C_6$ alkyl)-($C_2$-$C_8$ heterocycloalkyl), and —($C_1$-$C_6$ alkyl)-Ar$^2$, Ar$^2$ is an optionally substituted phenyl, naphthalene, monocyclic heteroaryl, bicyclic heteroaryl or polycyclic heteroaryl, or R$^2$ and R$^3$ together comprise a divalent moiety having a structure represented by formula (III):

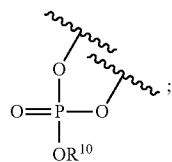

(III)

and

R$^{10}$ is selected from hydrogen, $C_1$-$C_6$ alkyl, $C_1$-$C_6$ monohaloalkyl, $C_1$-$C_6$ polyhaloalkyl, $C_2$-$C_8$ alkenyl, $C_2$-$C_8$ alkynyl, $C_3$-$C_8$ cycloalkyl, $C_2$-$C_8$ heterocycloalkyl, Ar$^2$, —($C_1$-$C_6$ alkyl)-($C_3$-$C_8$ cycloalkyl), —($C_1$-$C_6$ alkyl)-($C_2$-$C_8$ heterocycloalkyl), —($C_1$-$C_6$ alkyl)-Ar$^2$.

2. The compound of claim 1, wherein Ar$^1$ is the bicyclic or polycyclic fused ring system comprising an aryl ring fused to one or more 4-, 5-, 6-, 7-, or 8-membered cycloalkyl or heterocycloalkyl.

3. The compound of claim 2, wherein Ar$^1$ is phenyl fused to a 5-, 6-, 7-, or 8-membered heterocycloalkyl comprising 1 or 2 heteroatoms selected from O, S and N.

4. The compound of claim 3, wherein the heterocycloalkyl of the bicyclic fused ring system is optionally substituted with 1, 2 or 3 substituents independently selected from halogen, $C_1$-$C_6$ alkyl, $C_1$-$C_6$ monohaloalkyl, $C_1$-$C_6$ polyhaloalkyl, and —(C=O)OR$^8$ in which each R$^8$ is independently selected from hydrogen, $C_1$-$C_6$ alkyl, and a hydroxyl protecting group.

5. The compound of claim 1, wherein Ar$^1$ is a moiety having a structure represented by a formula:

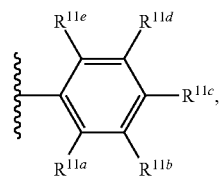

wherein R$^{11a}$ and R$^{11e}$ are independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted benzyl, optionally substituted phenoxy, nitro, —NH$_2$, —NH($C_1$-$C_4$ alkyl), and —N($C_1$-$C_4$ alkyl)$_2$;

wherein R$^{11b}$ and R$^{11d}$ are independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —NH$_2$, —NH($C_1$-$C_4$ alkyl), and —N($C_1$-$C_4$ alkyl)$_2$;

wherein R$^{11c}$ is selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, —C(O)R$^{12}$, —C(O)OR$^{12}$, —C(O)NHR$^{12}$, —OC(O)R$^{12}$, —NHC(O)R$^{12}$, and —NHC(O)OR$^{12}$, wherein R$^{12}$ is hydrogen, methyl, ethyl, propyl, butyl, pentyl, or hexyl; and wherein at least one of R$^{11a}$, R$^{11b}$, R$^{11c}$, R$^{11d}$, and R$^{11e}$ is not hydrogen.

6. The compound of claim 1, wherein Ar$^1$ is a moiety having a structure represented by a formula:

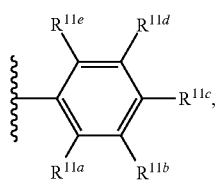

wherein each of $R^{11a}$, $R^{11b}$, $R^{11c}$, $R^{11d}$, and $R^{11e}$ is independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —NH$_2$, —NH(C$_1$-C$_4$ alkyl), and —N(C$_1$-C$_4$ alkyl)$_2$, —C(O)R$^{12}$, —C(O)OR$^{12}$, —C(O)NHR$^{12}$, —OC(O)R$^{12}$, —NHC(O)R$^{12}$, and —NHC(O)OR$^{12}$, wherein $R^{12}$ is hydrogen, methyl, ethyl, propyl, butyl, pentyl, or hexyl; and wherein at least two of $R^{11a}$, $R^{11b}$, $R^{11c}$, $R^{11d}$, and $R^{11e}$ are not hydrogen.

7. The compound of claim 6, wherein at least three of $R^{11a}$, $R^{11b}$, $R^{11c}$, $R^{11d}$, and $R^{11e}$ are not hydrogen.

8. The compound of claim 1, wherein $R^2$ is selected from hydrogen and a hydroxyl protecting group and $R^3$ is a moiety having a structure represented by formula (II):

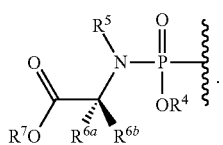

9. The compound of claim 8, wherein:
$R^4$ is selected from optionally substituted phenyl, C$_1$-C$_6$ alkyl, C$_2$-C$_8$ alkenyl, C$_2$-C$_8$ alkynyl, C$_3$-C$_8$ cycloalkyl, —(C$_1$-C$_6$ alkyl)-(C$_3$-C$_8$ cycloalkyl), and —(C$_1$-C$_6$ alkyl)-Ar$^2$;
$R^5$ is hydrogen;
$R^{6a}$ is C$_1$-C$_6$ alkyl, C$_1$-C$_6$ monohaloalkyl, or C$_1$-C$_6$ polyhaloalkyl;
$R^{6b}$ is hydrogen; and
$R^7$ is C$_1$-C$_6$ alkyl, C$_1$-C$_6$ monohaloalkyl, or C$_1$-C$_6$ polyhaloalkyl.

10. The compound of claim 8, wherein $R^4$ is phenyl.

11. The compound of claim 8, wherein $R^{6a}$ is C$_1$-C$_6$ alkyl and $R^7$ is C$_1$-C$_6$ alkyl.

12. The compound of claim 11, wherein $R^4$ is phenyl, $R^5$ is hydrogen, $R^{6a}$ is CH$_3$, $R^{6b}$ is hydrogen, and $R^7$ is isopropyl.

13. The compound of claim 1, wherein $R^2$ and $R^3$ together comprise the divalent moiety having the structure represented by formula (III):

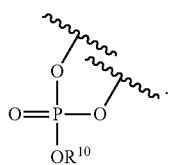

14. The compound of claim 13, wherein $R^{10}$ is C$_1$-C$_6$ alkyl.

15. The compound of claim 1 or a pharmaceutically acceptable salt thereof having a structure selected from the group consisting of:

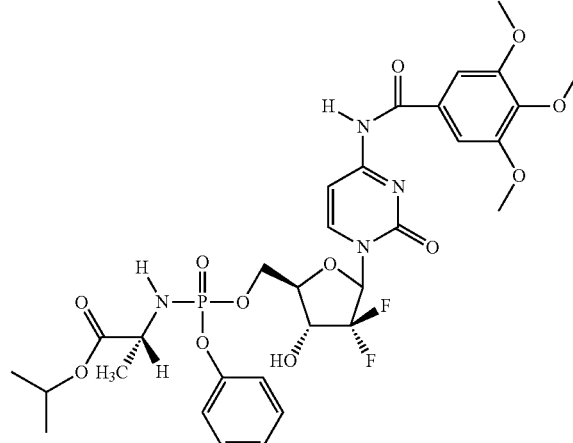

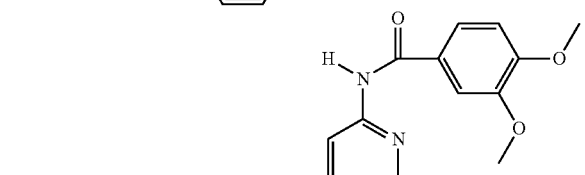

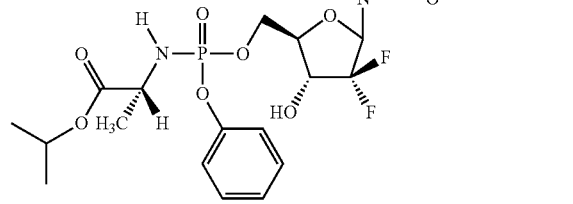

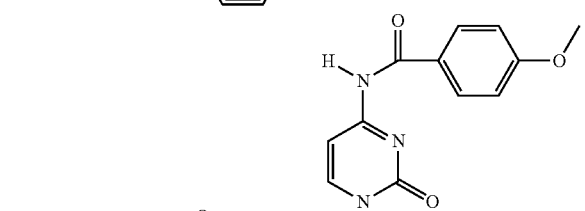

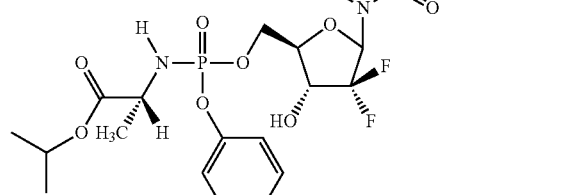

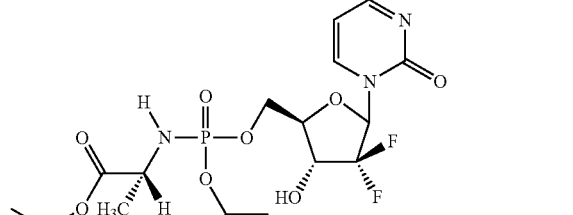

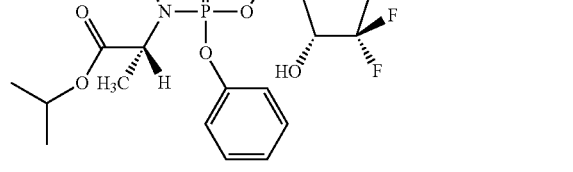

113
-continued
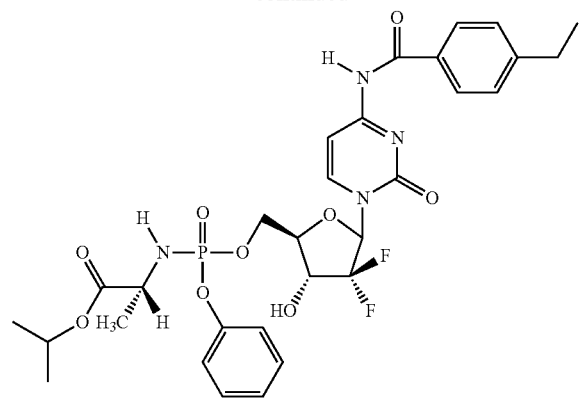
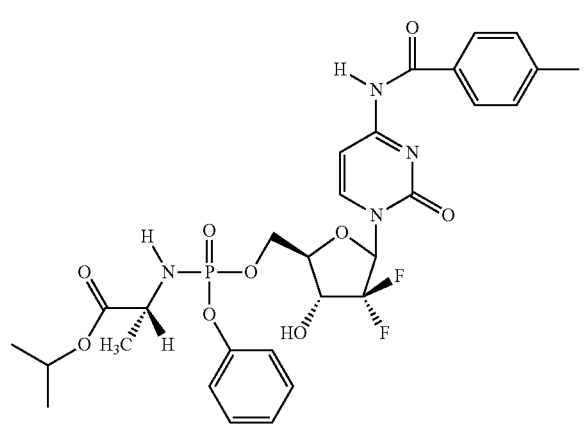
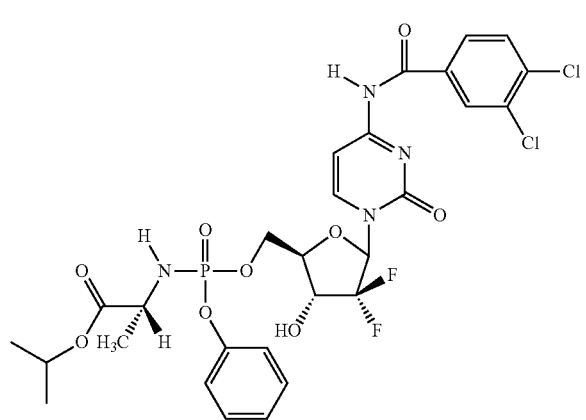
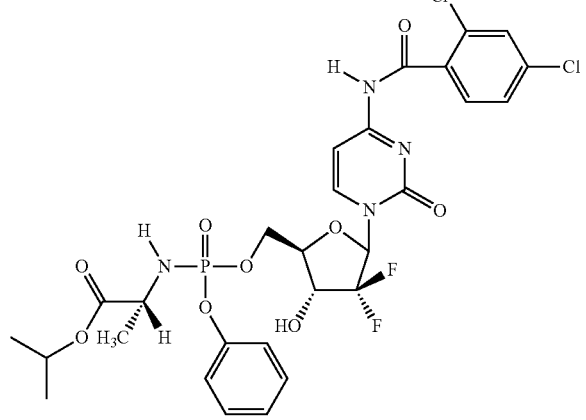
114
-continued
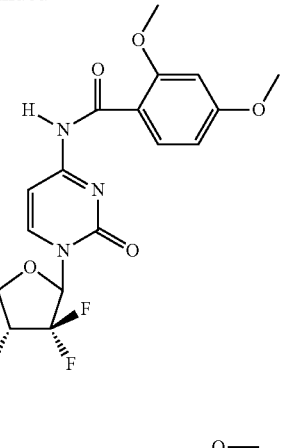
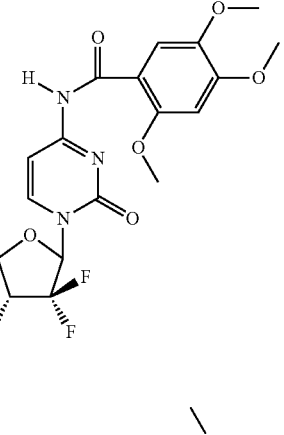
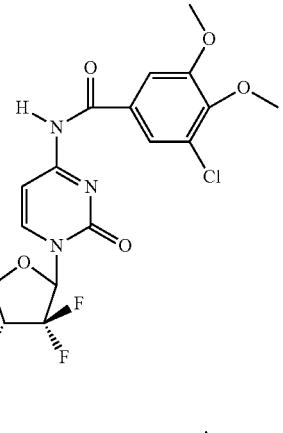
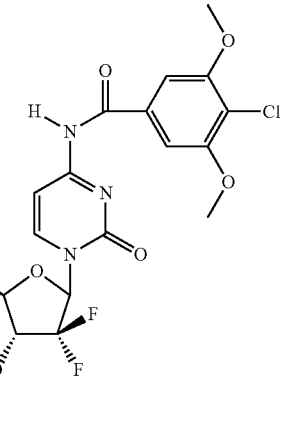

115
-continued
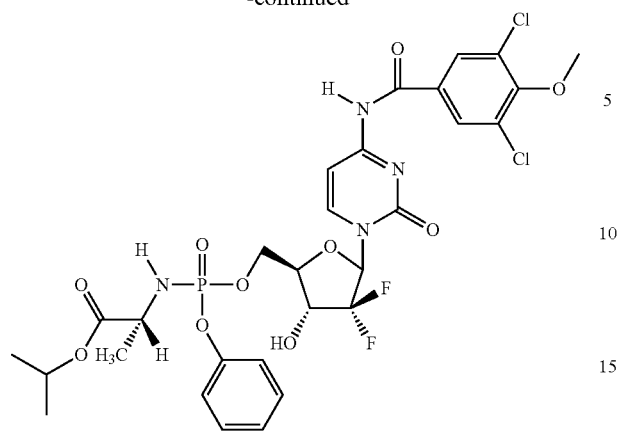
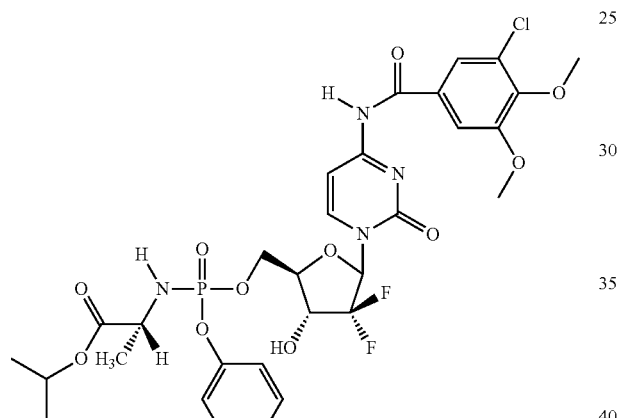
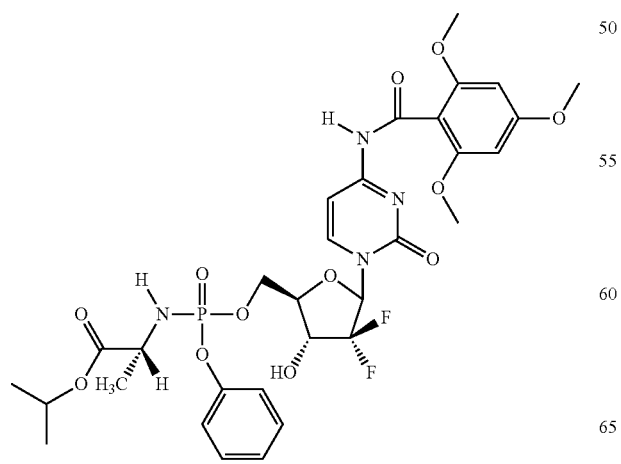
116
-continued
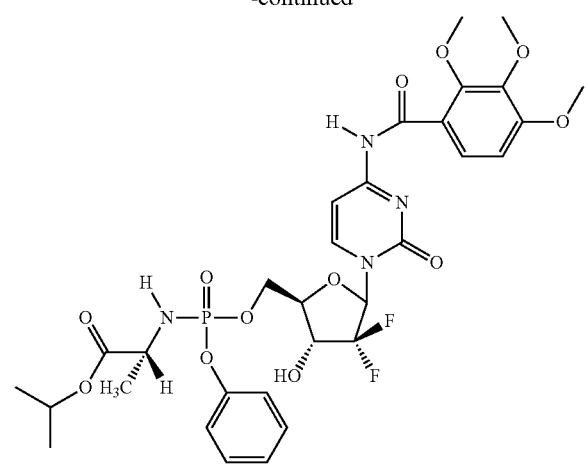
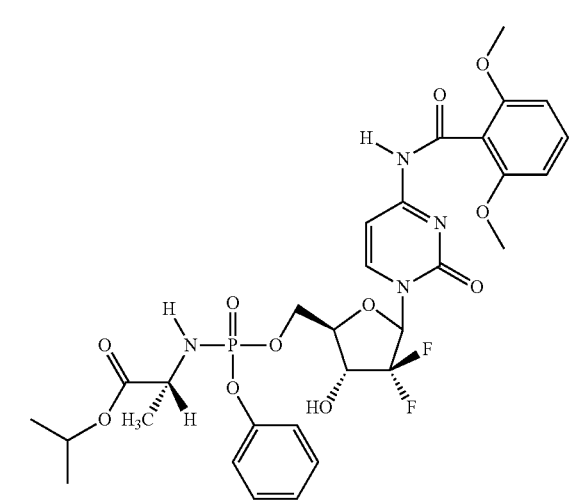
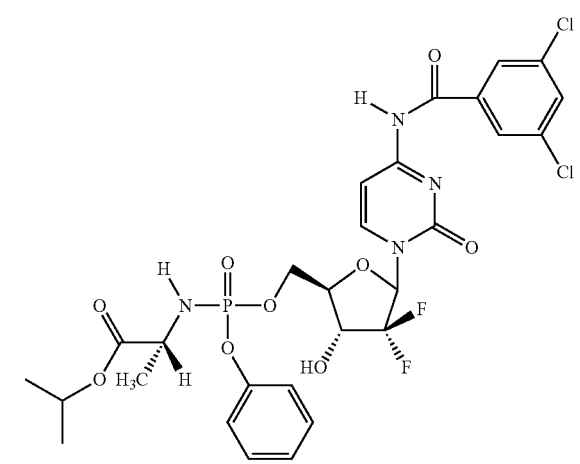

117
-continued
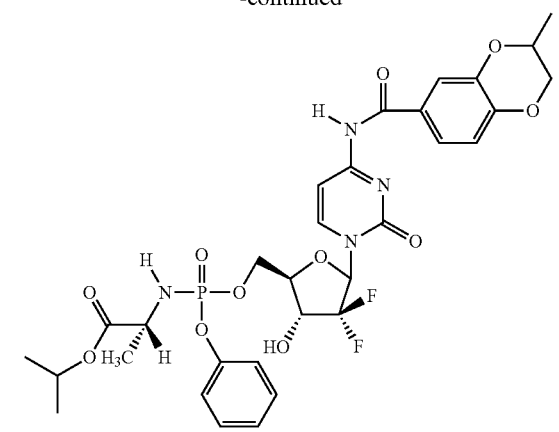
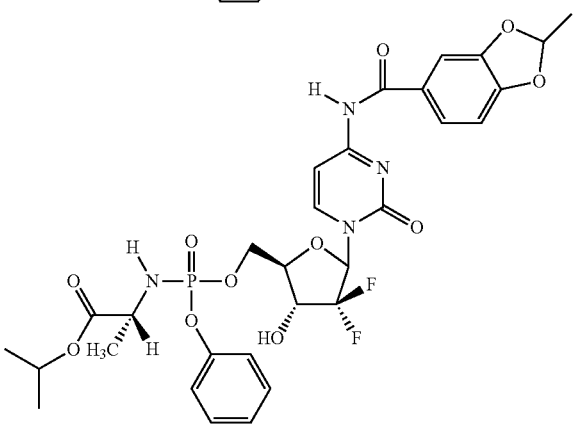
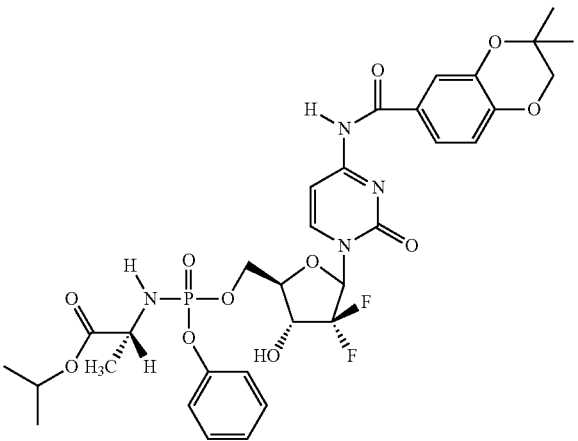
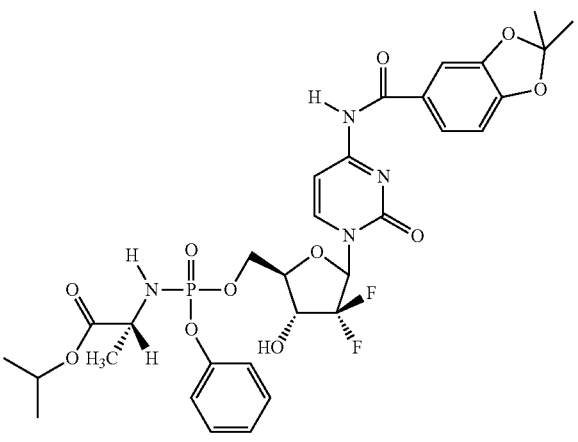
118
-continued
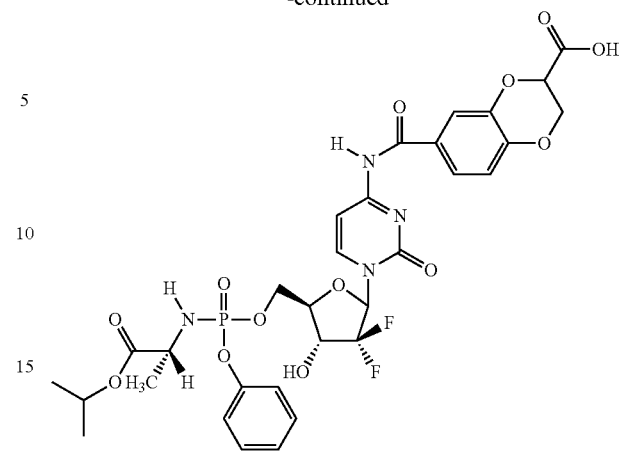
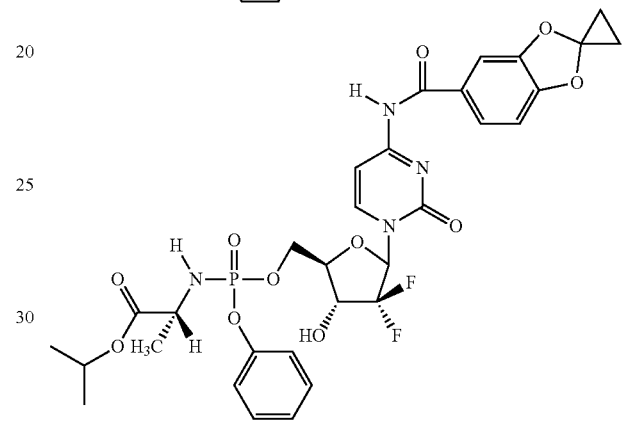
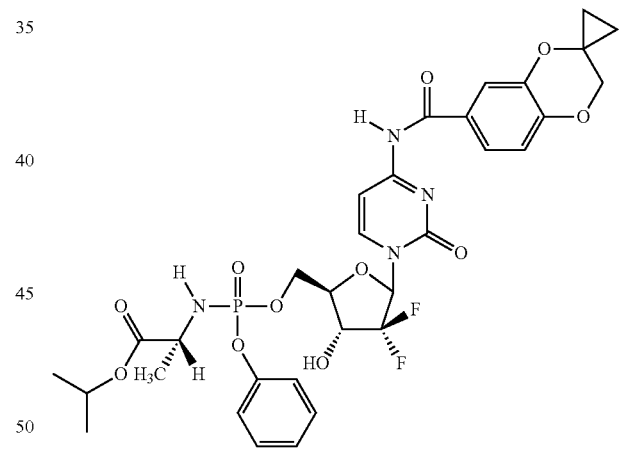
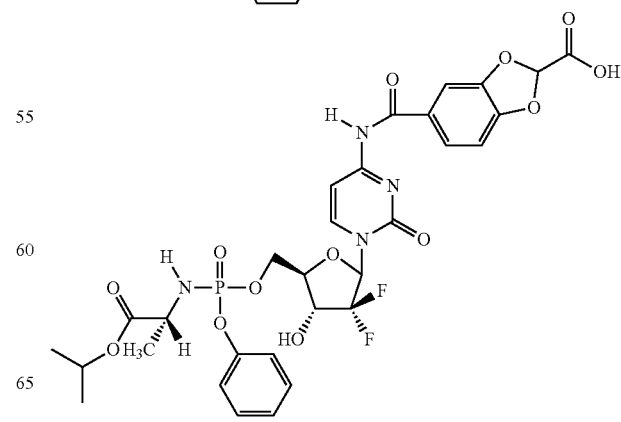

119
-continued
120
-continued
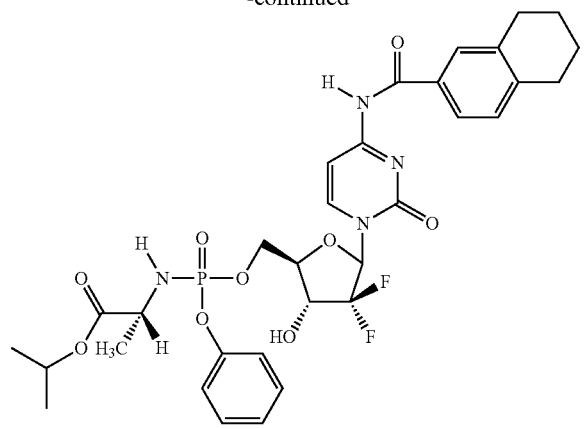
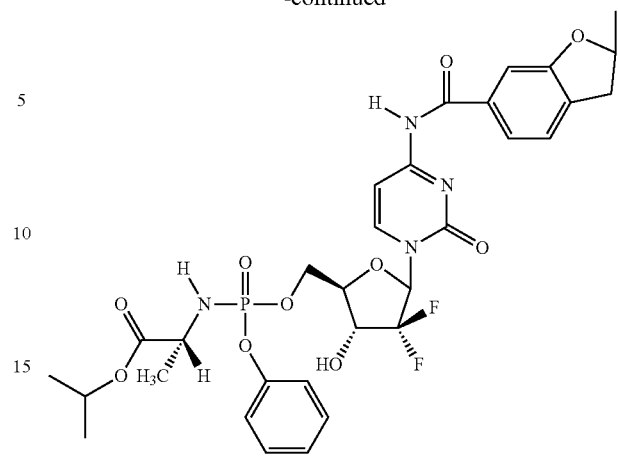

121
-continued
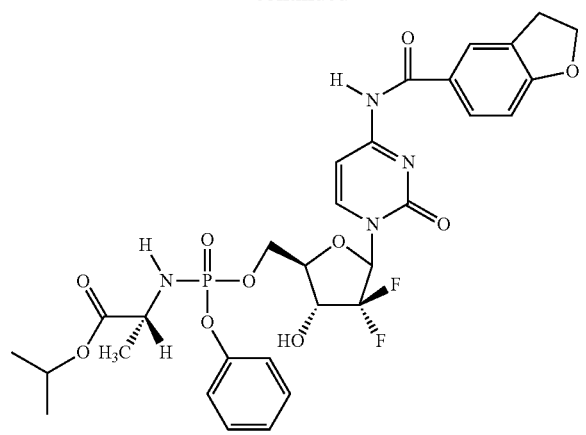
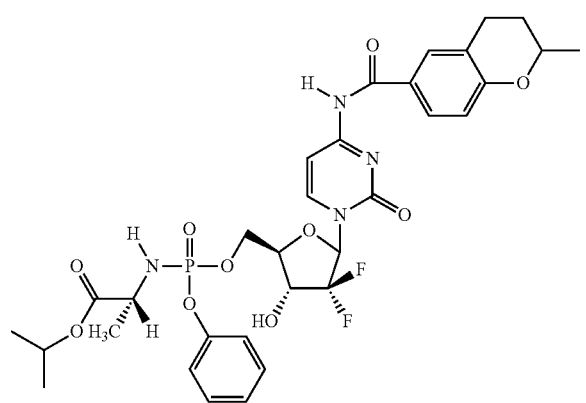
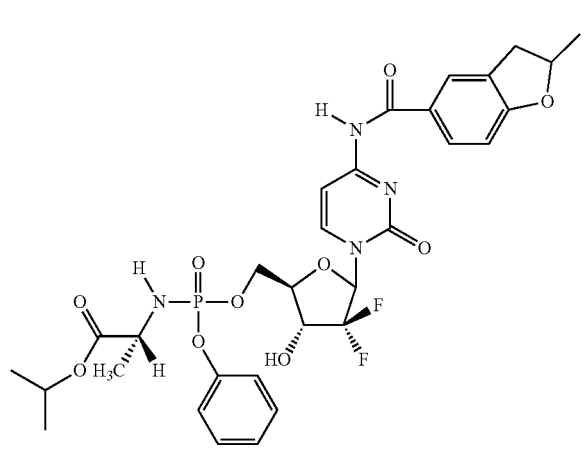
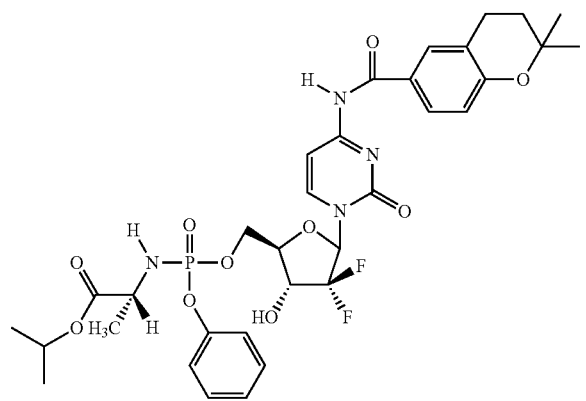
122
-continued
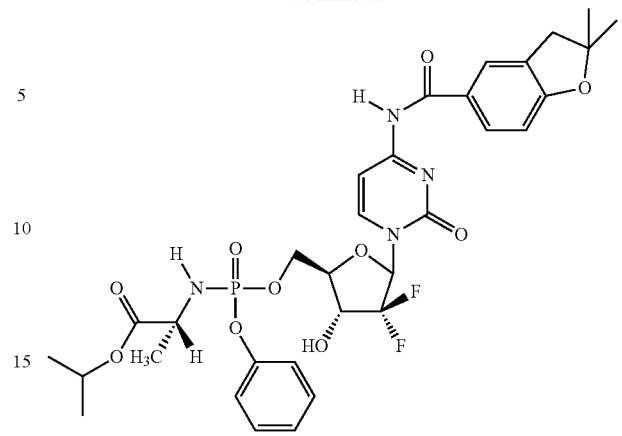
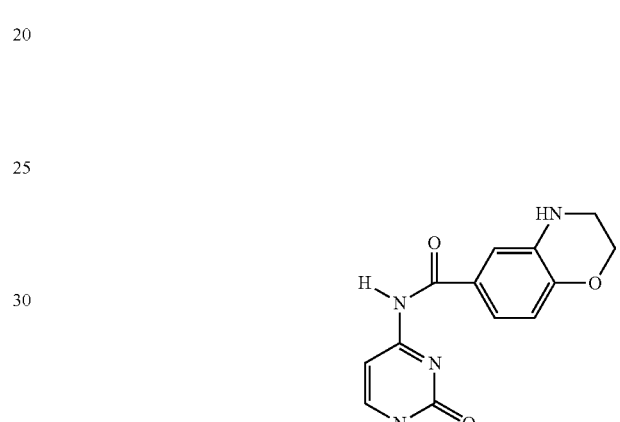
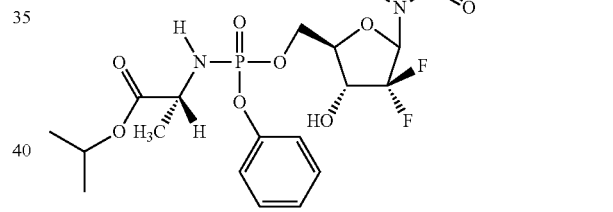
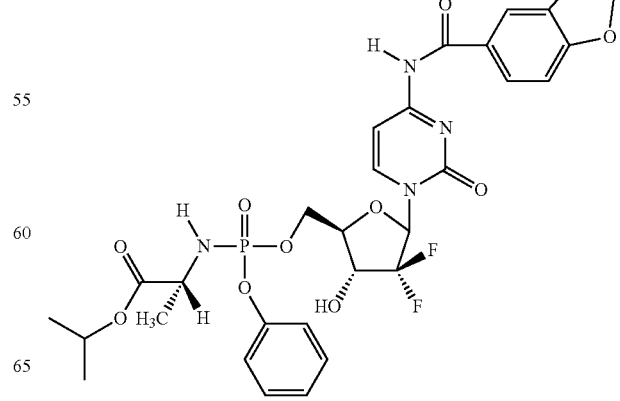

123
-continued
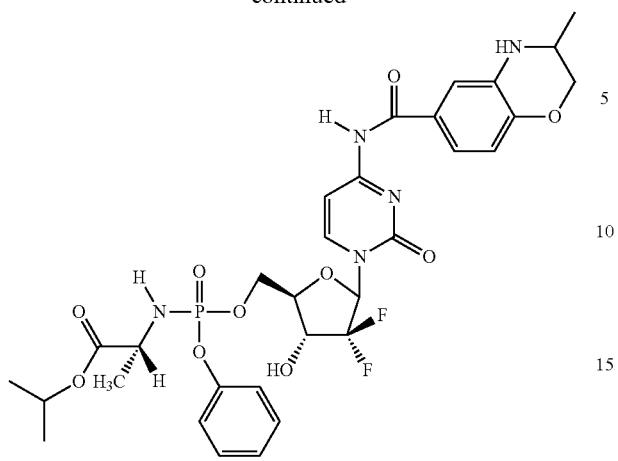
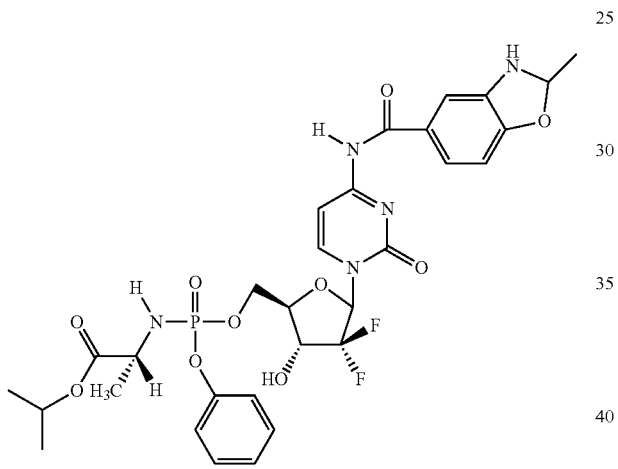
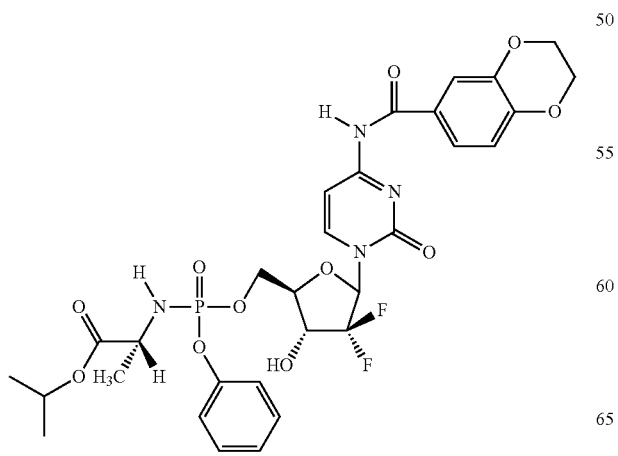
124
-continued
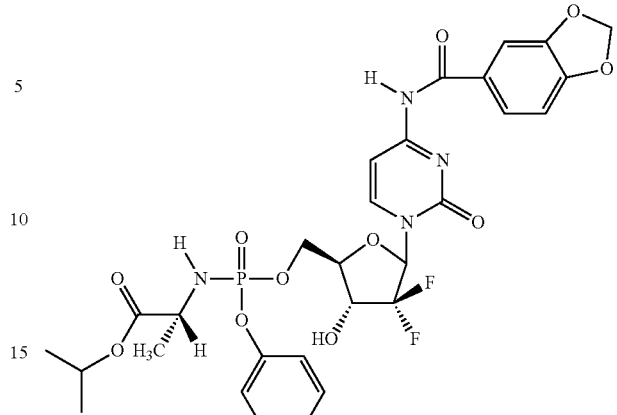
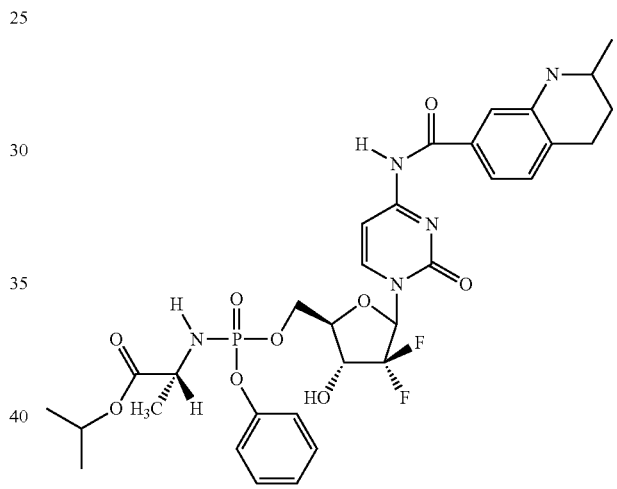
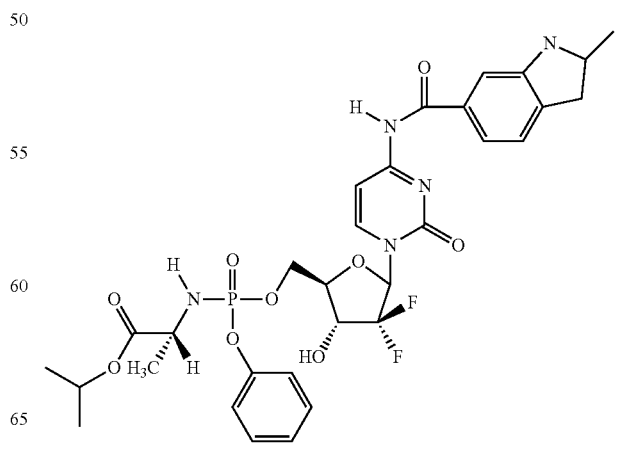

125
-continued
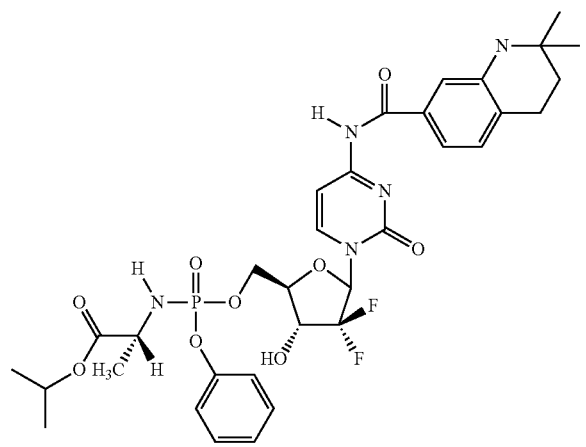
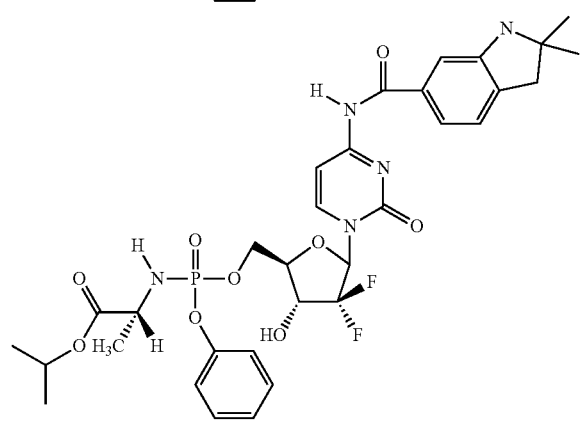
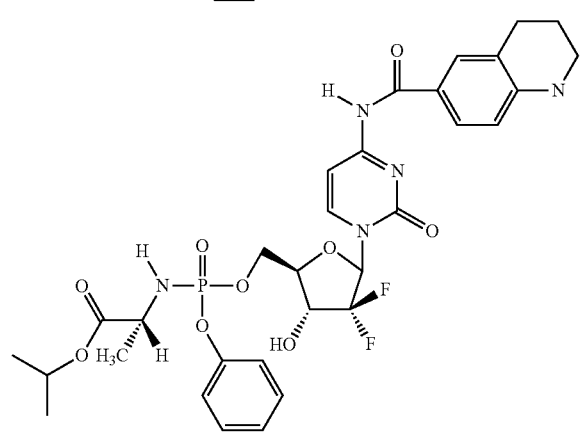
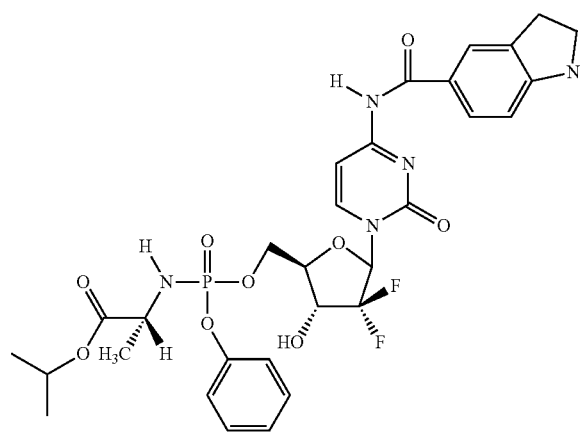
126
-continued
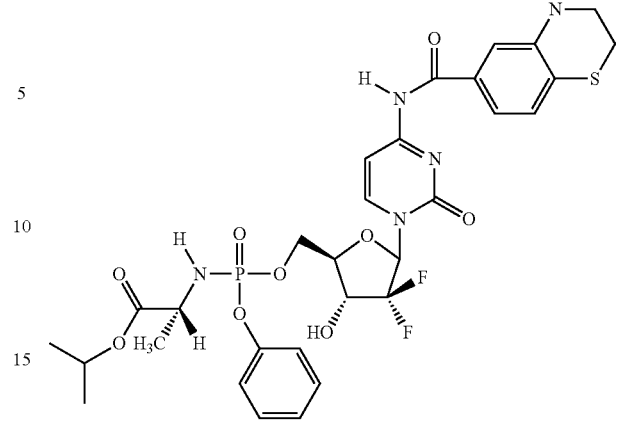
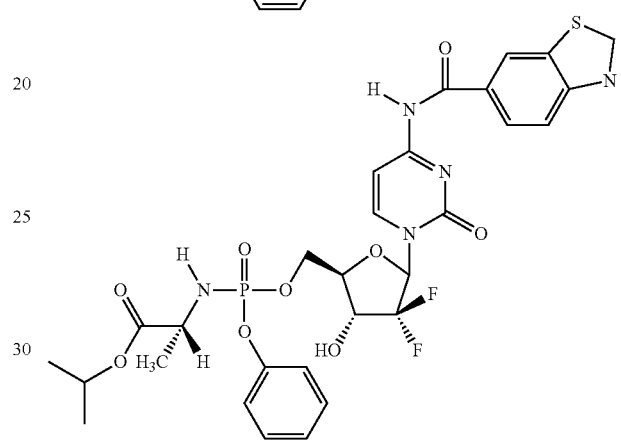
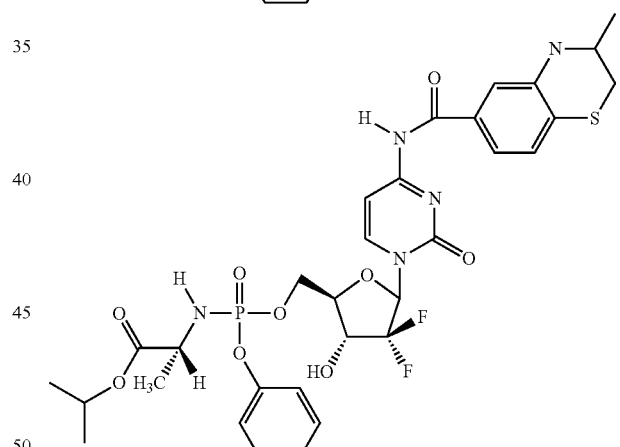
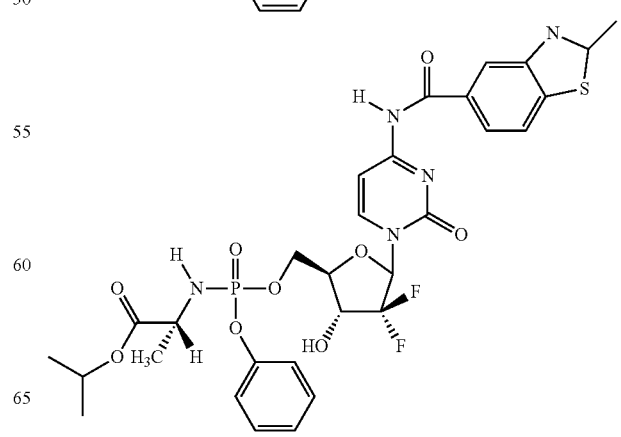

-continued
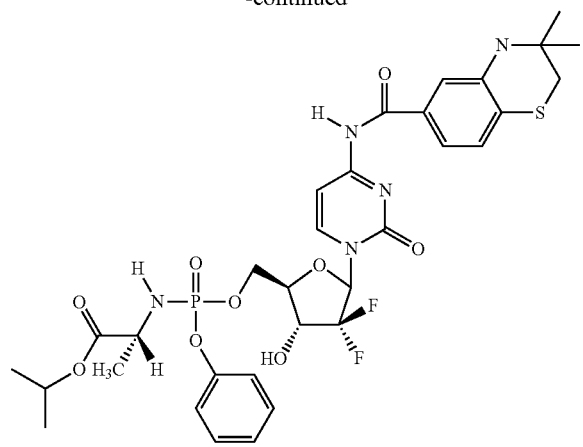
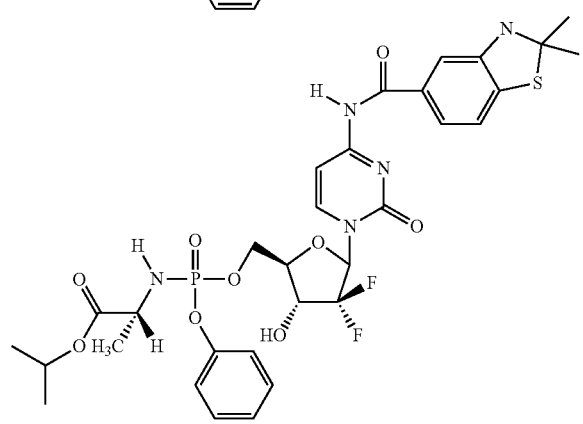
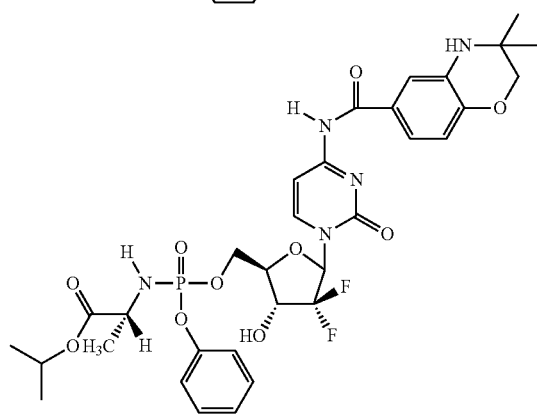
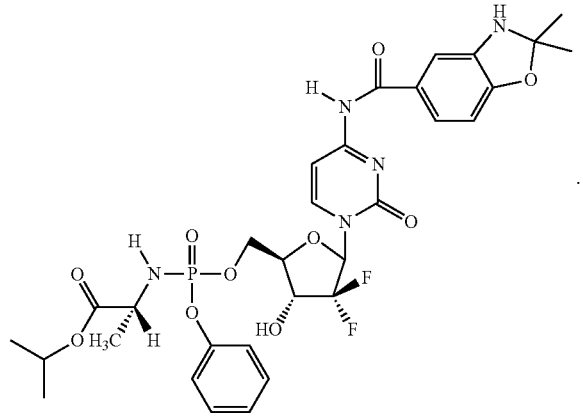
16. The compound of claim 1 or a pharmaceutically acceptable salt thereof having the structure:
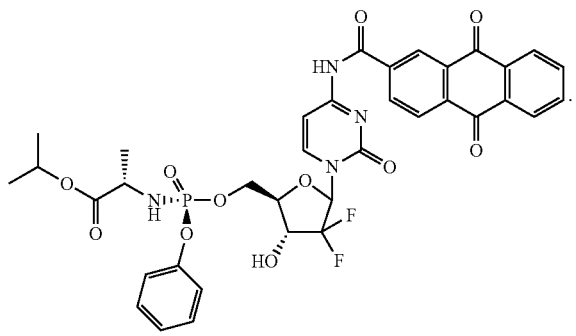 [SMILES: CC(C)OC(=O)[C@H](C)N[P@](=O)(OC[C@H]1OC(n2ccc(NC(=O)c3ccc4c(c3)C(=O)c3ccccc3C4=O)nc2=O)C(F)(F)[C@@H]1O)Oc1ccccc1]
17. The compound of claim 1 or a pharmaceutically acceptable salt thereof having a structure selected from the group consisting:
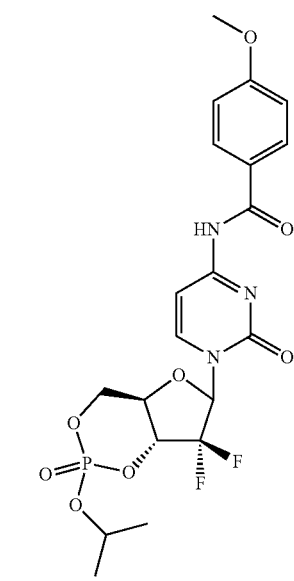
and

129
-continued
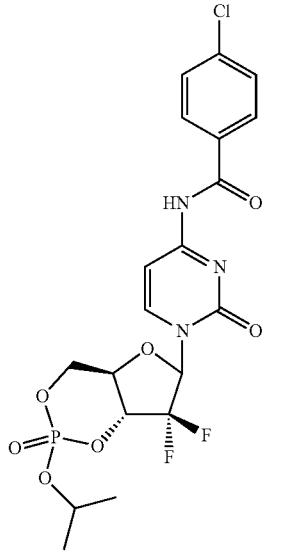
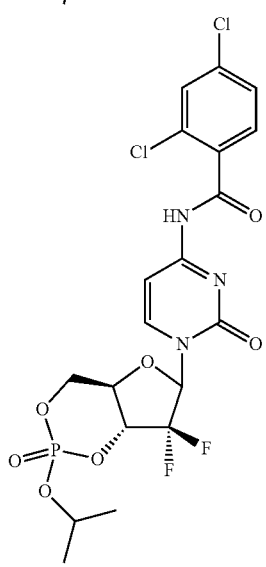
130
-continued
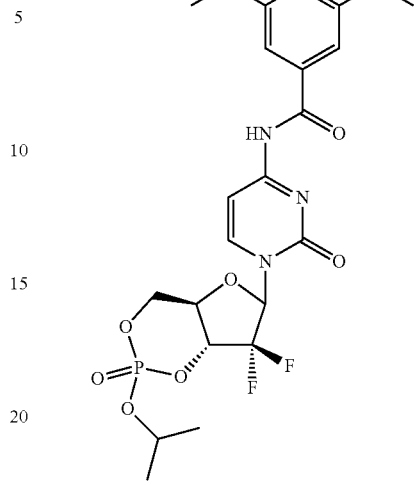
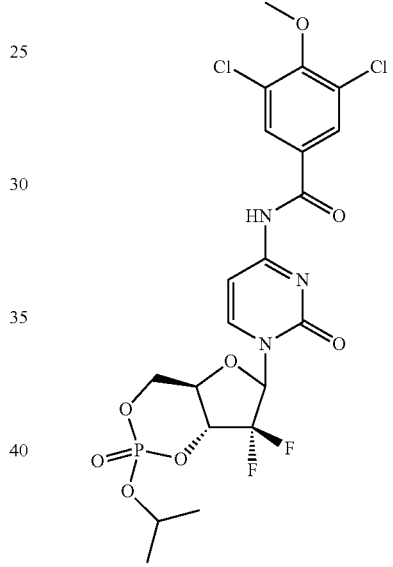
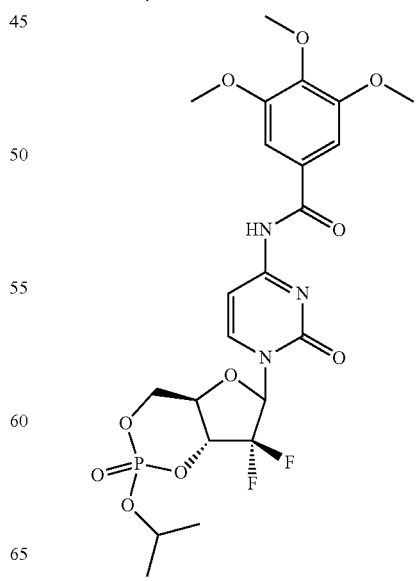

131
-continued
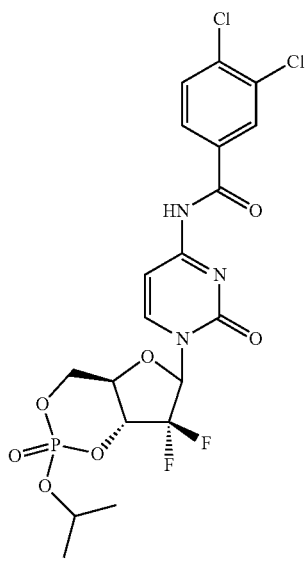
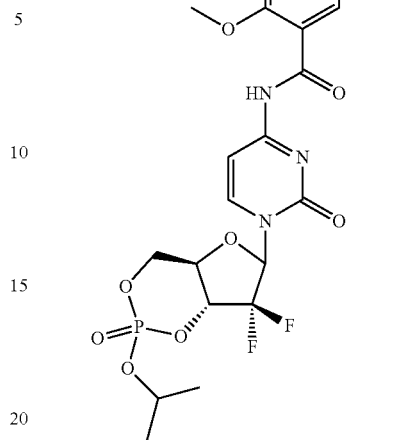
132
-continued
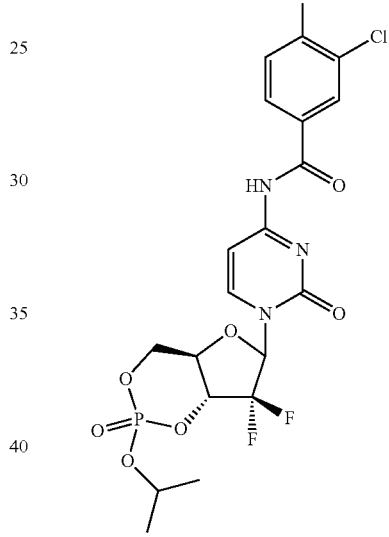
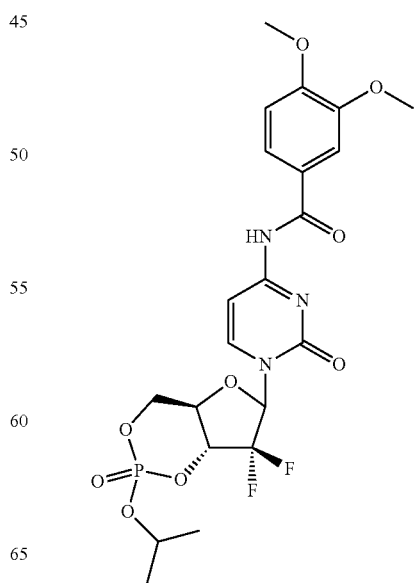

133
-continued
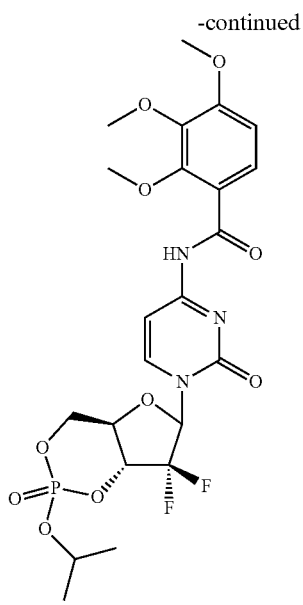
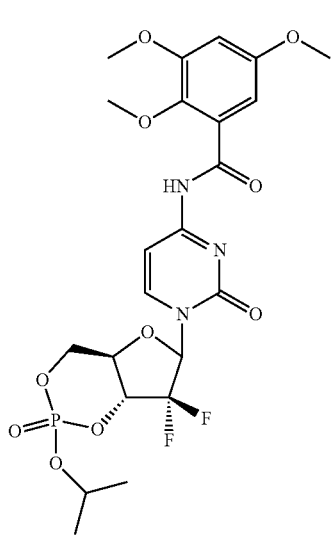
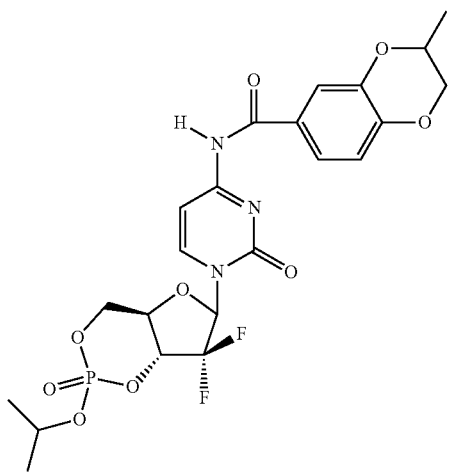
134
-continued
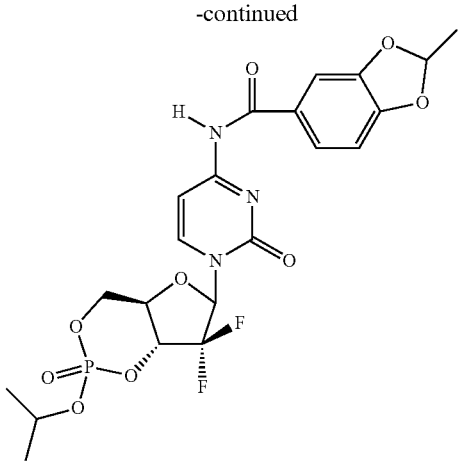
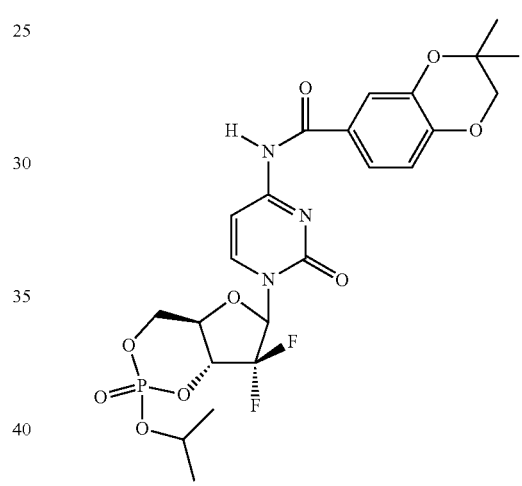
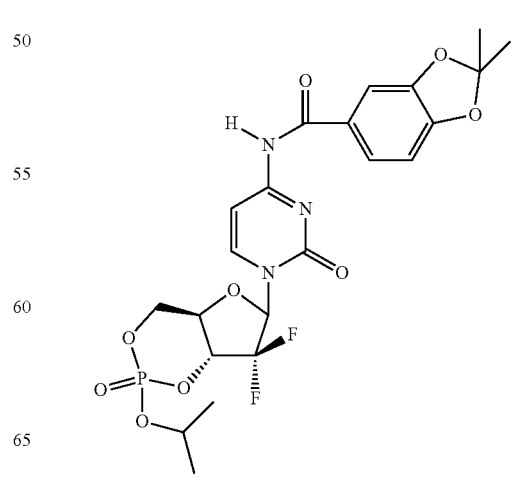

135
-continued
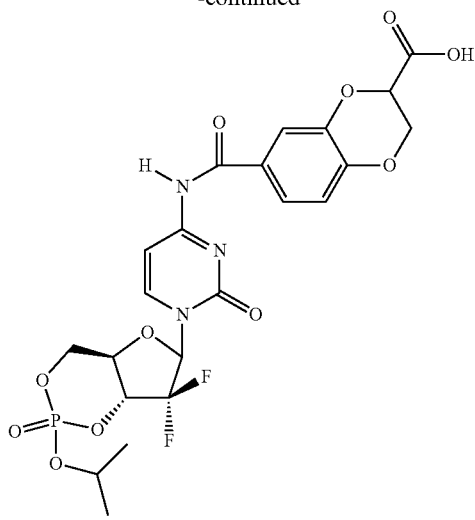
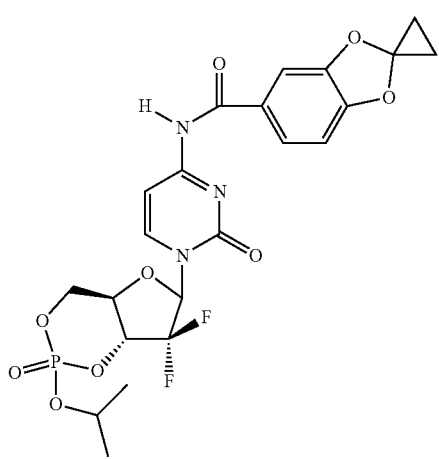
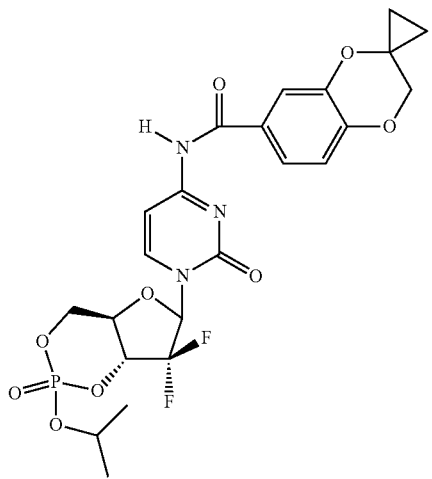
136
-continued
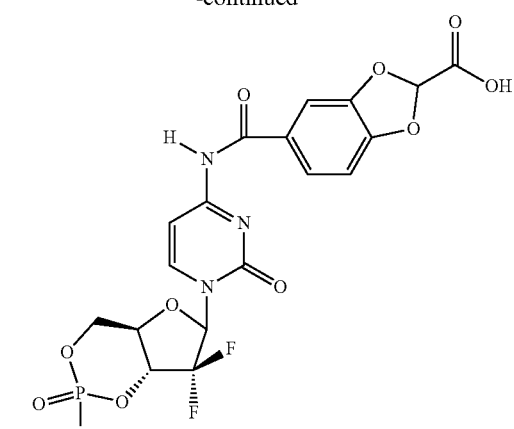
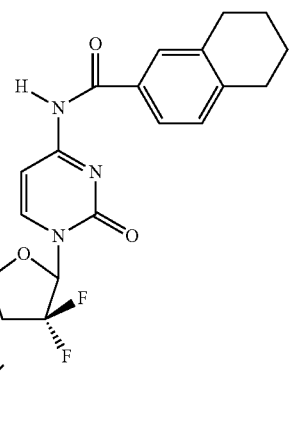
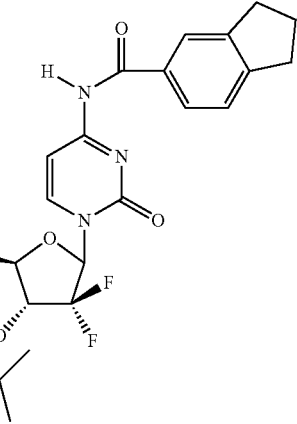

137
-continued
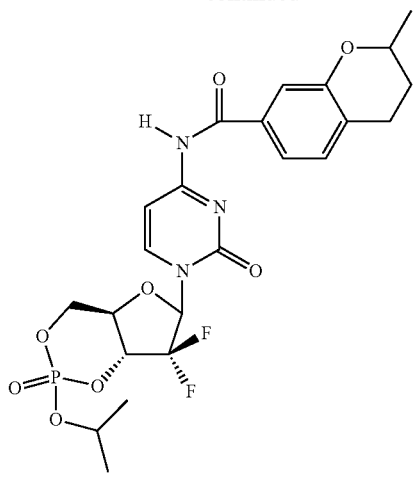
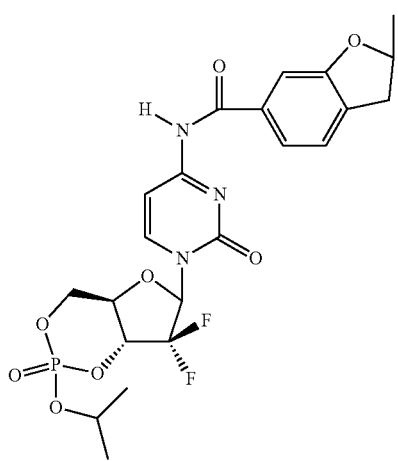
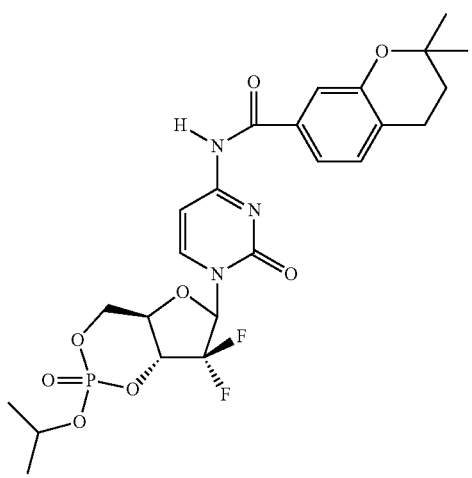
138
-continued
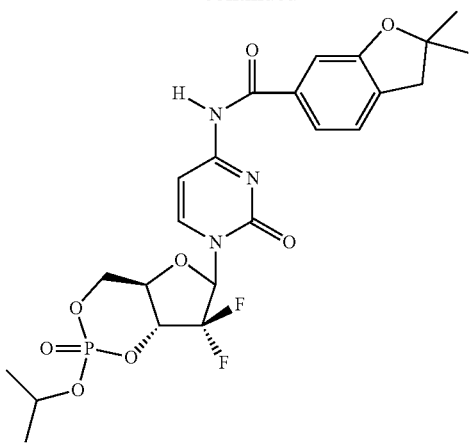
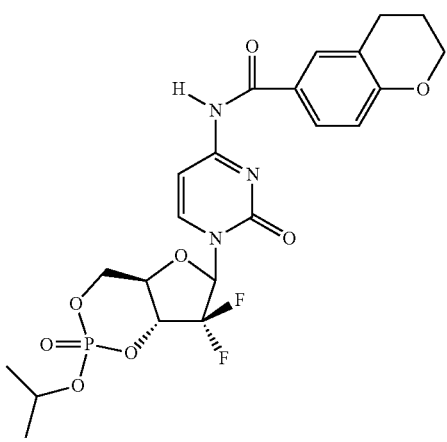
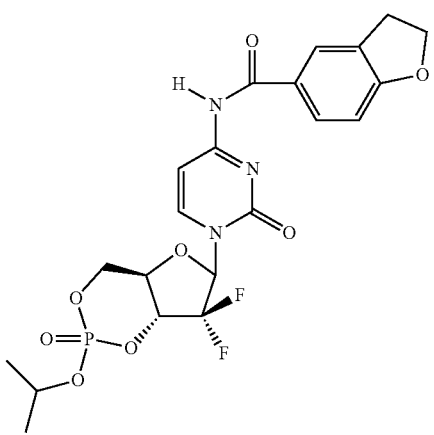

139
-continued
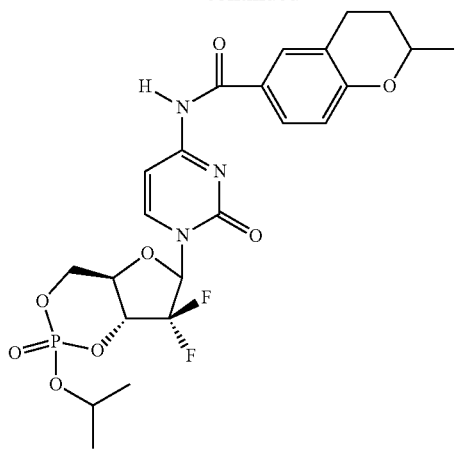
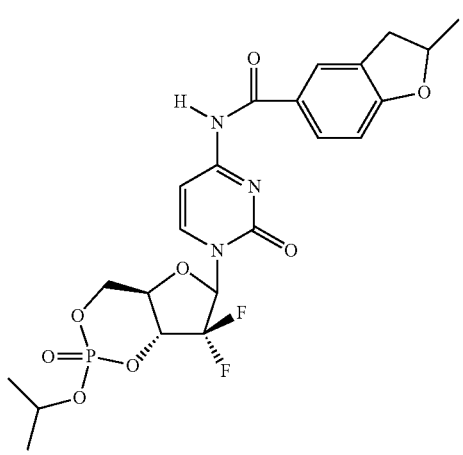
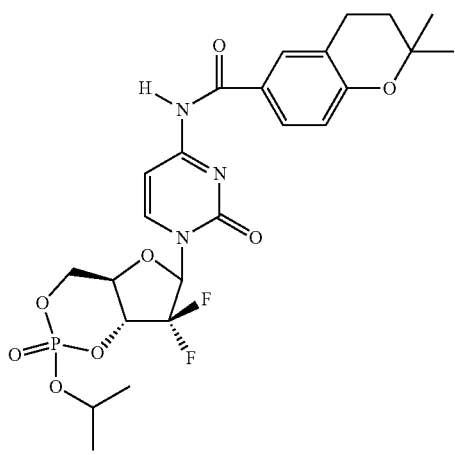
140
-continued
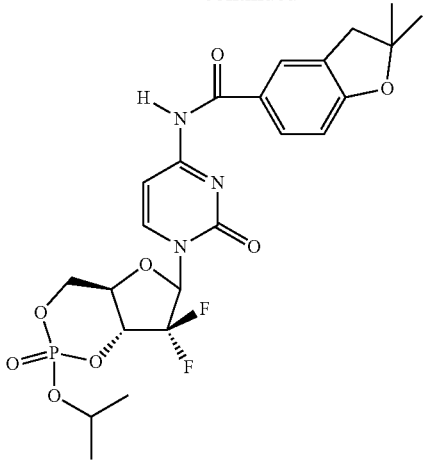
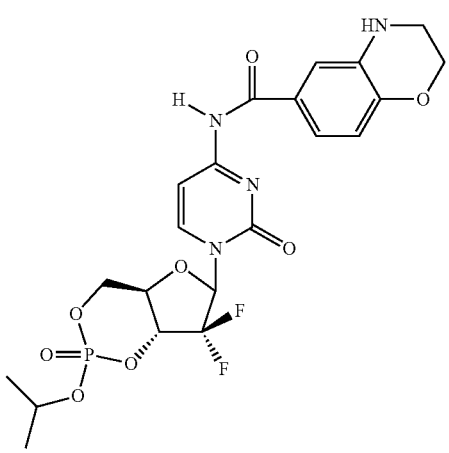
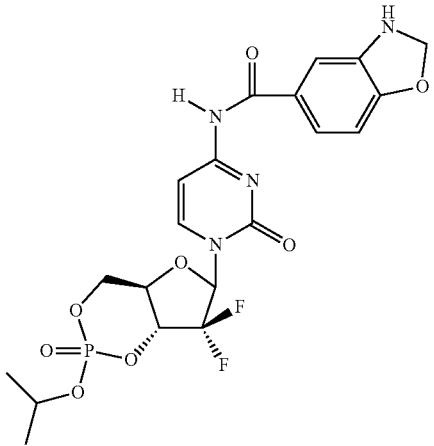

141
-continued
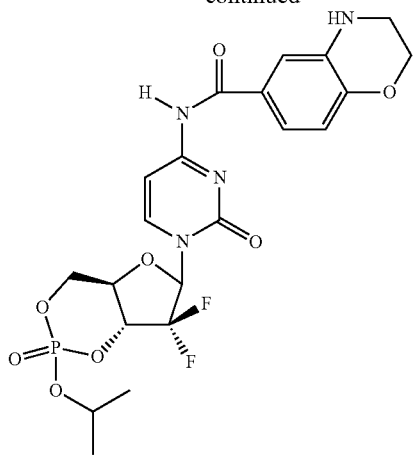
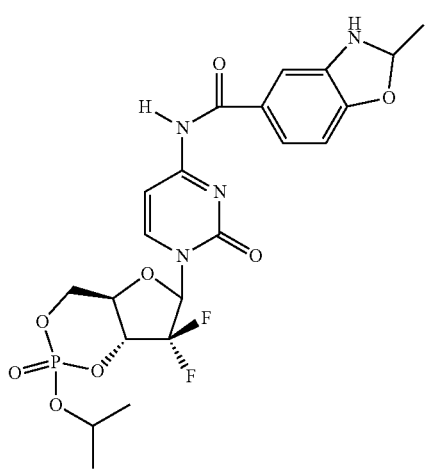
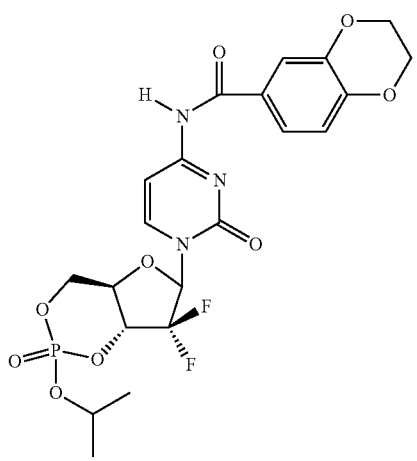
142
-continued
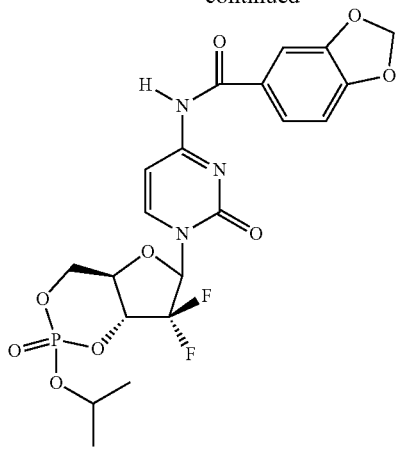
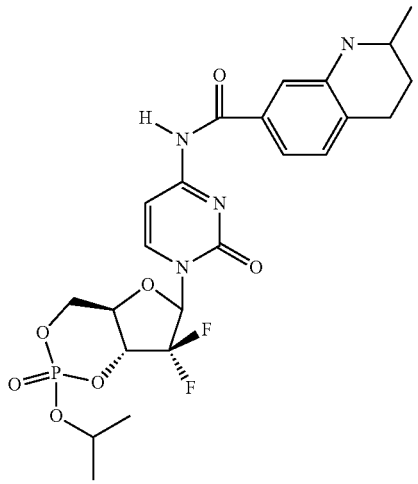
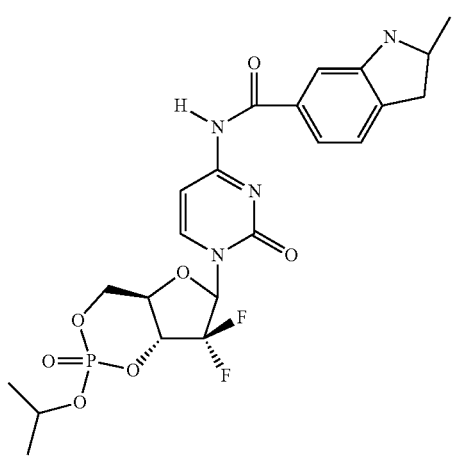

143
-continued
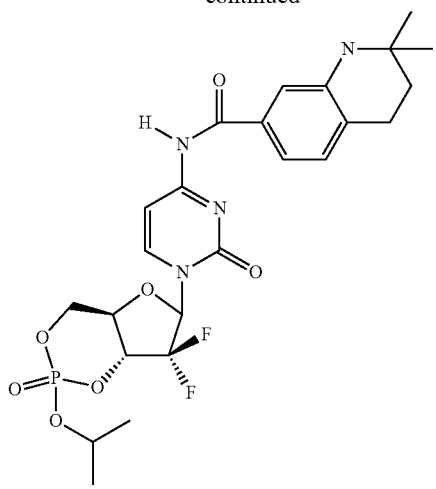
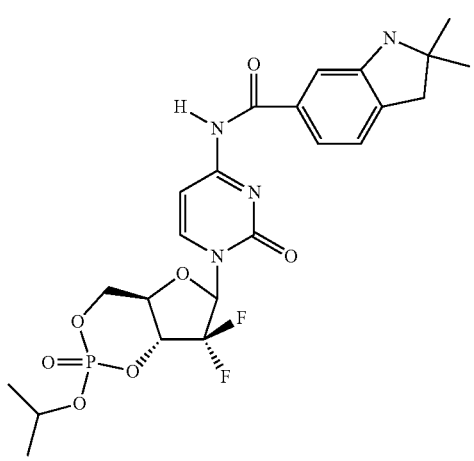
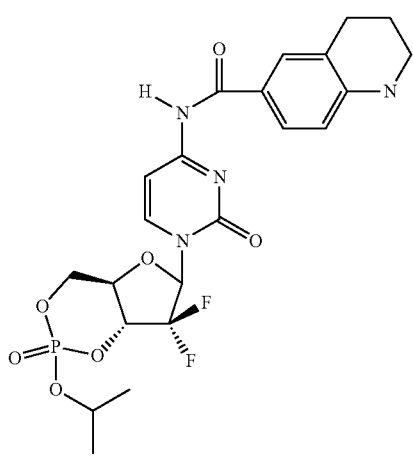
144
-continued
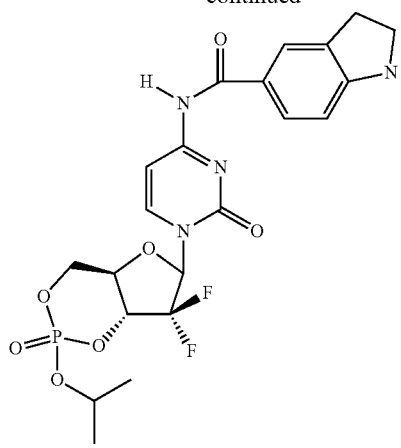
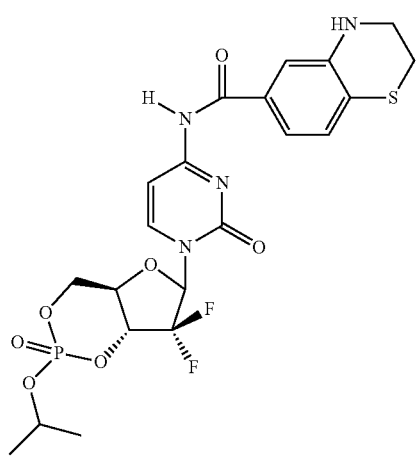
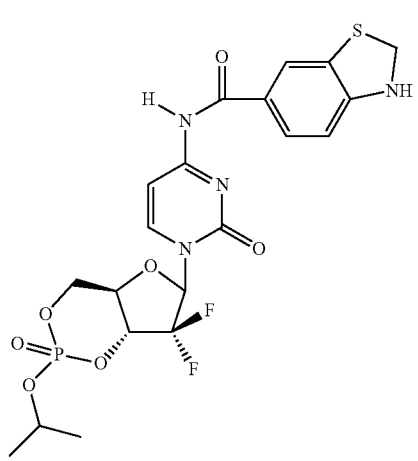

145
-continued
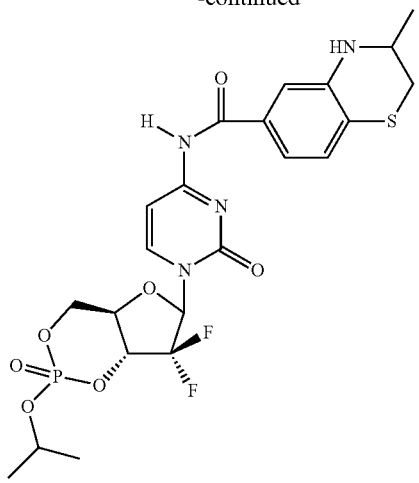
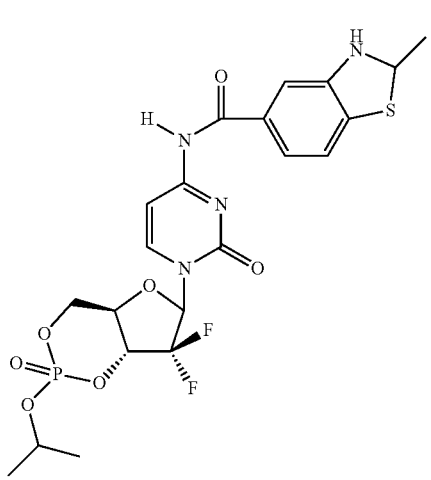
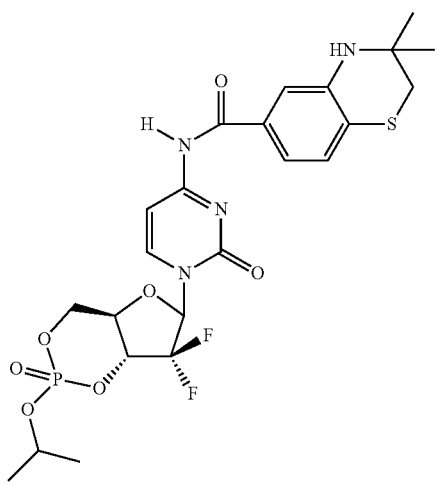
146
-continued
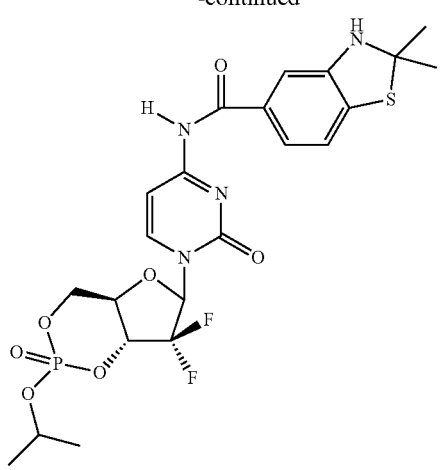
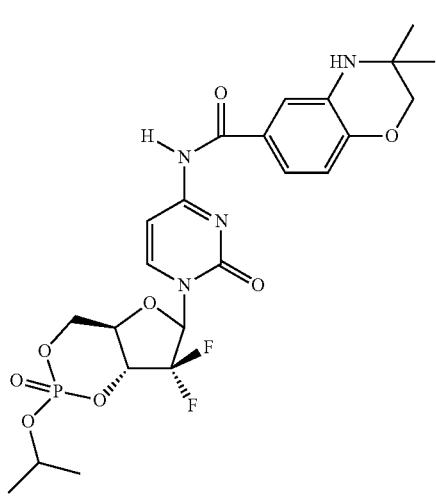
and
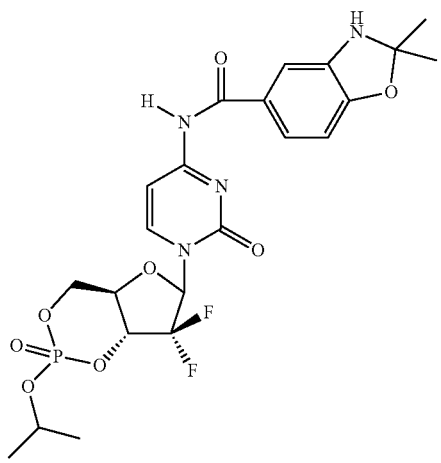

18. A compound of formula (IV):

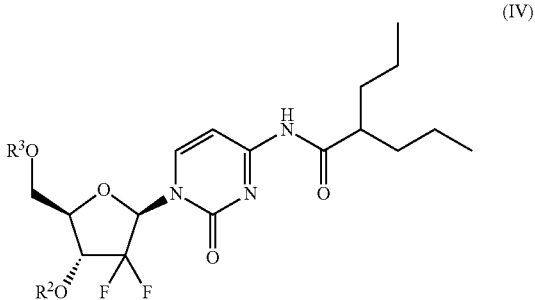

(IV)

or a pharmaceutically acceptable salt, hydrate, solvate, or polymorph thereof, wherein:

$R^2$ is selected from hydrogen and a hydroxyl protecting group;

$R^3$ is a moiety having a structure represented by formula (II):

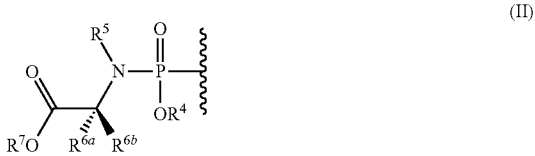

(II)

$R^4$ is selected from $C_1$-$C_6$ alkyl, $C_1$-$C_6$ monohaloalkyl, $C_1$-$C_6$ polyhaloalkyl, $C_2$-$C_8$ alkenyl, $C_2$-$C_8$ alkynyl, $C_3$-$C_8$ cycloalkyl, $C_2$-$C_8$ heterocycloalkyl, $Ar^2$, —($C_1$-$C_6$ alkyl)-($C_3$-$C_8$ cycloalkyl), —($C_1$-$C_6$ alkyl)-($C_2$-$C_8$ heterocycloalkyl), and —($C_1$-$C_6$ alkyl)-$Ar^2$;

$R^5$ is selected from hydrogen, $C_1$-$C_6$ alkyl, $C_1$-$C_6$ monohaloalkyl, $C_1$-$C_6$ polyhaloalkyl, $C_2$-$C_8$ alkenyl, $C_2$-$C_8$ alkynyl, $C_3$-$C_8$ cycloalkyl, $C_2$-$C_8$ heterocycloalkyl, $Ar^2$, —($C_1$-$C_6$ alkyl)-($C_3$-$C_8$ cycloalkyl), —($C_1$-$C_6$ alkyl)-($C_2$-$C_8$ heterocycloalkyl), and ($C_1$-$C_6$ alkyl)-$Ar^2$;

each of $R^{6a}$ and $R^{6b}$ is selected from hydrogen, $C_1$-$C_6$ alkyl, $C_1$-$C_6$ monohaloalkyl, $C_1$-$C_6$ polyhaloalkyl, $C_2$-$C_8$ alkenyl, $C_2$-$C_8$ alkynyl, $C_3$-$C_8$ cycloalkyl, $C_2$-$C_8$ heterocycloalkyl, $Ar^2$, —($C_1$-$C_6$ alkyl)-($C_3$-$C_8$ cycloalkyl), —($C_1$-$C_6$ alkyl)-($C_2$-$C_8$ heterocycloalkyl), and —($C_1$-$C_6$ alkyl)-$Ar^2$, provided that each of $R^{6a}$ and $R^{6b}$ are not the same; and $R^7$ is selected from $C_1$-$C_6$ alkyl, $C_1$-$C_6$ monohaloalkyl, $C_1$-$C_6$ polyhaloalkyl, $C_2$-$C_8$ alkenyl, $C_2$-$C_8$ alkynyl, $C_3$-$C_8$ cycloalkyl, $C_2$-$C_8$ heterocycloalkyl, $Ar^2$, —($C_1$-$C_6$ alkyl)-($C_3$-$C_8$ cycloalkyl), —($C_1$-$C_6$ alkyl)-($C_2$-$C_8$ heterocycloalkyl), and —($C_1$-$C_6$ alkyl)-$Ar^2$;

$Ar^2$ is an optionally substituted phenyl, naphthalene, monocyclic heteroaryl, bicyclic heteroaryl or polycyclic heteroaryl; or $R^2$ and $R^3$ together comprise a divalent moiety having a structure represented by formula (III):

(III)

$R^{10}$ is selected from hydrogen, $C_1$-$C_6$ alkyl, $C_1$-$C_6$ monohaloalkyl, $C_1$-$C_6$ polyhaloalkyl, $C_2$-$C_8$ alkenyl, $C_2$-$C_8$ alkynyl, $C_3$-$C_8$ cycloalkyl, $C_2$-$C_8$ heterocycloalkyl, $Ar^2$, —($C_1$-$C_6$ alkyl)-($C_3$-$C_8$ cycloalkyl), —($C_1$-$C_6$ alkyl)-($C_2$-$C_8$ heterocycloalkyl), —($C_1$-$C_6$ alkyl)-$Ar^2$.

19. The compound of claim 18, wherein $R^2$ is selected from hydrogen and a hydroxyl protecting group and $R^3$ is a moiety having a structure represented by formula (II):

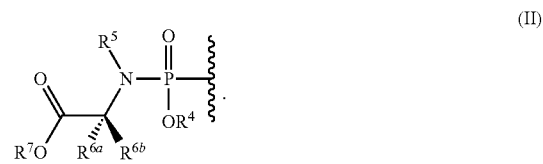

(II)

20. The compound of claim 19, wherein:

$R^4$ is selected from optionally substituted phenyl, $C_1$-$C_6$ alkyl, $C_2$-$C_8$ alkenyl, $C_2$-$C_8$ alkynyl, $C_3$-$C_8$ cycloalkyl, —($C_1$-$C_6$ alkyl)-($C_3$-$C_8$ cycloalkyl), and —($C_1$-$C_6$ alkyl)-$Ar^2$;

$R^5$ is hydrogen;

$R^{6a}$ is $C_1$-$C_6$ alkyl, $C_1$-$C_6$ monohaloalkyl, or $C_1$-$C_6$ polyhaloalkyl;

$R^{6b}$ is hydrogen, and $R^7$ is $C_1$-$C_6$ alkyl, $C_1$-$C_6$ monohaloalkyl, or $C_1$-$C_6$ polyhaloalkyl.

21. The compound of claim 19, wherein $R^4$ is phenyl.

22. The compound of claim 19, wherein $R^{6a}$ is $C_1$-$C_6$ alkyl and $R^7$ is $C_1$-$C_6$ alkyl.

23. The compound of claim 22, wherein $R^4$ is phenyl, $R^5$ is hydrogen, $R^{6a}$ is $CH_3$, $R^{6b}$ is hydrogen, and $R^7$ is isopropyl.

24. A compound of formula (V):

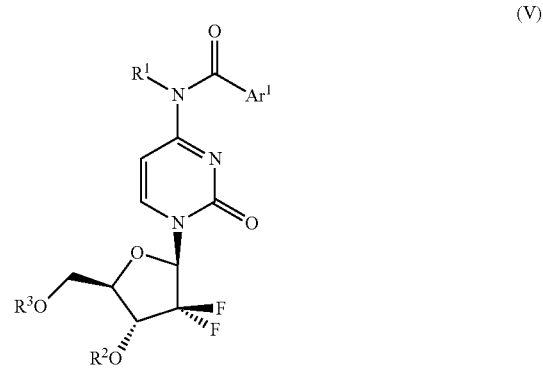

(V)

or a pharmaceutically acceptable salt, hydrate, solvate, or polymorph thereof, wherein:

$Ar^a$ is naphthyl or is a bicyclic or polycyclic fused ring system comprising an aryl ring fused to one or more 4-, 5-, 6-, 7-, or 8-membered cycloalkyl or fused to a 4-, 5-, 6-, 7-, or 8-membered cycloalkyl or heterocycloalkyl which is fused to a second aryl ring, wherein the aryl rings of the bicyclic or polycyclic fused ring system are each independently selected from phenyl, pyridinyl, pyrimidinyl, pyridazinyl, pyrazinyl, and triazinyl;

wherein the naphthyl or the aryl rings of the bicyclic or polycyclic fused ring system are each optionally substituted with 1, 2, or 3 groups independently selected from halogen, —OH, —CN, —NH$_2$, thiol, C$_1$-C$_6$ alkyl, C$_1$-C$_6$ alkoxy, C$_1$-C$_6$ monohaloalkyl, C$_1$-C$_6$ polyhaloalkyl, C$_1$-C$_6$ alkylamino, and C$_1$-C$_6$ dialkylamino;

wherein the cycloalkyl of the bicyclic or polycyclic fused ring system is optionally substituted with 1, 2, 3, 4, or 5 groups independently selected from halogen, —OH, —CN, —NH$_2$, thiol, oxo, C$_1$-C$_6$ alkyl, C$_1$-C$_6$ alkoxy, C$_1$-C$_6$ monohaloalkyl, C$_1$-C$_6$ polyhaloalkyl, C$_1$-C$_6$ alkylamino, C$_1$-C$_6$ dialkylamino, C$_1$-C$_6$ aminoalkyl, C$_1$-C$_6$ hydroxyalkyl, —(C=O)OR$^8$, and —(C=O)NR$^{9a}$R$^{9b}$, in which each R$^8$ is independently selected from hydrogen, C$_1$-C$_6$ alkyl, and a hydroxyl protecting group, and each of R$^{9a}$ and R$^{9b}$ is independently selected from hydrogen, C$_1$-C$_4$ alkyl, and an amine protecting group;

R$^{13}$ is selected from hydrogen, C$_1$-C$_4$ alkyl, and an amine protecting group;

R$^{14}$ is selected from hydrogen, C$_1$-C$_6$ alkyl and a hydroxyl protecting group; and R$^{15}$ is selected from hydrogen and a hydroxyl protecting group.

25. The compound of claim 24, wherein Ar$^3$ is naphthyl or is a bicyclic or polycyclic fused ring system comprising an aryl ring fused to one or more 4-, 5-, 6-, 7-, or 8-membered cycloalkyl.

26. The compound of claim 24, wherein Ar$^3$ is napthyl optionally substituted with 1, 2, or 3 groups independently selected from halogen, —OH, —CN, —NH$_2$, thiol, C$_1$-C$_6$ alkyl, C$_1$-C$_6$ alkoxy, C$_1$-C$_6$ monohaloalkyl, C$_1$-C$_6$ polyhaloalkyl, C$_1$-C$_6$ alkylamino, and C$_1$-C$_6$ dialkylamino.

27. The compound of 72, wherein the naphthyl or the aryl ring of the bicyclic or polycyclic fused ring system is substituted with 1, 2, or 3 groups selected from chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, and butoxy.

28. The compound of 72, wherein R$^{14}$ and R$^{15}$ are each hydrogen.

29. The compound of claim 24 having a structure selected from the group consisting of:

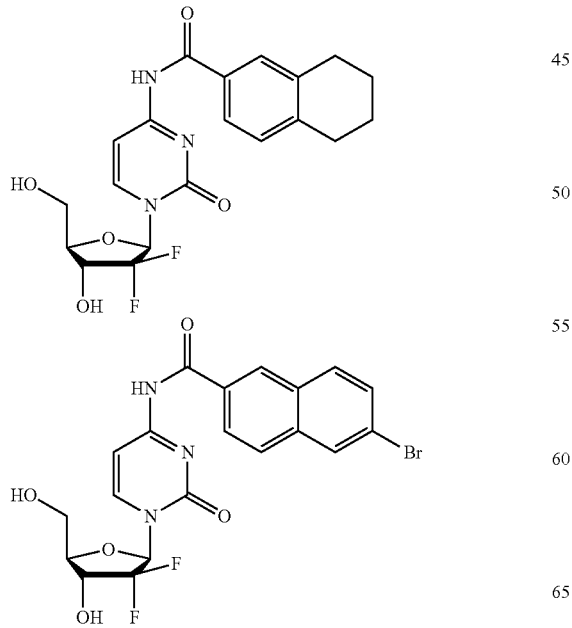

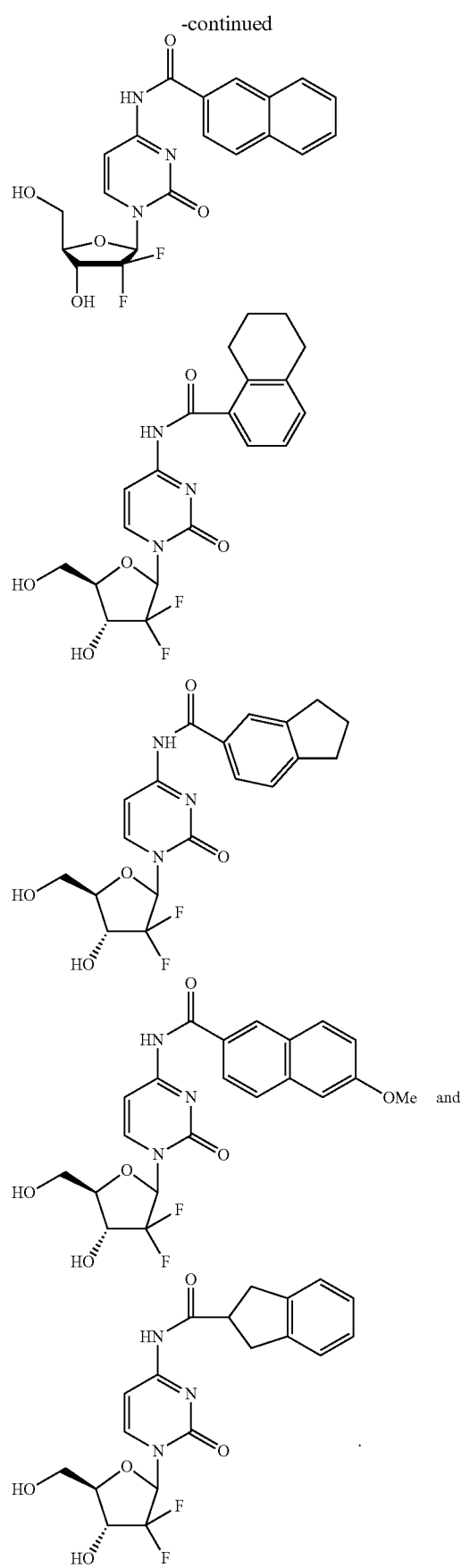

30. The compound of claim 24 having the structure:

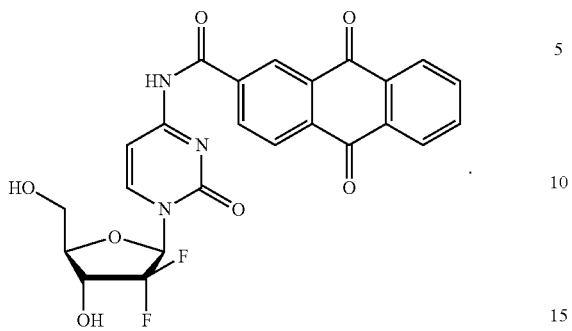

31. A pharmaceutical composition comprising the compound of claim 1 and a pharmaceutically acceptable carrier.

32. A method for treating a disorder in a subject selected from a viral infection and a cancer, the method comprising administering to a subject in need thereof an effective amount of the compound of claim 1.

33. The method of claim 32, wherein the viral infection is selected form the group consisting of dengue virus, Human immunodeficiency virus, Hepatitis A, Hepatitis B, Hepatitis C, Herpes simplex, Cytomegalovirus, Epstein-Barr virus, and Yellow fever.

34. The method of claim 32, wherein the cancer is selected from the group consisting of non-small cell lung cancer, pancreatic cancer, bladder cancer, breast cancer, esophageal cancer and lymphoma.

* * * * *

UNITED STATES PATENT AND TRADEMARK OFFICE
CERTIFICATE OF CORRECTION

| | |
|---|---|
| PATENT NO. | : 10,059,733 B2 |
| APPLICATION NO. | : 15/122506 |
| DATED | : August 28, 2018 |
| INVENTOR(S) | : Zucai Suo |

It is certified that error appears in the above-identified patent and that said Letters Patent is hereby corrected as shown below:

In the Specification

In Column 10 at Line 52-53, Change "antiarrythmics)," to --antiarrhythmics),--.

In Column 12 at Line 53, Change "sbutyl," to --s-butyl,--.

In Column 13 at Line 59, Change "—$OA^1$ $(OA^2)_a$—$OA^3$," to -- —$OA^1$—$(OA^2)_a$—$OA^3$,--.

In Column 15 at Line 10 (Approx.), Change "—$A^1O(O)C$-$A^2$-$OC(O))_a$," to -- —$(A^1O(O)C$-$A^2$-$OC(O))_a$—,--.

In Column 16 at Line 50, Change "2Hchromenyl," to --2H-chromenyl,--.

In Column 23 at Line 19 (Approx.), Change "—(C=O) OR," to -- —(C=O)$OR^8$,--.

In Column 26 at Line 29, Change "hexyl" to --hexyl.--.

In Column 72 at Line 46, Change "syringability." to --syringeability.--.

In Column 76 at Line 34, Change "Phosphorolated" to --Phosphorylated--.

In Column 77 at Line 41, Change "$[M+H]^+659.3$." to --$[M+H]^+$ 659.3,--.

In Column 78 at Line 3, Change "727.2." to --727.2,--.

In Column 78 at Line 30 (Approx.), Change "681.2." to --681.2,--.

In Column 78 at Line 51 (Approx.), Change "699.2." to --699.2,--.

In Column 80 at Line 6 (Approx.), Change "494.2." to --494.2,--.

Signed and Sealed this
Eleventh Day of December, 2018

Andrei Iancu
*Director of the United States Patent and Trademark Office*

CERTIFICATE OF CORRECTION (continued)
U.S. Pat. No. 10,059,733 B2

In Column 81 at Line 60-61, Change "tetraisopropyldisloxane" to --tetraisopropyldisiloxane--.

In Column 82 at Line 10, Change "528.2." to --528.2,--.

In Column 82 at Line 67, Change "444.1." to --444.1,--.

In Column 83 at Line 32 (Approx.), Change "518.0." to --518.0,--.

In Column 83 at Line 66, Change "440.1." to --440.1,--.

In Column 84 at Line 32 (Approx.), Change "520.1." to --520.1,--.

In Column 85 at Line 1, Change "444.1." to --444.1,--.

In Column 85 at Line 34, Change "470.1." to --470.1,--.

In Column 86 at Line 1, Change "430.1." to --430.1,--.

In Column 87 at Line 10, Change "430.1." to --430.1,--.

In Column 99 at Line 12, Change "M" to --μM--.

In Column 106 at Line 33-34, Change "isobolgram" to --isobologram--.

In Column 107 at Line 23 (Approx.), Change "synergisn" to --synergism--.

In the Claims

In Column 110 at Line 59-60 (Approx.), In Claim 5, change "—C(O)R$'^2$," to -- —C(O)R$^{12}$,--.

In Column 148 at Line 56, In Claim 24, change "Ar$^a$" to --Ar$^3$--.

In Column 149 at Line 25 (Approx.), In Claim 24, change "napthyl" to --naphthyl--.

In Column 149 at Line 30 (Approx.), In Claim 27, change "72," to --claim 24,--.

In Column 149 at Line 37 (Approx.), In Claim 28, change "72," to --claim 24,--.